(12) United States Patent
Walker

(10) Patent No.: US 12,269,898 B2
(45) Date of Patent: Apr. 8, 2025

(54) TRANSTHYRETIN IMMUNOGLOBULIN FUSIONS

(71) Applicant: AMGEN INC., Thousand Oaks, CA (US)

(72) Inventor: Kenneth Walker, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/753,216

(22) PCT Filed: Oct. 3, 2018

(86) PCT No.: PCT/US2018/054237
§ 371 (c)(1),
(2) Date: Apr. 2, 2020

(87) PCT Pub. No.: WO2019/070901
PCT Pub. Date: Apr. 11, 2019

(65) Prior Publication Data
US 2020/0317795 A1  Oct. 8, 2020

Related U.S. Application Data

(60) Provisional application No. 62/568,217, filed on Oct. 4, 2017.

(51) Int. Cl.
| | | |
|---|---|---|
| C07K 19/00 | (2006.01) | |
| A61K 39/395 | (2006.01) | |
| A61P 35/00 | (2006.01) | |
| C07K 14/47 | (2006.01) | |
| C07K 16/28 | (2006.01) | |
| C07K 16/00 | (2006.01) | |
| C12N 15/63 | (2006.01) | |

(52) U.S. Cl.
CPC .......... *C07K 19/00* (2013.01); *A61K 39/3955* (2013.01); *A61P 35/00* (2018.01); *C07K 14/47* (2013.01); *C07K 16/00* (2013.01); *C07K 16/28* (2013.01); *C07K 16/2878* (2013.01); *C07K 2317/35* (2013.01); *C07K 2319/00* (2013.01); *C12N 15/63* (2013.01)

(58) Field of Classification Search
CPC ........ C07K 14/47; C07K 16/28; C07K 19/00; C07K 16/2878; C07K 2319/00; A61K 39/3955
See application file for complete search history.

(56) References Cited

U.S. PATENT DOCUMENTS

| | | | |
|---|---|---|---|
| 3,773,919 A | 11/1973 | Boswell et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,596,556 A | 6/1986 | Morrow et al. | |
| 4,790,824 A | 12/1988 | Morrow et al. | |
| 4,941,880 A | 7/1990 | Burns | |
| 4,946,778 A | 8/1990 | Ladner et al. | |
| 5,064,413 A | 11/1991 | McKinnon et al. | |
| 5,260,203 A | 11/1993 | Ladner et al. | |
| 5,312,335 A | 5/1994 | McKinnon et al. | |
| 5,383,851 A | 1/1995 | McKinnon, Jr. et al. | |
| 5,399,163 A | 3/1995 | Peterson et al. | |
| 8,586,713 B2 | 11/2013 | Davis et al. | |
| 8,633,153 B2 | 1/2014 | Walker et al. | |
| 9,546,203 B2 | 1/2017 | Kannan | |
| 2003/0191056 A1 | 10/2003 | Walker et al. | |
| 2008/0206229 A1 | 8/2008 | Ono et al. | |
| 2014/0234945 A1* | 8/2014 | Walker | A61K 47/60 435/252.35 |
| 2015/0010560 A1* | 1/2015 | Xu | C07K 16/28 435/69.6 |
| 2015/0064204 A1 | 3/2015 | Beers et al. | |
| 2016/0145333 A1 | 5/2016 | Coward et al. | |
| 2016/0264647 A1* | 9/2016 | Dimitrov | C07K 16/10 |
| 2022/0324924 A1 | 10/2022 | Walker | |

FOREIGN PATENT DOCUMENTS

| | | |
|---|---|---|
| CN | 106977609 A | 9/1981 |
| EP | 0036676 A1 | 9/1981 |
| EP | 0058481 A1 | 8/1982 |
| EP | 0133988 A2 | 3/1985 |
| EP | 0143949 A1 | 6/1985 |
| EP | 0088046 B1 | 12/1987 |
| WO | 1988/001649 A1 | 3/1988 |

(Continued)

OTHER PUBLICATIONS

Chen et al, 2013. Adv Drug Deliv Rev. 65(10): 1357-1369.*
Benjamini et al, 1991. Immunology: A Short Course, 2nd edition, p. 40 only.*
Ferrara et al (2015. mAbs. 7(1): 32-41).*
Walczak et al, 1997. The EMBO Journal. 16(17): 5386-5397.*
De Miguel et al, 2016. Cell Death and Differentiation. 23: 733-747.*
Almasan and Ashkenazi, "Apo2L/TRAIL: apoptosis signaling, biology, and potential for cancer therapy," Cytokine & Growth Factor Reviews 14: 337-348 (2003).
Arakawa et al., "Solvent interactions in pharmaceutical formulations," Pharm Res. 8(3): 285-291 (1991).
Atwell et al., "Stable Heterodimers from Remolding the Domain Interface of a Homodimer using a Phage Display Library," J. Mol. Biol. 270: 26-35 (1997).

(Continued)

*Primary Examiner* — Zachary C Howard
(74) *Attorney, Agent, or Firm* — Raymond M. Doss

(57) ABSTRACT

The present invention relates to transthyretin (TTR) fusions useful in the dimerization and tetramerization of antibodies and antibody fragments, such as Fabs. The TTR fusions proteins described herein are particularly useful in increasing antibody avidity and in enhancing antigen clustering. Methods for treating diseases using the fusion proteins of the present invention are described herein.

33 Claims, 20 Drawing Sheets

Specification includes a Sequence Listing.

(56) References Cited

FOREIGN PATENT DOCUMENTS

| | | |
|---|---|---|
| WO | 1993/015722 A1 | 8/1993 |
| WO | 1994/020069 A1 | 9/1994 |
| WO | 2003/086444 A1 | 10/2003 |
| WO | 2006/138181 A2 | 12/2006 |
| WO | 2007/085837 A1 | 8/2007 |
| WO | 2012/058393 A2 | 5/2012 |
| WO | 2012/170438 A2 | 12/2012 |
| WO | 2014/144632 A2 | 9/2014 |
| WO | 2014/210205 A1 | 12/2014 |
| WO | 2015/031667 A2 | 3/2015 |
| WO | 2015/092077 A1 | 6/2015 |
| WO | 2016/120811 A1 | 8/2016 |
| WO | 2016/122702 A1 | 8/2016 |
| WO | 2017/083604 A1 | 5/2017 |
| WO | 2019/070901 A1 | 4/2019 |

OTHER PUBLICATIONS

Carrillo et al., "The Multiple Sequence Alignment Problem in Biology," SIAM J. Applied Math. 48(5): 1073-1082 (1988).
Cheung et al., "Epitope-Specific Antibody Response to the Surface Antigen of Duck Hepatitis B Virus in Infected Ducks," Virology 176: 546-552 (1990).
Chothia et al., "Canonical Structures for the Hypervariable Regions of Immunoglobulins," J. Mol. Biol 196: 901-917 (1987).
Chothia et al., "Conformations of immunoglobulin hypervariable regions," Nature 342: 877-883 (1989).
Daigle et al., "Alternative functions for TRAIL receptors in eosinophils and neutrophils," Swiss Med. Wkly. 131: 231-237 (2001).
Daniels et al., "Conjugationof an anti-transferrin receptor IgG3-avidin fusion protein with biotinylated saporin results in significant enhancement of its cytotoxicity against malignant hematopoietic cells," Molecular Cancer Therapeutics 6(11): 2995-3008 (2007).
Davis et al., "SEEDbodies: fusion proteins based on strand-exchange engineered domain (SEED) CH3 heterodimers in an Fc analogue platform for asymmetric binders or immunofusions and bispecific antibodies," Protein Eng. Des. Sel. 23(4): 195-202 (2010).
De Kruif and Logtenberg, "Leucine Zipper Dimerized Bivalent and Bispecific scFv Antibodies from a Semi-synthetic Antibody Phage Display Library," The Journal of Biological Chemistry 271(13): 7630-7634 (1996).
Devereux et al., "A comprehensive set of sequence analysis programs for the VAX," Nucl. Acid Res. 12(1): 387-395 (1984).
Deyev et al., "Design of multivalent complexes using the barnase-barstar module," Nature Biotechnology 21(12): 1486-1492 (2003).
Eppstein et al., "Biological activity of liposome-encapsulated murine interferon γ is mediated by a cell membrane receptor," Proc. Natl. Acad. Sci. U.S.A. 82:3688-3692 (1985).
Foss et al., "The Pathway by Which the Tetrameric Protein Transthyretin Dissociates," Biochemistry 44: 15525-15533 (2005).
Goldenberg et al., "Multifunctional Antibodies by the Dock-and-Lock Method for Improved Cancer Imaging and Therapy by Pretargeting," The Journal of Nuclear Medicine 49(1): 158-163 (2008).
Henikoff et al., "Amino acid substitution matrices from protein blocks," Proc. Natl. Acad. Sci. U.S.A. 89(22): 10915-10919 (1992).
Jain et al., "Engineering antibodies for clinical applications," Trends in Biotechnology 25(7): 307-316 (2007).
Kendrick et al., "Physical Stabilization of Proteins in Aqueous Solution," in Rational Design of Stable Protein Formulations, Carpenter and Manning, eds., Pharmaceutical Biotechnology 13: 61-84 (2002).
Kipriyanov et al., "Affinity enhancement of a recombinant antibody: formation of complexes with multiple valency by a single-chain Fv fragment-core streptavidin fusion," Protein Engineering 9(2): 203-211 (1996).
Kirkland et al., "Analysis of the fine specificity and cross-reactivity of monoclonal anti-lipid A antibodies," J. Immunol. 137:3614-3619 (1986).
Kriangkum et al., "Bispecific and bifunctional single chain recombinant antibodies," Biomolecular Engineering 18(2): 31-40 (2001).
Labrijn et al., "Efficient generation of stable bispecific IgGI by controlled Fab-arm exchange," Proc. Natl. Acad. Sci U.S.A. 110(13): 5145-5150 (2013).
Langer et al., "Biocompatibility of polymeric delivery systems for macromolecules," J. Biomed. Mater. Res. 15:267-277 (1981).
Langer "Controlled Release of Macromolecules," Chemtech. 12:98-105 (1982).
MacCallum et al., "Antibody-antigen Interactions: Contact Analysis and Binding Site Topography," J. Mol. Biol 262: 732-745 (1996).
Martin and Thornton, "Structural Families in Loops of Homologous Proteins: Automatic Classification, Modelling and Application to Antibodies," J. Mol. Biol 263(5): 800-815 (1996).
Mita et al., "Cloning and sequence analysis of cDNA for human prealbumin," Biochem. Biophys. Res. Commun., 124(2):558-564 (1984).
Moldenhauer et al., "Identity of HML-1 Antigen on Intestinal Intraepithelial T Cells and of B-ly7 Antigen on Hairy Cell Leukaemia," Scand. J. Immunol. 32(2): 77-82 (1990).
Moore et al., "A novel bispecific antibody format enables simultaneous bivalent and monovalent co-engagement of distinct target antigens," mAbs 3(6): 546-557 (2011).
Morel et al., "Monoclonal antibodies to bovine serum albumin: Affinity and specificity determinations," Molecular Immunology 25(1): 7-15 (1988).
Nocentini, et al., "A new member of the tumor necrosis factor/nerve growth factor receptor family inhibits T cell receptor-induced apoptosis," Proc. Natl. Acad. Sci. USA 94:6216-6221 (1997).
Pack et al., "Improved Bivalent Miniantibodies, with Identical Avidity as Whole Antibodies, Produced by High Cell Density Fermentation of Escherichia coli," Biotechnology 11(11): 1271-1277 (1993).
Penchala et al., "A biomimetic approach for enhancing the in vivo half-life of peptides," Nat Chem Biol. 11(10): 793-798 (2015).
Randolph and Jones, "Surfactant-Protein Interactions," Pharm Biotechnol. 13: 159-175 (2002).
Ridgway et al., "'Knobs-into-holes' engineering of antibody CH3 domains for heavy chain heterodimerization," Protein Engineering, 9(7): 617-621 (1996).
Schultz et al., "A Tetravalent Single-chain Antibody-Streptavidin Fusion Protein for Pretargeted Lymphoma Therapy," Cancer Research 60(23): 6663-6669 (2000).
Sidman et al., "Controlled Release of Macromolecules and Pharmaceuticals from Synthetic Polypeptides Based on Glutamic Acid," Biopolymers 22:547-556 (1983).
Spierings et al., "Tissue Distribution of the Death Ligand TRAIL and Its Receptors," J. Histochem. Cytochem. 52(6): 821-831 (2004).
Spiess et al., "Alternative molecular formats and therapeutic applications for bispecific antibodies," Molecular Immunology 67(2): 95-106 (2015).
Stahli et al., "Distinction of Epitopes by Monoclonal Antibodies," Methods in Enzymology 92:242-253 (1983).
Strop et al., "Generating Bispecific Human IgGI and IgG2 Antibodies from Any Antibody Pair," J. Mol. Biol. 420: 204-219 (2012).
Von Kreudenstein et al., "Improving biophysical properties of a bispecific antibody scaffold to aid developability," mAbs, 5(5): 646-654 (2013).
Walczak et al., "TRAIL-R2: a novel apoptosis-mediating receptor for Trail," EMBO J. 16(17): 5386-5397 (1997).
Wang et al., "Multimeric Anti-DR5 lgM antibody displays potent cytotoxicity in vitro and promotes tumor regression in vivo," IGM Biosciences, Inc., Abstract No. 1702 AACR Annual Meeting 2017, 1 page.
Wolff et al., "Monoclonal Antibody Homodimers: Enhanced Antitumor Activity in Nude Mice," Cancer Research 53(11): 2560-2565 (1993).
Chen et al., "Fusion protein linkers: Property, design and functionality," Advanced Drug Delivery Reviews 65(10): 1357-1369 (2012).
Bush et al., "Collision Cross Sections of Proteins and Their Complexes: A Calibration Framework and Database for Gas-Phase Structural Biology," Analytical Chemistry 82(22):9557-9565 (2010).

(56) References Cited

OTHER PUBLICATIONS

Engler et al., "A One Pot, One Step, Precision Cloning Method with High Throughput Capability," *PLOS One* 3(11):e3647 (2008).
Gil and Schrum, "Strategies to stabilize compact folding and minimize aggregation of antibody-based fragments," *Advances in Bioscience and Biotechnology* 4(4a):73-84 (2013).
Sant'Anna et al., "Cavity filling mutations at the thyroxine-binding site dramatically increase transthyretin stability and prevent its aggregation," *Scientific Reports* 7(1):44709 (2017).
Uemichi et al., "A new mutant transthyretin (Arg 10) associated with familial amyloid polyneuropathy," *Journal of Medical Genetics* 29(12):888-891 (1992).
Abcam Limited, Anti-DR5 antibody [EPR19310] (ab199357), retrieved from the internet: https://www.abcam.com/en-us/products/primary-antibodies/dr5-antibody-epr19310-ab199357#, downloaded Jun. 24, 2024; copy also attached as Exhibit A to Response to Final Office Action.
Abdulghani and El-Deiry, "Trail receptor signaling and therapeutics," *Expert Opinion on Therapeutic Targets* 14(10):1091-1108 (2010).
Dubuisson and Micheau, "Antibodies and Derivatives Targeting DR4 and DR5 for Cancer Therapy," *Antibodies* 6(4):16 (2017).
Fesik, "Promoting Apoptosis as a Strategy for Cancer Drug Discovery," *Nature Reviews Cancer* 5(11):876-885 (2005).
Gerspach et al., "Death Ligands Designed to Kill: Development and Application of Targeted Cancer Therapeutics Based on Proapoptotic TNF Family Ligands," *Results and Problems in Cell Differentiation* 49:241-273 (2009).
Johnstone et al., "The TRAIL apoptotic pathway in cancer onset, progression and therapy," *Nature Reviews Cancer* 8(10):782-798 (2008).
Trivedi and Mishra, "Trailing TRAIL resistance: novel targets for TRAIL sensitization in cancer cells," *Frontiers in Oncology* 5:69 (2015).

\* cited by examiner

Figure 1
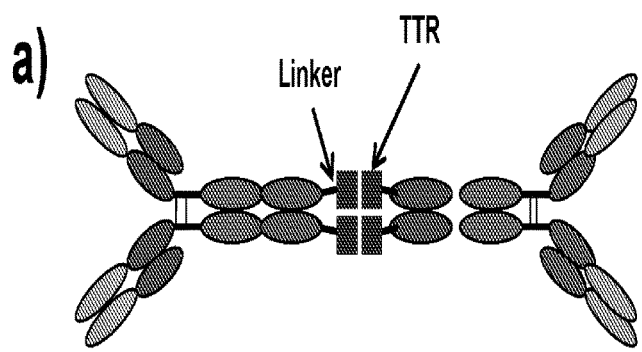
a) TTR antibody homodimer fusion protein
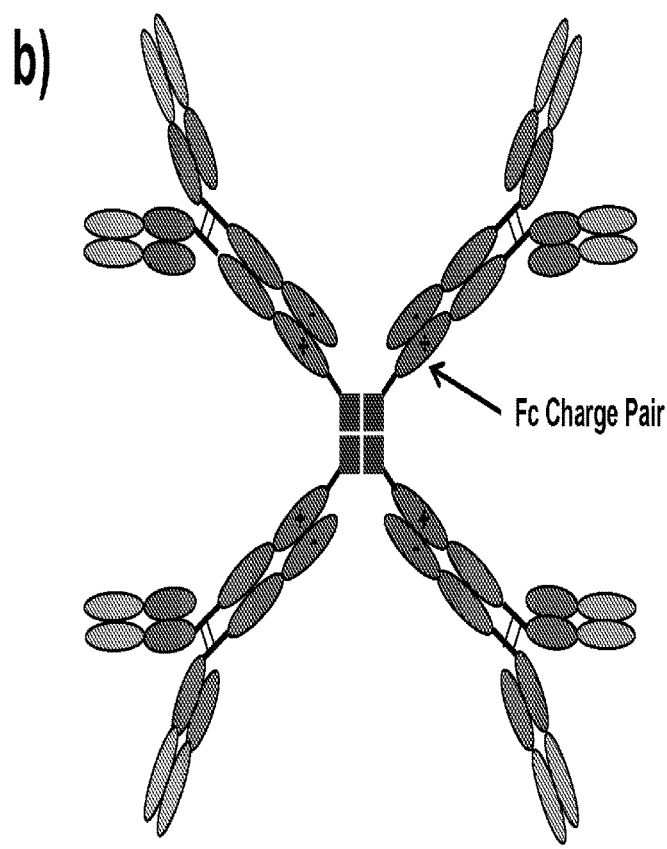
b) TTR antibody homotetramer fusion protein
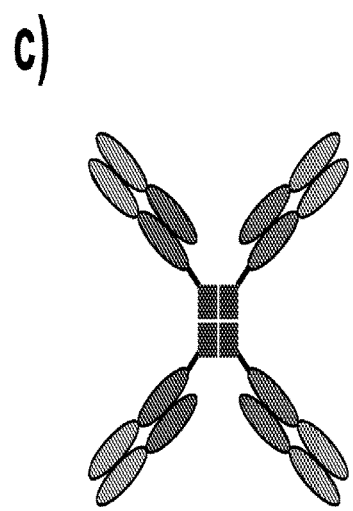
c) TTR Fab homotetramer fusion protein

Figure 3
a) Ab-TTR
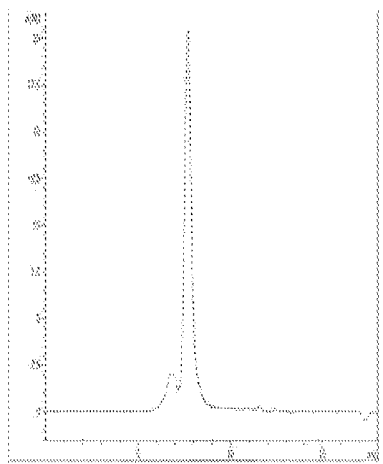
b) Ab-(G4S)$_1$-TTR
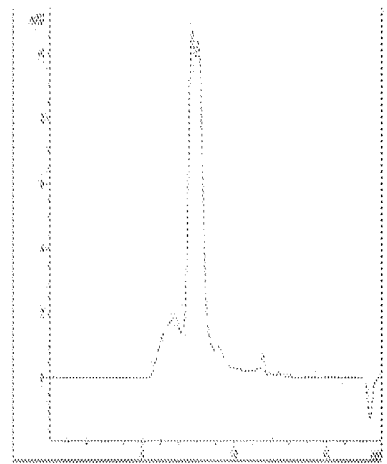
c) Ab-(G4S)$_2$-TTR
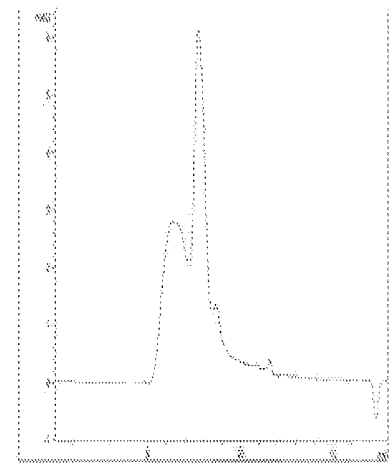
d) Ab-(G4S)$_3$-TTR
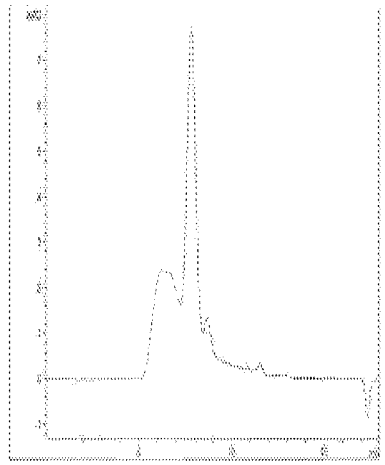
e) Ab-(G4S)$_4$-TTR
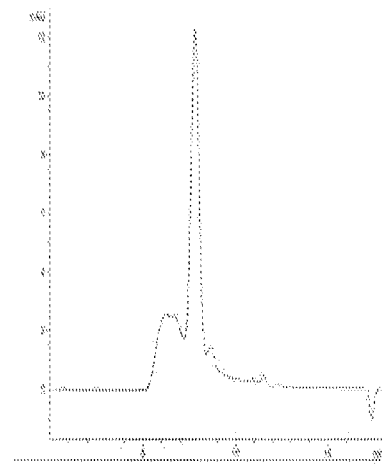

Lanes 1 and 4 = anti-GITR TTR antibody homodimer
Lanes 2 and 5 = anti-GITR TTR antibody homotetramer
Lanes 3 and 6 = anti-GITR TTR Fab homotetramer SEC analysis of each of the anti-GITR TTR fusion proteins Left peak: anti-GITR TTR antibody homotetramer
Middle peak: anti-GITR TTR antibody homodimer
Right peak: anti-GITR TTR Fab homotetramer Figure 9
a) 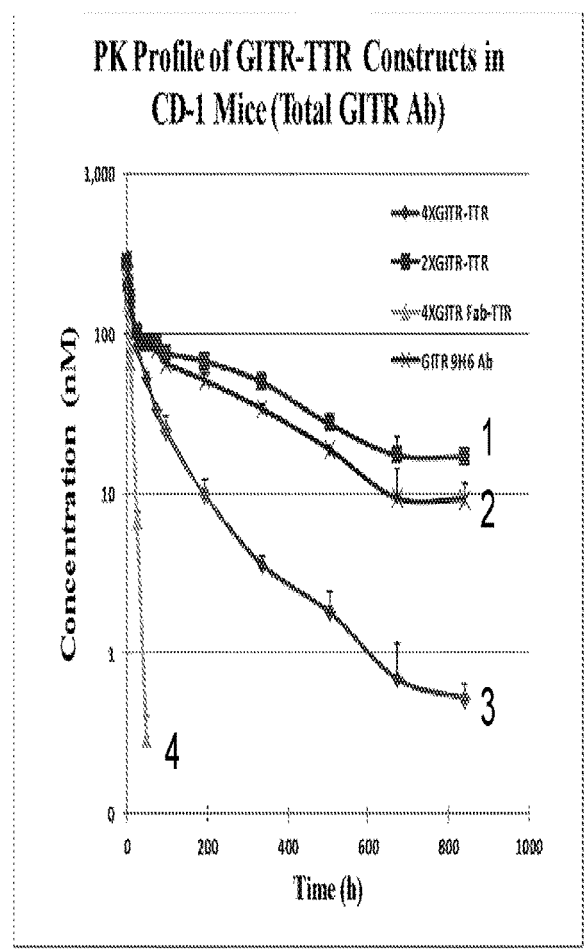
b) 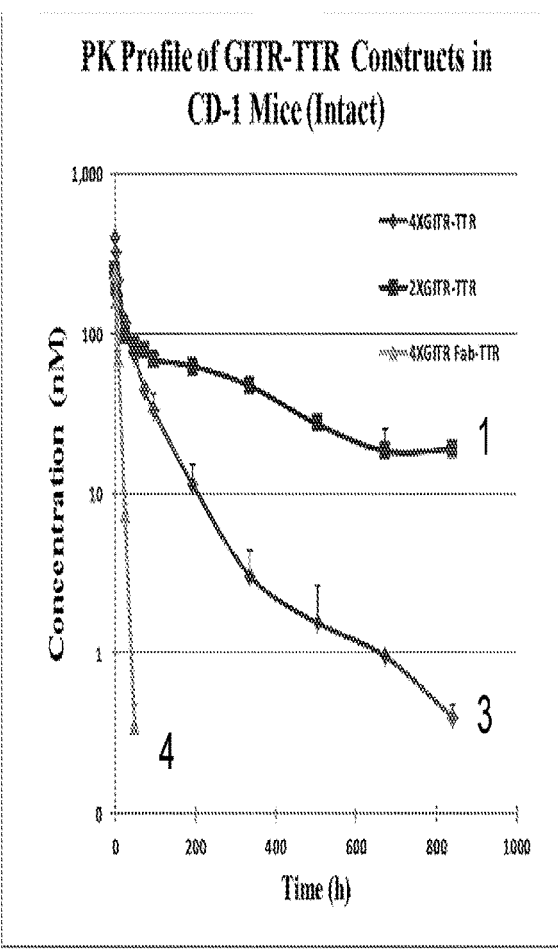

Anti-TRAILR2 antibody homotetramer

Figure 13
Anti-TRAILR2 TTR Fab homotetramer
Anti-TRAILR2 TTR antibody homodimer
anti-TRAILR2 TTR antibody homotetramer
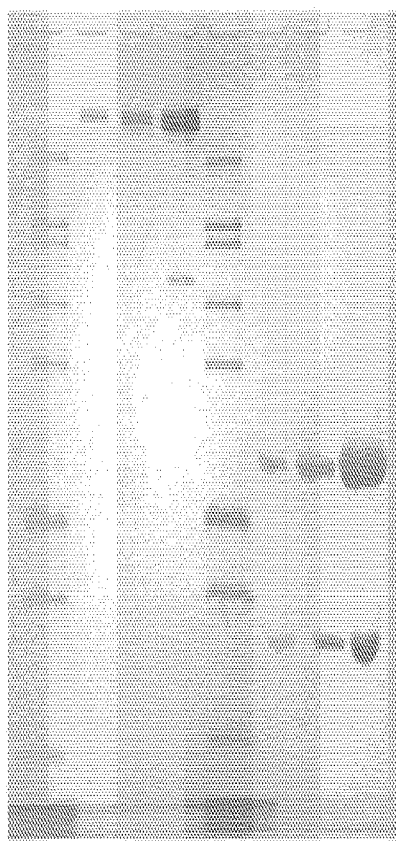
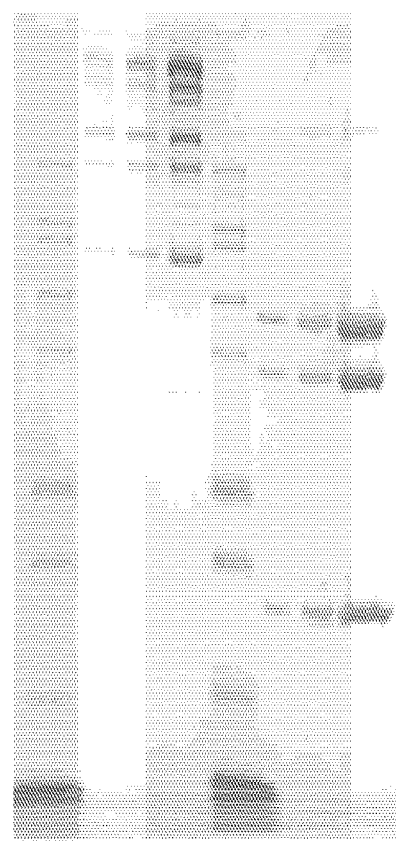

SEC Purified anti-TRAILR2 TTR Fusions

Figure 15
Murine PK of anti-TRAILR2-TTR Conjugates
a)
b)
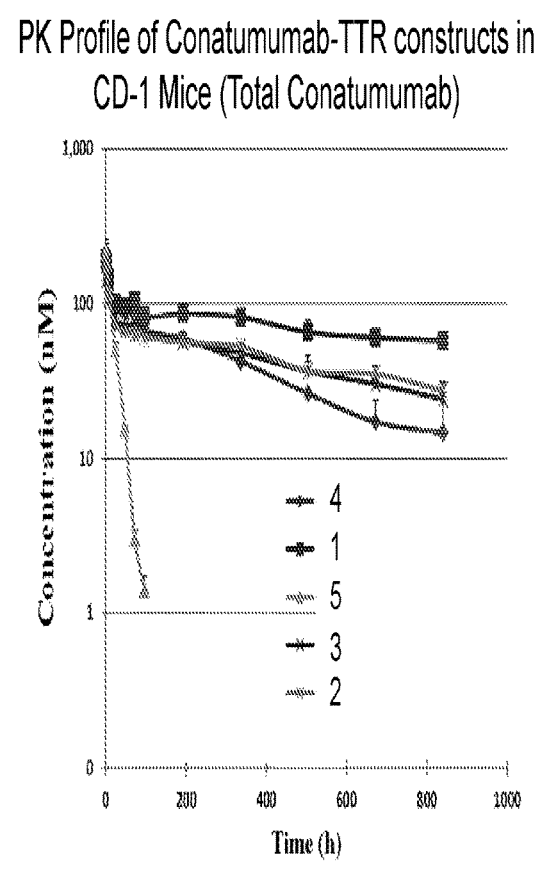
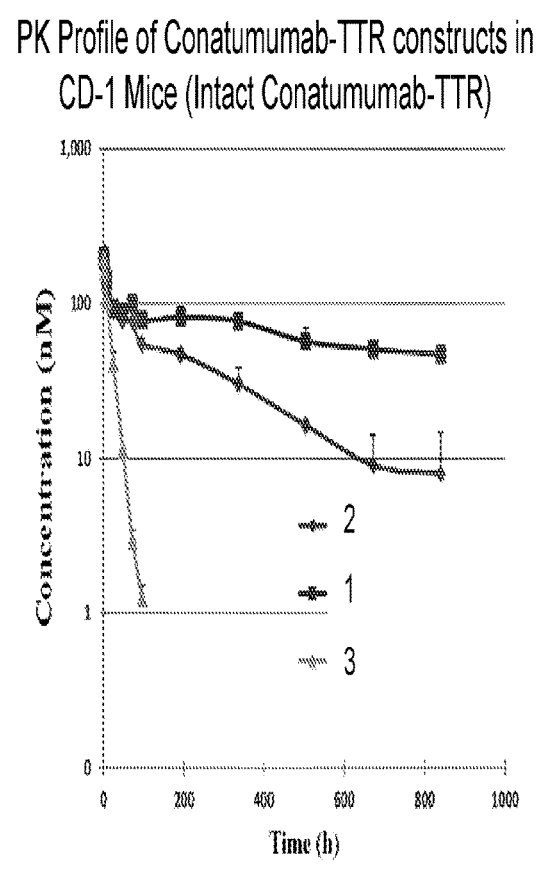

Tetramerization of Conatumumab Substantially Improves Potency in Cell Based Assay

Tetramerization of Conatumumab Improves Potency on Primary Human Keratinocytes Tetramerized Conatumumab Reduces Tumors in Murine Colo205 Model Tetramerized Conatumumab Reduces Tumors in Murine SW403 Model

TRANSTHYRETIN IMMUNOGLOBULIN FUSIONS

CROSS REFERENCE TO RELATED APPLICATIONS

This application is a national stage application under 35 U.S.C. § 371 of International Application No. PCT/US2018/054237, having an international filing date of Oct. 3, 2018; which claims the benefit under 35 U.S.C. 119(e) of U.S. Provisional Application No. 62/568,217, filed Oct. 4, 2017, all of which are incorporated by reference herein in their entireties.

FIELD OF THE INVENTION

The present invention relates to transthyretin (TTR) fusions useful in the dimerization and tetramerization of antibodies and antibody fragments, such as Fabs. The TTR fusions proteins described herein are particularly useful in increasing antibody avidity and in enhancing antigen clustering. Methods for treating diseases using the fusion proteins of the present invention are described herein. REFERENCE TO THE SEQUENCE LISTING The present application is being filed along with a Sequence Listing in electronic format via ePCT. The Sequence Listing is provided as a text file entitledA-2196-US-PCT_SubSeqlisting.txt, created: Nov. 1, 2024, which is 84,744 bytes in size. The information in the electronic format of the Sequence Listing is incorporated herein by reference in its entirety.

BACKGROUND OF THE INVENTION

Transthyretin (TTR) is a non-covalent tetrameric human serum and cerebral spinal fluid protein responsible for enhancing the serum half-life of retinol binding protein, as well as carrying a portion of circulating thyroxine. The native human monomer has an approximate molecular weight of 14 kDa, though TTR is typically present as a 56 kDa tetrameric serum protein.

TTR and TTR variants have previously fused to biologically active agents in order to increase the serum half-life of such agents. For example, substantially homogenous preparations of TTR- (or a TTR variant-) biologically active agent fusions and PEG-TTR- (or PEG-TTR variant-) biologically active agent fusions have been developed which demonstrate increased serum half-life compared to the biologically active agent alone. See, e.g., US20030191056, which is hereby incorporated by reference in its entirety.

In addition, previous efforts to multimerize proteins include the use of streptavidin (Kipriyanov et al., *Protein Engineering*, 9(2):203-211 (1996)), helix-turn-helix constructs (Kriangkum et al., *Biomolecular Engineering*, 18:31-40 (2001)), leucine zippers (Kruif et al., *The Journal of Biological Chemistry*, 271(13):7630-7634, 1996 (1996)), barnase/barstar complexes (Deyev et al., *Nature Biotechnology*, 21(12):1486-1492 (2003)), and Dock N Lock technology (protein kinase and A-kinase anchoring protein anchoring domain interactions) (Goldenberg et al., *Journal of Nuclear Medicine*, 49(1):158-163 (2008)).

However, there remains a need for multimerized proteins, such as multimerized whole antibodies and antibody fragments (e.g., Fabs), which demonstrate enhanced biological and therapeutic properties. For example, there remains a need for multimerized proteins which have increased antibody avidity and enhanced antigen clustering compared to their non-multimerized counterparts.

SUMMARY OF THE INVENTION

In one aspect, the present invention relates to a homodimer fusion protein comprising two antigen binding proteins, wherein the antigen binding proteins are linked to a protein complex. In a particular aspect, the protein complex is a TTR protein complex. In a particular aspect, the antigen binding protein is an antibody. In another particular aspect, the antigen binding proteins are directly fused without a linker to the protein complex. In another particular aspect, the C-terminus of the antigen binding protein is directly fused to an N-terminus present in the TTR protein complex. In some embodiments, the antigen binding proteins are fused to the protein complex via a linker. In other embodiments, the C-terminus of the antigen binding protein is linked to an N-terminus present in the TTR protein complex. The linker may be an amino acid linker, such as an amino acid linker that is 1-20 amino acids in length. In particular embodiments, the amino acid linker is GGGGS (SEQ ID NO: 47), (GGGGS)$_2$ (SEQ ID NO: 48), (GGGGS)$_3$ (SEQ ID NO: 49), (GGGGS)$_4$ (SEQ ID NO: 50), (GGGGS)$_5$ (SEQ ID NO: 51), or (GGGGS)$_6$ (SEQ ID NO: 52).

In another aspect, the present invention relates to a homotetramer fusion protein comprising four antigen binding proteins, wherein the antigen binding proteins are linked to a protein complex. In one aspect, the protein complex is a TTR protein complex. In another aspect, the antigen binding protein is an antibody. The antigen binding protein may be a Fab. In some embodiments, the antigen binding proteins are directly fused without a linker to said protein complex. In particular embodiments, the C-terminus of the antigen binding protein is directly fused to an N-terminus present in the TTR protein complex. In other embodiments, the antigen binding proteins are fused to said protein complex via a linker. The C-terminus of the antigen binding protein may be linked to an N-terminus present in the TTR protein complex. In some embodiments, the linker is an amino acid linker, such as an amino acid linker that is 1-20 amino acids in length. In particular embodiments, the amino acid linker is GGGGS (SEQ ID NO: 47), (GGGGS)$_2$ (SEQ ID NO: 48), (GGGGS)$_3$ (SEQ ID NO: 49), (GGGGS)$_4$ (SEQ ID NO: 50), (GGGGS)$_5$ (SEQ ID NO: 51), or (GGGGS)$_6$ (SEQ ID NO: 52).

The present invention also relates to a pharmaceutical composition comprising any of the homodimer or homotetramer fusion proteins discussed above.

In addition, the present invention relates to a method of treating cancer using any of the homodimer or homotetramer fusion proteins discussed above. Moreover, the present invention relates to uses of any of the homodimer or homotetramer fusion proteins discussed above in the treatment of cancer. In another aspect, the present invention relates any of the homodimer or homotetramer fusion proteins discussed above for use in the treatment of cancer.

In some aspects, the present invention relates to one or more isolated nucleic acid(s) encoding any of the homodimer or homotetramer fusion proteins discussed above. Expression vectors comprising such nucleic acids are also contemplated, as are recombinant host cells comprising the nucleic acids and/or vectors discussed herein. In particular embodiments, the recombinant host cell is a Chinese hamster ovary (CHO) cell, E5 cell, baby hamster kidney (BHK)

cell, monkey kidney (COS) cell, human hepatocellular carcinoma cell, or human embryonic kidney 293 (HEK 293) cell.

Methods of making any of the homodimer or homotetramer fusion proteins discussed above are also part of the present invention. Such methods may comprise a) culturing the recombinant host cell of claim 32 or 33; and b) isolating the homodimer or homotetramer fusion protein from said culture.

BRIEF DESCRIPTION OF THE DRAWINGS

FIG. 1 is a schematic representation of the homomultimer constructs of the present invention. FIG. 1a is an exemplary TTR antibody homodimer fusion protein, where the C-terminus of both antibody heavy chains is linked to the N-terminus of each TTR subunit. FIG. 1b is an exemplary TTR antibody homotetramer fusion protein, where one of the two heavy chains of each antibody C-terminus is linked to the N-terminus of each TTR subunit. The "+" and "−" signs indicate Fc charge pairs which allow for consistent attachment of one TTR subunit per whole antibody. FIG. 1c is an exemplary TTR Fab homotetramer fusion protein, where the C-terminus of each Fab fragment is linked to the N-terminus of each TTR subunit. Each of FIGS. 1a-1c shows the optional linker between the heavy chain and TTR.

FIG. 2 is further discussed in Example 2.

FIG. 3 is a series of HPLC size exclusion chromatography (SEC) analyses of the anti-CB1 TTR antibody homodimer fusion protein with no linker, a ($G_4S$) linker, a ($G_4S$)$_2$ linker, a ($G_4S$)$_3$ linker, or a ($G_4S$)$_4$ linker. FIG. 3 is further discussed in Example 2.

FIG. 4 is further discussed in Example 3.

FIG. 5 is further discussed in Example 4.

FIG. 6 is further discussed in Example 4.

FIG. 7 is further discussed in Example 4.

FIG. 8 demonstrates that the melting temperatures of the TTR fusion proteins are comparable or better than the parental Ab, indicating that the formed TTR fusion proteins are robust.

FIG. 9 a) is the result of the in vivo (mouse) pharmacokinetic (PK) analysis of the total anti-GITR antibody species. FIG. 9 b) is the result of the in vivo (mouse) PK analysis of the intact anti-GITR TTR fusion proteins.

FIG. 10 b) demonstrates that higher affinity did not translate to higher potency in cell based assays.

FIG. 13 is a series of SDS-PAGE gels that demonstrate that the anti-TRAILR2 TTR Fab homotetramer, anti-TRAILR2 TTR antibody homodimer, and anti-TRAILR2 TTR antibody homotetramer are correctly assembled based on the non-heated, non-reduced lanes. Upon heating and reduction, the molecules break down to their expected component chains (upper band(s) are heavy chains and lowest band is light chain).

FIG. 15 a) is the result of the in vivo (mouse) PK analysis of the total anti-TRAILR2 antibody species. FIG. 15 b) is the result of the in vivo (mouse) PK analysis of the intact anti-TRAILR2 TTR fusion proteins.

DETAILED DESCRIPTION

Figure 2:
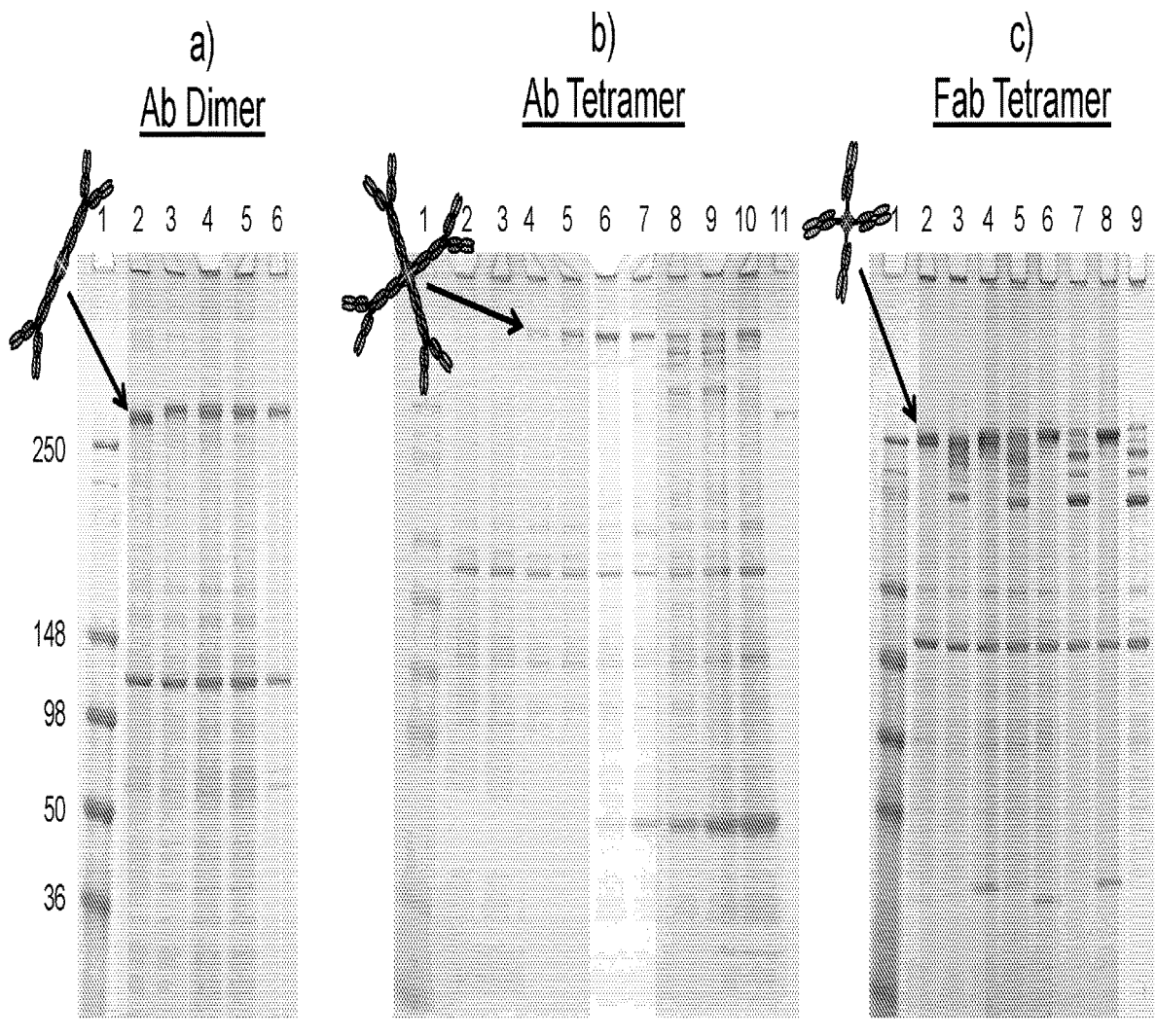
FIG. 2 is a series of SDS-PAGE gels that demonstrate that the anti-CB1 TTR antibody homodimer with no linker and varying linker lengths (FIG. 2a), anti-CB1 TTR antibody homotetramer with no linker (FIG. 2b), and anti-CB1 TTR Fab homotetramer proteins with no linker (FIG. 2c), respectively, are robustly expressed in HEK 293 cells.

The section headings used herein are for organizational purposes only and are not to be construed as limiting the subject matter described.

Unless otherwise defined herein, scientific and technical terms used in connection with the present application have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All embodiments narrower in scope in any way than the variations defined by specific paragraphs herein are to be considered included in this disclosure. For example, certain aspects are described as a genus, and it should be understood that every member of a genus can be, individually, an embodiment. Also, aspects described as a genus or selecting a member of a genus should be understood to embrace combinations of two or more members of the genus. It should also be understood that while various embodiments in the specification are presented using "comprising" language, under various circumstances, a related embodiment may also be described using "consisting of" or "consisting essentially of" language.

In this application, the use of "or" means "and/or" unless stated otherwise. Furthermore, the use of the term "including," as well as other forms, such as "includes" and "included", is not limited. Also, terms such as "element" or "component" encompass both elements and components comprising one unit and elements and components that comprise more than one subunit unless specifically stated otherwise.

Definitions

"Amino acid" includes its standard meaning in the art. The twenty naturally-occurring amino acids and their abbreviations follow conventional usage. See, Immunology-A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as [alpha]-, [alpha]-disubstituted amino acids, N-alkyl amino acids, and other unconventional amino acids may also be suitable components for polypeptides and are included in the phrase "amino acid." Examples of unconventional amino acids include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

An "antagonist" as used herein generally refers to a molecule, for example, an antigen binding protein such as provided herein, that can bind an antigen and inhibit, reduce, or eliminate biological signaling associated with the antigen.

The term "antibody" refers to an immunoglobulin of any isotype, or a fragment thereof that can compete with the intact antibody for binding to the target antigen. An "antibody" is a type of antigen binding protein. The term "antibody" includes, but is not limited to, monoclonal antibodies, human antibodies, humanized antibodies, chimeric antibodies, and anti-idiotypic (anti-Id) antibodies. Antibodies can be of any isotype/class (e.g., IgG, IgE, IgM, IgD, IgA and IgY), or subclass (e.g., IgG1, IgG2, IgG3, and IgG4). In some embodiments, an antibody comprises at least two full-length heavy chains and two full-length light chains. In other embodiments, an antibody includes fewer chains such as antibodies naturally occurring in camelids which may comprise only heavy chains. Antibodies may be derived solely from a single source, or may be "chimeric" wherein different portions of the antibody are derived from two different antibodies as described further below. The antigen binding proteins, antibodies, or binding fragments may be produced, for example, in hybridomas, by recombinant DNA techniques, or by enzymatic or chemical cleavage of intact antibodies.

The term "antigen" refers to a molecule or a portion of a molecule capable of being bound by a binding agent, such as an antigen binding protein (including, e.g., an antibody), and additionally capable of being used in an animal to produce antibodies capable of binding to that antigen. An antigen may possess one or more epitopes that are capable of interacting with different antigen binding proteins, e.g., antibodies.

An "antigen binding protein" as used herein means any protein that specifically binds a specified target antigen. The term includes polypeptides that include at least one antigen binding region. The term also encompasses antibodies that comprise at least two full-length heavy chains and two full-length light chains, as well as derivatives, variants, fragments, and mutations thereof. An antigen binding protein also includes Fab, Fab', F(ab')$_2$, Fv fragments, domain antibodies such as Nanobodies® and single-chain antibodies, as described in more detail below.

An "antigen binding region" or "antigen binding domain" means the portion of a protein, such as an antibody or a fragment, derivative, or variant thereof, that specifically binds to, interacts with, or recognizes a given epitope or site on a molecule (e.g., an antigen). For example, the portion of an antigen binding protein that contains the amino acid residues that interact with an antigen and confer on the antigen binding protein its specificity and affinity for the antigen is referred to as "antigen binding region." An antigen binding region can include one or more "complementarity determining regions" ("CDRs"). Certain antigen binding regions also include one or more "framework" regions. "Framework" regions can contribute directly to the specific binding of the antigen binding protein, but typically aid in maintaining the proper conformation of the CDRs to promote binding between the antigen binding region and an antigen.

The terms "cancer", "tumor", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include melanoma, lung cancer, head and neck cancer, renal cell cancer, colon cancer, colorectal cancer, squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer, endometrial carcinoma, myeloma (such as multiple myeloma), salivary gland carcinoma, kidney cancer such as renal cell carcinoma and Wilms' tumors, basal cell carcinoma, prostate cancer, vulval cancer, thyroid cancer, testicular cancer, and esophageal cancer.

The terms "CDR," and its plural "CDRs" (also referred to as "hypervariable regions"), refer to the complementarity determining region of a protein, such as an antibody or a fragment, derivative, or variant thereof. The light chain variable region and the heavy chain variable region each contain three CDRs. For example, the light chain variable region contains the following CDRs: CDR-L1, CDR-L2 and CDR-L3; and the heavy chain variable region contains the following CDRs: CDR-H1, CDR-H2 and CDR-H3. CDRs contain most of the residues responsible for specific interactions of the antibody with the antigen and hence contribute to the functional activity of an antibody molecule. CDRs are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Despite differing boundaries, each of these systems has some degree of overlap in what constitutes a CDR within the variable sequences. CDR definitions according to these systems may therefore differ in length and boundary areas with respect to the adjacent framework region. See, e.g., Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding site is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). For a review of the antibody structure, see Antibodies: A Laboratory Manual, Cold Spring Harbor Laboratory, eds. Harlow et al., 1988.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "compete" when used in the context of antigen binding proteins (e.g., antibodies or fragments thereof) that compete for the same epitope means competition between antigen binding proteins and is determined by an assay in which the antigen binding protein (e.g., antibody or fragment thereof) under test prevents or inhibits specific binding of a reference antigen binding protein to a common antigen. Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells expressing the antigen, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided herein. For instance, in one embodiment, competition is determined according to a BiaCore assay. Usually, when a competing antigen binding protein is present in excess, it will inhibit specific binding of a reference antigen binding protein to a common antigen by at least 20%, 25%, 30%, 35%, 40%, 45%, 50%, 55%, 60%, 65%, 70% or 75%. In some instances, binding is inhibited by at least 80%, 85%, 90%, 95%, or 97% or more.

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequences. "Control sequences" can include leader sequences and/or fusion partner sequences.

A "derivative" of a polypeptide is a polypeptide that has been chemically modified in some manner distinct from insertion, deletion, or substitution variants, e.g., via conjugation to another chemical moiety.

A "domain antibody" is an immunologically functional immunoglobulin fragment containing only the variable region of a heavy chain or the variable region of a light chain. Examples of domain antibodies include Nanobodies®. In some instances, two or more $V_H$ regions are covalently joined with a peptide linker to create a bivalent domain antibody. The two $V_H$ regions of a bivalent domain antibody may target the same or different antigens.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with cancer. In some embodiments, the effective amount is a therapeutically effective amount or a prophylactically effective amount. A "therapeutically effective amount" is an amount sufficient to remedy a disease state (e.g. cancer) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of cancer, or reducing the likelihood of the onset (or reoccurrence) of cancer or cancer symptoms. The full therapeutic or prophylactic effect does not necessarily occur by administration of one dose, and may occur only after administration of a series of doses. Thus, a therapeutically or prophylactically effective amount may be administered in one or more administrations.

The term "epitope" refers to the portion of an antigen capable of being recognized and specifically bound by an antigen binding protein (e.g., an antibody). In the context of polypeptides, epitopes can be formed from contiguous amino acids or non-contiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more typically, at least 5 or 8-10 amino acids in a unique spatial conformation. A "linear epitope" or a "sequential epitope" is an epitope that is recognized by an antigen binding protein (e.g., an antibody) by its linear sequence of amino acids, or primary structure. A "conformational epitope" or a "nonsequential epitope" is an epitope that is recognized by an antigen binding protein (e.g., an antibody) via its tertiary structure. The residues that constitute these epitopes may not be contiguous in the primary amino acid sequence but are brought close together in the tertiary structure of the molecule. Linear and conformational epitopes generally behave differently when a protein is denatured, fragmented, or reduced.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

A "Fab fragment" or "Fab" is comprised of one light chain and the $C_H1$ and variable regions of one heavy chain. The heavy chain of a Fab molecule cannot form a disulfide bond with another heavy chain molecule.

A "Fab' fragment" or "Fab'" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an $F(ab')_2$ molecule.

A "$F(ab')_2$ fragment" or "$F(ab')_2$" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

An "Fc region" contains two heavy chain fragments comprising the $C_H2$ and $C_H3$ domains of an antibody. The two heavy chain fragments are held together by two or more disulfide bonds and by hydrophobic interactions of the $C_H3$ domains.

The "Fv region" comprises the variable regions from both the heavy and light chains, but lacks the constant regions.

The term "heavy chain" as used with respect to an antigen binding protein, antibody, or fragment thereof, includes a full-length heavy chain and fragments thereof having sufficient variable region sequence to confer binding specificity. A full-length heavy chain includes a variable region domain ($V_H$) and three constant region domains ($C_H1$, $C_H2$, and $C_H3$). The $V_H$ domain is at the amino-terminus of the polypeptide, and the $C_H$ domains are at the carboxyl-terminus, with the $C_H3$ being closest to the carboxy-terminus of the polypeptide. Heavy chains may be of any isotype such as IgG (including IgG1, IgG2, IgG3 and IgG4 subtypes), IgA (including IgA1 and IgA2 subtypes), IgM and IgE.

"Hematological cancers" are cancer that begins in bloodforming tissue, such as the bone marrow, or in the cells of the immune system. Examples of hematologic cancer are leukemia, lymphoma, and multiple myeloma.

The term "homodimer fusion protein" refers to a fusion protein comprising two of the same antigen binding proteins. For example, an antibody homodimer fusion protein refers to a fusion protein comprising two of the same antibodies. In a particular example, the homodimer can be a TTR homodimer fusion protein which comprises two of the same antibodies linked via a TTR protein, as described herein.

The term "homotetramer fusion protein" refers to a fusion protein comprising four of the same antigen binding proteins. For example, an antibody homotetramer fusion protein refers to a fusion protein comprising four of the same antibodies. In another example, a Fab homotetramer fusion protein refers to a fusion protein comprising four of the same Fab fragments. In a particular example, the homotetramer can be a TTR homotetramer fusion protein which comprises two of the same antigen binding proteins (e.g., two of the same antibodies, or two of the same Fab fragments) linked via a TTR protein, as described herein.

The term "host cell" means a cell that has been transformed with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are aligned in a way that gives the largest match between the sequences. The computer program used to determine percent identity is the GCG package, which includes GAP (Devereux et al., 1984, Nucl. Acid Res. 12:387; Genetics Computer Group, University of Wisconsin, Madison, WI). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program are the following:
  Algorithm: Needleman et al., 1970, J. Mol. Biol. 48:443-453;
  Comparison matrix: BLOSUM 62 from Henikoff et al., 1992, supra;
  Gap Penalty: 12 (but with no penalty for end gaps)
  Gap Length Penalty: 4
  Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The phrase "immune modulator" refers to a molecule that induces, enhances or suppresses an immune response. An immune activator is a molecule that induces or amplifies an immune response. An immune suppressor is a molecule that reduces or suppresses an immune response. Thus, an activation immunotherapy is a therapy that involves administering a molecule(s) to induce or enhance a subject's immune system. A suppression immunotherapy is a therapy in which a subject is treated with a molecule(s) to reduce or suppress the subject's immune system.

The term "fragment" of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelids or rabbit. It is contemplated further that a functional portion of the antigen binding proteins disclosed herein, for example, one or more CDRs, could be covalently bound to a second protein or to a small molecule to create a therapeutic agent directed to a particular target in the body or having a prolonged serum half-life.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

The term "isolated polypeptide," "purified polypeptide," "isolated protein" or "purified protein" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 90%, about 95% or more of the proteins in the composition.

The term "light chain" as used with respect to an antigen binding protein, antibody, or fragments thereof, includes a full-length light chain and fragments thereof having sufficient variable region sequence to confer binding specificity. A full-length light chain includes a variable region domain ($V_L$) and a constant region domain ($C_L$). The variable region domain of the light chain is at the amino-terminus of the polypeptide. Light chains include kappa chains and lambda chains.

The term "naturally occurring" as used throughout the specification in connection with biological materials such as polypeptides, nucleic acids, host cells, and the like, refers to materials which are found in nature.

The term "oligonucleotide" means a polynucleotide comprising 200 or fewer nucleotides. In some embodiments, oligonucleotides are 10 to 60 bases in length. In other embodiments, oligonucleotides are 10, 11, 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues (to form glycoproteins), or by phosphorylation. Polypeptides and proteins can be produced by a naturally-occurring and non-recombinant cell or by a genetically-engineered or recombinant cell, and can comprise molecules having the amino acid sequence of the native protein, or molecules having deletions from, additions to, and/or substitutions of one or more amino acids of the native sequence. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400 or 450 amino acids long.

A "recombinant protein", including a recombinant TTR protein, is a protein made using recombinant techniques, i.e., through the expression of a recombinant nucleic acid as described herein. Methods and techniques for the production of recombinant proteins are well known in the art.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

A "solid tumor" refers to an abnormal growth or mass of tissue that usually does not contain cysts or liquid areas. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors An antigen binding protein "specifically binds" to an antigen when the antigen binding protein exhibits demonstrates little to no binding to molecules other than the antigen. An antigen binding protein that specifically binds an antigen may, however, cross-react with antigens from different species. Typically, an antigen binding protein specifically binds an antigen when the dissociation constant ($K_D$) is $\leq 10^{-7}$ M as measured via a surface plasma resonance technique (e.g., BIACore, GE-Healthcare Uppsala, Sweden). An antigen binding protein specifically binds an antigen with "high affinity" when it binds with a $K_D \leq 5 \times 10^{-8}$ M, and with "very high affinity" when it binds with a $K_D$ is ≤5×10$^{-9}$ M (as measured using a method such as BIACore).

A "subject" or "patient" as used herein can be any mammal. In a typical embodiment, the subject or patient is a human.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "treating" refers to any indication of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat cancer and tumors, by, for instance, decreasing the progression or spreading of the cancer, inhibiting tumor growth, causing remission of the tumor and/or ameliorating a symptom associated with the cancer or tumor. Likewise, other methods provided herein treat infectious disease by decreasing the progression or spread of the infection, reducing the extent of the infection and/or ameliorating a symptom associated with the infection.

As used herein, the term "TTR," refers to "transthyretin." Human TTR is described in Mita et al., *Biochem. Biophys. Res. Commun.*, 124(2):558-564 (1984), which is incorporated herein by reference. The amino acid sequence for human TTR is also described in the UniProt Knowledgebase (www.uniprot.org/uniprot/P02766 #sequences) and is recited herein as SEQ ID NO: 43. The nucleic acid sequence for human TTR is also described at NCBI (www.ncbi.nlm.nih.gov/gene/7276). See also GenBank deposit K02091.1. The amino acid and nucleic acid sequences of murine TTR are set forth in SEQ ID NOs: 3 and 4, respectively.

The term "TTR variant" refers to a protein having an amino acid sequence which is at least 80%, 85%, 90%, 91%, 92%, 93%, 94%, 95%, 96%, 97%, 98%, or 99% identical to TTR having SEQ ID NO: 1. The present invention also includes nucleic acids encoding such TTR variants. Specific variants include, for example, TTR proteins with truncations at the C- or N-terminus.

A "tumor" refers to the mass of tissue formed as cancerous cells grow and multiply, which can invade and destroy normal adjacent tissues. Cancer cells can break away from a malignant tumor and enter the bloodstream or lymphatic system, such that cancer cells spread from the primary tumor to form new tumors in other organs.

A "variant" of a polypeptide comprises an amino acid sequence wherein one or more amino acid residues are inserted into, deleted from and/or substituted into the amino acid sequence relative to another polypeptide sequence. Variants include fusion proteins.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (e.g., replication defective retroviruses, adenoviruses and adeno-associated viruses), which serve equivalent functions.

Homodimer Fusion Proteins

As described herein, the present invention relates in part to the use of TTR in the multimerization of antigen binding proteins, such as antibodies. Because TTR is a human extracellular protein found in human serum, it is present in relatively high amounts throughout the human body. Thus, it is less likely to elicit an immune response when present in the multimerization constructs of the present invention when compared to, e.g., non-human, intracellular and rare proteins. Accordingly, its use in in the multimerization techniques of the present invention is advantageous.

For example, TTR can be used in the dimerization of antibodies. In such homodimer fusion proteins, TTR (SEQ ID NO: 1), or a variant thereof, is present as a tetramer wherein a TTR subunit is linked to the C-terminus of an antibody heavy chain to form TTR antibody homodimers. For example, the C-terminus of each antibody heavy chain (with each antibody containing two such C-termini) may be linked to the N-terminus of each TTR subunit (see FIG. 1a). Thus, each antibody is linked to two TTR subunits in the TTR tetramer, yielding a TTR antibody homodimer.

Accordingly, the present invention relates to homodimer fusion proteins comprising two antigen binding proteins. In some embodiments, the homodimer fusion proteins comprise antigen binding proteins linked to a protein complex. In some embodiments, the protein complex is a TTR protein complex, wherein the TTR protein complex is a TTR tetramer. In some embodiments the antigen binding protein is an antibody.

In particular embodiments, the present invention relates to homodimer fusion proteins comprising two antibodies linked to a TTR tetramer. The antibodies may be connected to the TTR tetramer without a linker (i.e., the antibodies are directly connected to the TTR).

In other embodiments, the antibodies are connected to the TTR tetramer via a linker. For example, amino acid linkers may be used to link the C-terminus of the antibody heavy chain to the TTR subunit N-terminus. In some embodiments, the linker is 1-5, 1-10, 1-15, 1-20, 1-25, 1-30, 1-35, or 1-40 amino acids in length. In some embodiments, the linker is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length. In other embodiments, the linker is 0, 1, 5, 10, 15, 20, 25, 30, 35, or 40 amino acids in length. In other embodiments, the linker is up to 5, 10, 15, 20, 25, 30, 35, or 40 amino acids in length. In some embodiments, the linker is up to 5, 10, 15, or 20 amino acids in length. In particular embodiments, the linker is 0, 5, 10, 15, or 20 amino acids in length.

In some embodiments, the linker is GGGGS(SEQ ID NO: 47), GGGGSGGGGS (i.e., (GGGGS)$_2$) (SEQ ID NO: 48), GGGGSGGGGSGGGGS (i.e., (GGGGS)$_3$) (SEQ ID NO: 49), GGGGSGGGGSGGGGSGGGGS (i.e., (GGGGS)$_4$) (SEQ ID NO: 50), GGGGSGGGGSGGGGSGGGGSGGGGS (i.e., (GGGGS)$_5$) (SEQ ID NO: 51), or GGGGSGGGGSGGGGSGGGGSGGGGSGGGGS (i.e., (GGGGS)$_6$ (SEQ ID NO: 52)). In other linker embodiments, the linker is GGGGS (SEQ ID NO: 47), GGGGSGGGGS (i.e., (GGGGS)$_2$) (SEQ ID NO: 48), GGGGSGGGGSGGGGS (i.e., (GGGGS)$_3$) (SEQ ID NO: 49), or GGGGSGGGGSGGGGSGGGGS (i.e., (GGGGS)$_4$) (SEQ ID NO: 50).

Other suitable amino acid linkers include, for example, disulfide bonds, (Gly)$_n$ (n=1-10), (EAAAK)$_n$ (n=1-5) (SEQ ID NO: 53), A(EAAAK)$_4$ALEA(EAAAK)$_4$A (SEQ ID NO: 54), PAPAP (SEQ ID NO: 55), AEAAAKEAAAKA (SEQ ID NO: 56), (Ala-Pro)$_n$ (n=1-20), VSQTSKLTRA-ETVFPDV (SEQ ID NO:57), PLGLWA (SEQ ID NO:58), RVLAEA (SEQ ID NO: 59), EDVVCCSMSY (SEQ ID NO: 60), GGIEGRGS (SEQ ID NO: 61), TRHRQPRGWE (SEQ ID NO: 62), AGNRVRRSVG (SEQ ID NO: 63), RRRRRRRRR (SEQ ID NO: 64), GFLG (SEQ ID NO: 65), and LE. Suitable non-amino acid linkers include polyethylene glycol (PEG).

In some embodiments, the antibodies are connected to a truncated TTR subunit, with or without a linker. For example, 1, 2, 3, 4, 5, 6, 7, 8, 9, or 10 amino acids may be removed from the N-terminus of one or more TTR subunits, and the antibody may be attached to the truncated TTR subunit N-terminus.

The present invention also relates to nucleic acid molecules encoding the homodimer fusion proteins described herein. Details regarding exemplary methods for producing the homodimer fusion proteins can be found in the Examples.

Tetramerization of Antibodies and Fabs

As described herein, the present invention relates in part to the use of TTR in the multimerization of antigen binding proteins, such as antibodies. As discussed above, the use of TTR in the multimerization techniques of the present invention is advantageous because TTR is less likely to elicit an immune response when present in the multimerization constructs of the present invention when compared to, e.g., non-human, intracellular and rare proteins.

The present invention also relates in part to the use of TTR in the tetramerization of antigen binding proteins, such as antibodies. In such homotetramer fusion proteins, TTR (SEQ ID NO: 1), or a variant thereof, is again present as a tetramer. However, in the context of the TTR antibody homotetramers, a single antibody heavy chain (i.e., only one of the two heavy chains present in a single antibody) is linked to each TTR subunit, allowing for the linkage of four antibodies to the TTR tetramer (see FIG. 1*b*). One of the two heavy chains of the antibody C-terminus may be linked to the N-terminus of each TTR subunit (see FIG. 1*b*). Thus, each antibody is linked to one TTR subunit in the TTR tetramer, yielding a TTR antibody homotetramer.

In such homotetramer fusion proteins, the formation of Fc homodimers (discussed above) is disfavored through mutations in the Fc. Such modifications include Fc mutations such as knobs-into-holes, DuoBodies, Azymetric, charge pair, HA-TF, SEEDbody, and modifications with differential protein A affinity. See, e.g., Spiess et al., Molecular Immunology, 67(2, Part A), 2015, pp. 95-106. Knobs-into-holes mutations include T366W in the first heavy chain, and T366S, L368A, and/or Y407V in the second heavy chain. See, e.g., Ridgway et al., Protein Eng., 9 (1996), pp. 617-621; and Atwell et al., J. Mol. Biol., 270 (1997), pp. 26-35. DuoBody mutations include F405L in the first heavy chain and K409R in the second heavy chain. See, e.g., Labrijn et al., Proc. Natl. Acad. Sci. U.S.A., 110 (2013), pp. 5145-5150. Azymetric mutations include T350V, L351Y, F405A, and/or Y407V in the first heavy chain, and T350V, T366L, K392L, and/or T394W in the second heavy chain. See, e.g., Von Kreudenstein et al., mAbs, 5 (2013), pp. 646-654. HA-TF mutations include S364H and/or F405A in the first heavy chain, and Y349T and/or T394F in the second heavy chain. See, e.g., Moore et al., mAbs, 3 (2011), pp. 546-557. SEEDbody mutations include IgG/A chimera mutations in the first heavy chain and IgG/A chimera mutations in the second heavy chain. See, e.g., Davis et al., Protein Eng. Des. Sel., 23 (2010), pp. 195-202. Differential protein A affinity mutations include H435R in one heavy chain and no mutations in the other heavy chain. See, e.g., U.S. Pat. No. 8,586,713. Each of these documents is incorporated by reference in its entirety.

In particular embodiments, it is possible to drive homotetramerization of the antibodies through the use of Fc charge pairs which disfavor homodimerization of the antibody heavy chains, thus favoring heavy chain heterodimerization between one antibody heavy chain which is linked to a TTR subunit and one antibody heavy chain that is not linked to a TTR (see FIG. 1*b*). For example, a set of charged mutations may be incorporated in the $C_H3$ domain of the heavy chain with either negative charges on one heavy chain and positive charges on the corresponding heavy chain, or a mixture of negative and positive charges on one heavy chain which pair with their corresponding positive and negative charges on the corresponding heavy chain. Exemplary negative charges include K392D & K409D and exemplary positive charges include E356K & D399K. Since like charges at the $C_H3$ interface repel while dissimilar charges attract, homodimerization is disfavored while heterodimerization is favored. TTR is fused to the heavy chain of only one charge type (either positive or negative, but not both); thus, resulting in one TTR subunit per full antibody composed of 4 chains (two light chains, one unfused heavy chain and one TTR fused heavy chain). Additional charge pair mutations are discussed in, for example, U.S. Pat. No. 9,546,203. Charge pair mutations including D221E, P228E, and/or L368E in the first heavy chain and D221R, P228R, and/or K409R in the second heavy chain are also described in, e.g, Strop et al., J. Mol. Biol., 420 (2012), pp. 204-219. Each of these documents is incorporated by reference in its entirety.

The present invention also relates in part to the use of TTR in the tetramerization of Fab fragments. In such homotetramer fusion proteins, TTR (SEQ ID NO: 1), or a variant thereof, is again present as a tetramer wherein each TTR subunit is linked to the C-terminus of each Fab fragment to form TTR Fab homotetramers (see FIG. 1*c*). Thus, each Fab fragment antibody is linked to a single TTR subunit in the TTR tetramer, yielding a TTR Fab homotetramer.

Accordingly, the present invention relates to homotetramer fusion proteins comprising four antigen binding proteins (e.g., a Fab tetramer) or eight antigen binding proteins (e.g., an Ab tetramer). In some embodiments, the homotetramer fusion proteins comprise antigen binding proteins linked to a protein complex. In some embodiments, the protein complex is a TTR protein complex, wherein the TTR protein complex is a TTR tetramer. In some embodiments the antigen binding protein is an antibody. In other embodiments the antigen binding protein is a Fab fragment.

In particular embodiments, the present invention relates to homotetramer fusion proteins comprising four antibodies linked to a TTR tetramer. In other embodiments, the present invention relates to homotetramer fusion proteins comprising four Fab fragments linked to a TTR tetramer. In some embodiments, the antibodies or Fabs are connected to the TTR tetramer without a linker (i.e., the antibodies or Fabs are directly connected to the TTR).

In other embodiments, the antibodies or Fabs are connected to the TTR tetramer via a linker. For example, amino acid linkers may be used to link the C-terminus of the antibody heavy chain to the TTR subunit N-terminus. In some embodiments, the linker is 1-5, 1-10, 1-15, 1-20, 1-25, 1-30, 1-35, or 1-40 amino acids in length. In some embodiments, the linker is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length. In other embodiments, the linker is 0, 1, 5, 10, 15, 20, 25, 30, 35, or 40 amino acids in length. In other embodiments, the linker is up to 5, 10, 15, 20, 25, 30, 35, or 40 amino acids in length. In some embodiments, the linker is up to 5, 10, 15, or 20 amino acids in length. In particular embodiments, the linker is 0, 5, 10, 15, or 20 amino acids in length.

In some embodiments, the linker is GGGGS (SEQ ID NO: 47), GGGGSGGGGS (i.e., (GGGGS)$_2$) (SEQ ID NO: 48), GGGGSGGGGSGGGGS (i.e., (GGGGS)$_3$) (SEQ ID NO: 49), GGGGSGGGGSGGGGSGGGGS (i.e., (GGGGS)$_4$) (SEQ ID NO: 50), GGGGSGGGGSGGGGSGGGGSGGGGS (i.e., (GGGGS)$_5$) (SEQ ID NO: 51), or GGGGSGGGGSGGGGSGGGGSGGGGSGGGGS (i.e., (GGGGS)$_6$) (SEQ ID NO: 52). In other linker embodiments, the linker is GGGGS(SEQ ID NO: 47), GGGGSGGGGS (i.e., (GGGGS)$_2$) (SEQ ID NO: 48), GGGGSGGGGSGGGGS (i.e., (GGGGS)$_3$) (SEQ ID NO: 49), or GGGGSGGGGSGGGGSGGGGS (i.e., (GGGGS)$_4$) (SEQ ID NO: 50).

Other suitable amino acid linkers include, for example, disulfide bonds, (Gly)$_n$ (n=1-10), (EAAAK)$_n$ (n=1-5), A(EAAAK)$_4$ALEA(EAAAK)$_4$A (SEQ ID NO: 54), PAPAP (SEQ ID NO: 55), AEAAAKEAAAKA (SEQ ID NO: 56), (Ala-Pro)$_n$ (n=1-20), VSQTSKLTRAETVFPDV (SEQ ID NO: 57), PLGLWA (SEQ ID NO: 58), RVLAEA (SEQ ID NO: 59), EDVVCCSMSY (SEQ ID NO: 60), GGIEGRGS (SEQ ID NO: 61), TRHRQPRGWE (SEQ ID NO: 62), AGNRVRRSVG (SEQ ID NO: 63), RRRRRRRRR (SEQ ID NO: 64), GFLG (SEQ ID NO: 65), and LE. Suitable non-amino acid linkers include polyethylene glycol (PEG) and triazine-containing moieties (contained within constructs having a terminal group capable of reacting with a protein; see, for example PCT publication No. WO/2017/083604 which is hereby incorporated by reference in its entirety).

In some embodiments, the antibodies or Fabs are connected to a truncated TTR subunit, with or without a linker. For example, 1, 2, 3, 4, 5, 6, 7, 8, 9, or 10 amino acids may be removed from the N-terminus of one or more TTR subunits, and the antibodies or Fabs may be attached to the truncated TTR subunit N-terminus.

The present invention also relates to nucleic acid molecules encoding the homodimer fusion proteins described herein. Details regarding exemplary methods for producing the homotetramer (TTR and Ab) fusion proteins can be found in the Examples.

Antigen Binding Proteins

Any antigen binding protein (e.g., Fab or antibody) can be used in the TTR fusion proteins of the present invention. Because the fusion proteins of the present invention allow for antigen binding protein multimerization, antigen binding proteins that target/bind antigens wherein antigen binding protein clustering or avidity is needed for activity may particularly benefit from the fusion proteins of the present invention. Accordingly, in some embodiments, the antigen binding proteins (e.g., antibodies or Fabs) target/bind to: 4-1BB (CD137), CD20, GITR, DR5, OX40 (CD134), ICOS (CD278), or CD27. Such proteins/targets have been shown to play a role in cancer pathways. In other embodiments, the antigen binding proteins (e.g., antibodies or Fabs) target/bind to: ErbB-1 (epidermal growth factor receptor (EGFR)), ErbB-2 (HER2 in humans and neu in rodents), ErbB-3 (HER3), ErbB-4 (HER4), FGFR (fibroblast growth factor receptor), VEGFR (vascular endothelial growth factor), RET protein products, EGFR, KIT protein products, Abl (Abelson murine leukemia viral oncogene homolog 1), Raf (Rapidly Accelerated Fibrosarcoma) kinases, or PDGFR (platelet-derived growth factor receptors).

In one embodiment, the antigen binding protein (e.g., antibody or Fab) specifically binds to CB1R (anti-cannabinoid receptor-1; gene name Cnr1). The CB1 receptor is a Gi-coupled G-Protein Receptor that is widely expressed in the CNS and peripheral nervous system. Agonist stimulation of CB1 receptors leads to inhibition of adenylyl cyclase activity and activation of mitogen-activated protein (MAP) kinase. Endogenous agonists of the CB1 receptor can comprise anandamide and arachidonoyl glycerol. Exogenous agonists can comprise A9-tetrahydrocannabinol. Antagonists or inverse agonists have been shown to reduce body weight and improve metabolic parameters, e.g., reduced plasma glucose and insulin levels. Thus, in particular embodiments, the antigen binding portion of the TTR fusion protein is an anti-CB1R antibody (e.g., the anti-CB1R antibody 10D10 having heavy chain SEQ ID NO: 5, and light chain SEQ ID NO: 11; or an anti-CB1R antibody having heavy chain SEQ ID NO: 6 or 7, and light chain SEQ ID NO: 11). In other particular embodiments, the antigen binding protein of the TTR fusion protein is an anti-CB1R Fab (e.g., a Fab derived from 10D10 such as Fab heavy chain SEQ ID NO:44, and Fab light chain SEQ ID NO: 11). See, e.g., US patent publication 20160145333, which is hereby incorporated by reference.

In one embodiment, the antigen binding protein (e.g., antibody or Fab) specifically binds to GITR (glucocorticoid-induced TNFR-related protein; TNFRSF18). GITR, sometimes also referred to as Activation-Inducible TNFR family member (AITR), is a receptor belonging to the TNF receptor superfamily (TNFRSF). It is activated by its cognate ligand, GITR ligand (GITRL, TNFSF18). GITR is a type I transmembrane protein that contains a cysteine-rich extracellular domain, which is characteristic of TNFR family members. The cytoplasmic domain of GITR, for instance, shares close homology with certain other TNFR family members, such as 4-1BB and CD27 (Nocentini, et al. (1997) Proc. Natl. Acad. Sci. 94:6216-6221, which is hereby incorporated by reference). GITR activation results in an enhanced immune response and such activation has the potential to restore immune responses to infections and to tumors. Accordingly, molecules capable of activating GITR may be useful as immunostimulatory agents in settings in which it is desirable to trigger an enhanced immune response. Thus, in particular embodiments, the antigen binding portion of the TTR fusion protein is an anti-GITR antibody (e.g., the anti-GITR antibody 9H6 having heavy chain SEQ ID NO: 18, and light chain SEQ ID NO: 25; or an anti-GITR antibody having heavy chain SEQ ID NO: 19 or 20, and light chain SEQ ID NO: 25). In other particular embodiments, the antigen binding protein of the TTR fusion protein is an anti-GITR Fab (e.g., a Fab derived from 9H6 such as Fab heavy chain SEQ ID NO: 21, and Fab light chain SEQ ID NO: 26). See, e.g., US patent publication 20150064204, which is hereby incorporated by reference.

In one embodiment, the antigen binding protein (e.g., antibody or Fab) specifically binds to TRAILR2 (TRAIL receptor 2; also referred to as DR5 (death receptor 5)). The interaction between TR-2 (tumor necrosis factor (TNF)-related apoptosis-inducing ligand ("TRAIL") Receptor-2) and its ligand, TRAIL, plays a role in the induction of apoptosis (see, for example, Almasan et al., Cytokine & Growth Factor Reviews 14: 337-348 (2003)). TRAIL, also known as Apo2 ligand, is a homomeric ligand that interacts with four members of the TNF-receptor superfamily (TRAIL receptors ("TR") 1 to 4), as well as with the related, soluble, opsteoprotegerin ("OPG") receptor. Binding of TRAIL to TR-1 or TR-2 at the surface of a cell triggers apoptosis of that cell. After initial binding of TRAIL to TR-1 or TR-2, intracellular proteins are recruited to the intracellular death domain of the receptor, forming a signaling complex. Certain intracellular caspases are recruited to the complex; where they autoactivate and in turn activate additional caspases and the intracellular apoptosis cascade. TR-3 and TR-4 and OPG lack the intracellular domain responsible for transmitting the apoptosis signal. Thus, binding of TRAIL to TR-3, TR-4, or OPG does not trigger apoptosis. TR-3 and TR-4 are also referred to as "decoy" receptors, and their overexpression has been shown to protect cells from apoptotic induction by TRAIL. TR-2 is expressed in a variety of cells, including liver, brain, breast, kidney, colon, lung, spleen, thymus, peripheral blood lymphocytes, prostate, testis, ovary, uterus, and various tissues along the gastro-intestinal tract. (See, for example, Walczak et al., EMBO J. 16: 5386-5397 (1997); Spierings et al., J. Histochem. Cytochem. 52: 821-831 (2004), each of which is incorporated herein by reference). Though TRAIL and TRAIL receptors are widely expressed, they are most active in inducing apoptosis in transformed cells. (See, for example, Daigle et al., Swiss Med. Wkly. 131: 231-237 (2001), which is hereby incorporated by reference). Conatumumab, an anti-TRAILR2 monoclonal antibody, has been in development for the treatment of cancer. Thus, in particular embodiments, the antigen binding portion of the TTR fusion protein is an anti-TRAILR2 antibody (e.g., conatumumab having heavy chain SEQ ID NO: 31, and light chain SEQ ID NO: 38; or an anti-TRAILR2 antibody having heavy chain SEQ ID NO: 32 or 33, and light chain SEQ ID NO: 38)). In other particular embodiments, the antigen binding protein of the TTR fusion protein is an anti-TRAILR2 Fab (e.g., a Fab derived from conatumumab such as Fab heavy chain SEQ ID NO: 34, and Fab light chain SEQ ID NO: 39).

TTR Variants

As discussed above, TTR variants may also be used in the present invention. Any of the TTR variants discussed herein may be utilized in combination with each other. TTR variants include proteins having an amino acid sequence which is at least 80%, 81%, 82%, 83%, 86%, 85%, 86%, 87%, 88%, 89%, 90%, 91%, 92%, 93%, 94%, 95%, 96%, 97%, 98%, or 99% identical to a TTR protein having, e.g., SEQ ID NO: 1, SEQ ID NO: 3, or SEQ ID NO: 43.

In some embodiments, the TTR of the present invention comprises the amino acid sequence of human TTR SEQ ID NO: 43. In a particular embodiment, the TTR of the present invention comprises the amino acid sequence of SEQ ID NO: 43 with mutations at K15, C10, or both K15/C10 (e.g., K15A, C10A, or both K15A/C10A). In specific embodiments, the TTR of the present invention comprises both the K15A and C10A mutations and, thus, has the amino acid sequence of SEQ ID NO: 1.

Cysteines present in human TTR (e.g., SEQ ID NO: 1 or SEQ ID NO: 43) may be used as sites of conjugation to antigen binding proteins (e.g., antibodies and Fabs). In addition, TTR variants that enable site specific conjugation, such as TTR variants with engineered cysteines, may be used in the present invention. See, e.g., U.S. Pat. No. 8,633,153, which is hereby incorporated by reference. For example, a TTR variant may include one or more of the following cysteine mutations: A37C, D38C, A81C, or G83C.

Additional variants useful in the present invention include, for example, TTR proteins with truncations at the C- or N-terminus. Such TTR proteins include those wherein 1, 2, 3, 4, 5, 6, 7, 8, 9, 10, 11, 12, 13, 14, 15, 16, 17, 18, 19, or 20 amino acids are removed from the C- or N-terminus TTR protein. In some embodiments, the fusion proteins of the present invention comprise TTR proteins wherein 1, 2, 3, 4, 5, 6, 7, or 8 amino acids are removed from the C- or N-terminus of the TTR protein. In other embodiments, the fusion proteins of the present invention comprise TTR proteins wherein 1, 2, 3, 4, 5, 6, 7, or 8 amino acids are removed from the N-terminus of the TTR protein.

Additional TTR variants that can be used in the present invention include those which reduce or block TTR binding to thyroxine. Each TTR tetramer contains two thyroxine binding sites located in the central channel of the TTR tetramer. Such variants, for example, could avoid interference with thyroxine biology in patients and may avoid having TTR fusions acted upon by the thyroxine metabolism path. Yet other TTR variants that can be used in the present invention include those that reduce or eliminate the proteolytic activity of TTR.

In addition, TTR-His tag fusions may be used in the present invention. For example, TTR-His tag fusions may be used in the purification of TTR Fab constructs wherein the Fab lacks an Fc, or for the purification of TTR Ab constructs where it is beneficial to avoid the low pH purification environment of a Protein A affinity column. In some embodiments, the His tag is removed after purification. His tags may also be present in the final therapeutic molecule (i.e., the tag may be retained after purification). In some embodiments, the His tag is a His, $(His)_2$, $(His)_3$, $(His)_4$ (SEQ ID NO: 66), $(His)_5$ (SEQ ID NO: 67), $(His)_6$ (SEQ ID NO: 68), $(His)_7$ (SEQ ID NO: 69), $(His)_8$ (SEQ ID NO: 70), $(His)_9$ (SEQ ID NO: 71), or $(His)_{10}$ (SEQ ID NO: 72) tag. In particular embodiments, the His tag is a $(His)_6$ (SEQ ID NO:

68) or (His)₇ (SEQ ID NO: 69) tag. In a specific embodiment, the His tag is a (His)₆ tag. In some embodiments, the His tag includes 1, 2, 3, 4, 5, 6, 7, 8, 9, or 10 glycine amino acids as a linker. In a particular embodiment, the His tag includes two glycines (e.g., GGHHHHHHH (SEQ ID NO:30)).

In some embodiments, a two glycine amino acid linker can be inserted between the TTR variant and the heavy or light chain.

Moreover, the TTR variant of the present invention may include variants incorporating glycosylation sites which may be helpful in modulating the PK or solubility properties of the TTR fusions. In addition, the TTR variants or TTR fusion proteins of the present invention may modified to include moieties which confer beneficial PK properties, e.g., triazine-containing moieties (contained within constructs having a terminal group capable of reacting with a protein; see, for example PCT publication No. WO/2017/083604 which is hereby incorporated by reference in its entirety).

Methods of Making Homodimer and Homotetramer Fusion Proteins

Methods of making the homodimer and homotetramer fusions of the present invention are discussed in the Examples.

Generally, the homodimer and homotetramer fusions of the present invention can be generated using recombinant methods. Accordingly, the present invention includes polynucleotides encoding the homodimer and homotetramer fusions. In another aspect the present invention comprises an expression vector comprising the polynucleotide encoding the homodimer and homotetramer fusion. In certain embodiments, the expression vectors comprise control sequences (e.g., promoters, enhancers) that are operably linked to a polynucleotide encoding the homodimer and homotetramer fusion so as support expression in a suitable host cell. In certain embodiments, the expression vector also comprises polynucleotide sequences that allow chromosome-independent replication in the host cell. Exemplary vectors include, but are not limited to, plasmids, cosmids, and YACS. In a particular embodiment, the vector is pTT5.

Generally, mammalian host cells are utilized when generating the Ab TTR homodimer or Ab TTR homotetramer fusion constructs. Mammalian host cells are also suitable for generating Fab TTR homotetramer fusion constructs, though non-mammalian cells such as prokaryotic (bacteria) and non-mammalian (e.g., yeast) host cells may also be used.

In yet another aspect, the invention comprises a host cell comprising the expression vector of the invention. Methods of transfecting host cells with the expression vector and culturing the transfected host cells under conditions suitable for expression of the homodimer and homotetramer fusions are known in the art. The transfection procedure used may depend upon the host to be transformed. Certain methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei. Certain mammalian cell lines available as hosts for expression are known in the art and include, but are not limited to, many immortalized cell lines available from the American Type Culture Collection (ATCC), including but not limited to Chinese hamster ovary (CHO; e.g., CHO-K1) cells, E5 cells, baby hamster kidney (BHK) cells, monkey kidney cells (COS), human hepatocellular carcinoma cells (e.g., Hep G2), human embryonic kidney cells 293 (HEK 293), and a number of other cell lines. In certain embodiments, cell lines may be selected through determining which cell lines have high expression levels and produce the homodimer and homotetramer fusions.

Thus, the present invention also relates to methods of making the homodimer and homotetramer fusion proteins described herein. For example, the homodimer and homotetramer fusion proteins may be made by:
 a) culturing a recombinant host cell comprising a polynucleotide encoding the homodimer and homotetramer fusion; and
 b) isolating the homodimer or homotetramer fusion protein from said culture.

Pharmaceutical Compositions

In some embodiments, the invention provides a pharmaceutical composition comprising a therapeutically effective amount of one or more of the homomultimer fusion proteins of the present invention (e.g., TTR antibody homodimer, TTR antibody homotetramer, or TTR Fab homotetramer fusion proteins) together with a pharmaceutically effective diluent, carrier, solubilizer, emulsifier, preservative, and/or adjuvant. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of a homomultimer fusion proteins (e.g., TTR antibody homodimer, TTR antibody homotetramer, or TTR Fab homotetramer fusion proteins) are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMA- CEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, homomultimer compositions (e.g., a TTR antibody homodimer, TTR antibody homotetramer, or TTR Fab homotetramer fusion protein) may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the homomultimer (e.g., a TTR antibody homodimer, TTR antibody homotetramer, or TTR Fab homotetramer fusion protein) may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired homomultimer (e.g., a TTR antibody homodimer, TTR antibody homotetramer, or TTR Fab homotetramer fusion protein) in a pharmaceutically acceptable vehicle. A particularly suitable vehicle for parenteral injection is sterile distilled water in which the homomultimer (e.g., a TTR antibody homodimer, TTR antibody homotetramer, or TTR Fab homotetramer fusion protein) is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, homomultimers (e.g., TTR antibody homodimer, TTR antibody homotetramer, or TTR Fab homotetramer fusion proteins) are advantageously formulated as a dry, inhalable powder. In specific embodiments, homomultimer (e.g., a TTR antibody homodimer, TTR antibody homotetramer, or TTR Fab homotetramer fusion protein) inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Homomultimers (e.g., TTR antibody homodimer, TTR antibody homotetramer, or TTR Fab homotetramer fusion proteins) that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the homomultimer (e.g., a TTR antibody homodimer, TTR antibody homotetramer, or TTR Fab homotetramer fusion protein). Diluents, flavorings, low melting point waxes, vegetable oils, lubricants, suspending agents, tablet disintegrating agents, and binders may also be employed.

Additional pharmaceutical compositions will be evident to those skilled in the art, including formulations involving homomultimers (e.g., TTR antibody homodimer, TTR antibody homotetramer, or TTR Fab homotetramer fusion proteins) in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(–)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering homomultimer (e.g., a TTR antibody homodimer, TTR antibody homotetramer, or TTR Fab homotetramer fusion protein) formulations, which can be used as pharmaceutical compositions, as described in international patent application WO 06138181A2 (PCT/US2006/022599), which is incorporated by reference in its entirety herein.

As discussed above, certain embodiments provide homomultimer (e.g., a TTR antibody homodimer, TTR antibody homotetramer, or TTR Fab homotetramer fusion protein) compositions, particularly pharmaceutical homomultimer (e.g., a TTR antibody homodimer, TTR antibody homotetramer, or TTR Fab homotetramer fusion protein) compositions, that comprise, in addition to the homomultimer (e.g., a TTR antibody homodimer, TTR antibody homotetramer, or TTR Fab homotetramer fusion protein), one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in homomultimer (e.g., a TTR antibody homodimer, TTR antibody homotetramer, or TTR Fab homotetramer fusion protein) formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the homomultimer (e.g., a TTR antibody homodimer, TTR antibody homotetramer, or TTR Fab homotetramer fusion protein) formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of homomultimer (e.g., a TTR antibody homodimer, TTR antibody homotetramer, or TTR Fab homotetramer fusion protein) formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the homomultimer (e.g., a TTR antibody homodimer, TTR antibody homotetramer, or TTR Fab homotetramer fusion protein) formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

Homomultimer (e.g., a TTR antibody homodimer, TTR antibody homotetramer, or TTR Fab homotetramer fusion protein) formulations generally will be designed for specific routes and methods of administration, for specific administration dosages and frequencies of administration, for specific treatments of specific diseases, with ranges of bioavailability and persistence, among other things. Formulations thus may be designed in accordance with the invention for delivery by any suitable route, including but not limited to orally, aurally, opthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of a homomultimer-containing (e.g., a TTR antibody homodimer-containing, TTR antibody homotetramer-containing, or TTR Fab homotetramer-containing fusion protein) pharmaceutical composition to be employed will depend, for example, upon the therapeutic context and objectives. One skilled in the art will appreciate that the appropriate dosage levels for treatment will vary depending, in part, upon the molecule delivered, the indication for which the homomultimer (e.g., a TTR antibody homodimer, TTR antibody homotetramer, or TTR Fab homotetramer fusion protein) is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of a homomultimer (e.g., a TTR antibody homodimer, TTR antibody homotetramer, or TTR Fab homotetramer fusion protein) preferably results in a decrease in severity of disease symptoms, in an increase in frequency or duration of disease symptom-free periods, or in a prevention of impairment or disability due to the disease affliction.

Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163, all incorporated by reference herein.

Therapeutic Uses of Homodimer and Homotetramer Fusion Proteins

As illustrated in the Examples, it has been discovered that the dimerization of antibodies with TTR to generate TTR homodimer fusion proteins, as well as the tetramerization of antibodies and Fab fragments with TTR to generate TTR homotetramer fusion proteins, results in TTR-containing fusion proteins with increased avidity compared to the individual antibody(ies) and/or Fab fragment(s).

In addition, the TTR homodimer and TTR homotetramer fusion proteins demonstrate improved antigen clustering compared to the individual antibody(ies) and/or Fab fragment(s). When antibodies (e.g., IgG antibodies) bind antigens on target cells (e.g., tumor cells), the resulting clustered Fc domains engage with FcγR's found on immune effector cells such as NK cells and macrophages. This clustering aids in signaling through FcγR's resulting in the initiation of cell-mediated effector functions such as antibody-dependent cellular cytotoxicity (ADCC) and antibody-dependent cellular phagocytosis (ADCP). Thus, the TTR homodimer and TTR homotetramer fusion proteins are particularly useful in targeting ligands where high antibody or Fab affinity/avidity leads to an enhanced biological effect. Enhancement of cell-mediated effector functions by the TTR homodimer and TTR homotetramer constructs of the present invention results in an increased ability to kill cells which is useful, e.g., the treatment of cancer.

The TTR homodimer and TTR homotetramer fusion proteins of the present invention can be used to bind a variety of targets/antigens. For example, the TTR homodimer and TTR homotetramer fusion proteins can be used as agonists in targeting TRAIL, TRAIL2R. GITR, OX40, GLP1, TREM2, and 4-1BB. In addition, the TTR homodimer and TTR homotetramer fusion proteins can be used as antagonists in targeting GIPR, TNFR, integrin receptors, PD-1, PD-L1, TIGIT, LAG-3, and TIM-3.

Accordingly, the present invention also relates to methods of treating cancer using the homodimer fusion proteins and homotetramer fusion proteins described herein.

In other embodiments, the present invention relates to a use of the homodimer fusion proteins and homotetramer fusion proteins described herein in the treatment of cancer.

In yet other embodiments, the present invention relates to homodimer fusion proteins and homotetramer fusion proteins described herein for use in the treatment of cancer.

EXAMPLES

The following examples are provided for the purpose of illustrating specific embodiments or features of the present invention and are not intended to limit its scope.

Example 1: Summary of Generated TTR Antibody Homodimer, TTR Antibody Homotetramer, and TTR Fab Homotetramer Fusion Proteins Cloning of TTR Antibody Homodimer, TTR Antibody Homotetramer, and TTR Fab Homotetramer Fusion Proteins The following hybridoma derived antibodies and Fabs were used to generate fusion proteins:
    Anti-CB1R antibodies and Fabs from hybridoma CB10 (also referred to as hybridoma 10D10)
    Anti-GITR antibodies and Fabs from hybridoma 9H6
    The anti-TRAILR2 antibody conatumumab and the corresponding conatumumab Fab The following TTR fusion proteins were generated. [TTR]=the TTR tetramer. For simplicity, His tags (for Fab constructs) are not illustrated in the Example 1 summary.

Specifically, the following TTR antibody homodimer fusion proteins were constructed. In these constructs, the C-terminus of both antibody heavy chains was linked to the N-terminus of each TTR subunit.

a. [anti-CB1R antibodies]$_2$-[TTR]
        "CB1R TTR antibody homodimer fusion protein"
        Generated sequence pairs:

| TTR-Heavy Chain Fusion | Light Chain |
|---|---|
| [SEQ ID NO: 5]$_2$-[SEQ ID NO: 1]$_4$ | SEQ ID NO: 11 |
| [[SEQ ID NO: 5]-[GGGGS]]$_2$-[SEQ ID NO: 1]$_4$ | SEQ ID NO: 11 |
| [[SEQ ID NO: 5]-[(GGGGS)$_2$]]$_2$-[SEQ ID NO: 1]$_4$ | SEQ ID NO: 11 |
| [[SEQ ID NO: 5]-[(GGGGS)$_3$]]$_2$-[SEQ ID NO: 1]$_4$ | SEQ ID NO: 11 |
| [[SEQ ID NO: 5]-[(GGGGS)$_4$]]$_2$-[SEQ ID NO: 1]$_4$ | SEQ ID NO: 11 | b. [anti-GITR antibodies]$_2$-[TTR]
        "GITR TTR antibody homodimer fusion protein"
        Generated sequence pairs:

| TTR-Heavy Chain Fusion | Light Chain |
|---|---|
| [SEQ ID NO: 18]$_2$-[SEQ ID NO: 1]$_4$ | SEQ ID NO: 25 | c. [anti-TRAILR2 antibodies]$_2$-[TTR]
        "Conatumumab TTR antibody homodimer fusion protein"
        Generated sequence pairs:

| TTR-Heavy Chain Fusion | Light Chain |
|---|---|
| [SEQ ID NO: 31]$_2$-[SEQ ID NO: 1]$_4$ | SEQ ID NO: 38 |

In addition, the following TTR antibody homotetramer fusion proteins were constructed. In these constructs, one of the two heavy chains of the antibody C-terminus, containing charge pair mutations D399K and E356K (SEQ ID NO: 6, 19, or 32), was linked (with or without a linker) to the N-terminus of a TTR subunit. The remaining heavy chain containing a complimentary set of K392D and K409D charge pair mutations (SEQ ID NO: 7, 20, or 33) associated with the linked heavy chain. Note that, in the discussion of the constructs in the Examples, discussion of E416K and D459K refers to EU E356K and EU D399K, respectively. Similarly, in the discussion of the constructs in the Examples, discussion of K420D and K437D refers to EU K392D and EU K409D, respectively.

a. [anti-CB1R antibodies]$_4$-[TTR]
"CB1R TTR antibody homotetramer fusion protein"
Generated sequence pairs:

| TTR-Heavy Chain Fusion | Light Chain |
| --- | --- |
| [SEQ ID NO: 6]$_4$-[SEQ ID NO: 1]$_4$ and [SEQ ID NO: 7]$_4$ | SEQ ID NO: 11 |
| [[SEQ ID NO: 6]-[GGGGS]]$_4$-[SEQ ID NO: 1]$_4$ and [[SEQ ID NO: 7]$_4$ | SEQ ID NO: 11 | b. [anti-GITR antibodies]$_4$-[TTR]
"GITR TTR antibody homotetramer fusion protein"
Generated sequence pairs:

| TTR-Heavy Chain Fusion | Light Chain |
| --- | --- |
| [SEQ ID NO: 19]$_4$-[SEQ ID NO: 1]$_4$ and [SEQ ID NO: 20]$_4$ | SEQ ID NO: 25 | c. [anti-TRAILR2 antibodies]$_4$-[TTR]
"Conatumumab TTR antibody homotetramer fusion protein"
Generated sequence pairs:

| TTR-Heavy Chain Fusion | Light Chain |
| --- | --- |
| [SEQ ID NO: 32]$_4$-[SEQ ID NO: 1]$_4$ and [SEQ ID NO: 33]$_4$ | SEQ ID NO: 38 |

In addition, the following TTR Fab homotetramer fusion proteins were constructed. In these constructs, the C-terminus of each Fab fragment was linked to the N-terminus of each TTR subunit.

a. [anti-CB1R Fab]$_4$-[TTR]
"CB1R TTR Fab homotetramer fusion protein"
Note that, in the discussion of the constructs in the Examples, discussion of S215E refers to EU S183E. Similarly, in the discussion of the constructs in the Examples, discussion of S203K refers to EU S176K. In the [SEQ ID NO: 44]$_4$-[SEQ ID NO: 1]$_4$+SEQ ID NO: 11 fusion, no charge pair mutations were used. In the [SEQ ID NO: 45]$_4$-[SEQ ID NO: 1]$_4$ & SEQ ID NO: 46 fusion, SEQ ID NO: 45 contains the S215E charge pair mutation, and SEQ ID NO: 46 contains the charge pair S203K mutation, both numbered in accordance with the EU system.

Generated sequence pairs:

| TTR-Heavy Chain Fusion | Light Chain |
| --- | --- |
| [SEQ ID NO: 44]$_4$-[SEQ ID NO: 1]$_4$ SEQ ID NO: 44 | SEQ ID NO: 11 [SEQ ID NO: 11]$_4$-[SEQ ID NO: 1]$_4$ |
| [SEQ ID NO: 45]$_4$-[SEQ ID NO: 1]$_4$ SEQ ID NO: 45 | SEQ ID NO: 46 [SEQ ID NO: 46]$_4$-[SEQ ID NO: 1]$_4$ | b. [anti-GITR Fab]$_4$-[TTR]
"GITR TTR Fab homotetramer fusion protein"
Generated sequence pairs:

| TTR-Heavy Chain Fusion | Light Chain |
| --- | --- |
| [SEQ ID NO: 21]$_4$-[SEQ ID NO: 1]$_4$ | SEQ ID NO: 26 | c. [anti-TRAILR2 Fab]$_4$-[TTR]
"Conatumumab TTR Fab homotetramer fusion protein"
Generated sequence pairs:

| TTR-Heavy Chain Fusion | Light Chain |
| --- | --- |
| [SEQ ID NO: 34]$_4$-[SEQ ID NO: 1]$_4$ | SEQ ID NO: 39 |

For TTR antibody homodimer fusion proteins, the C-terminus of each antibody heavy chain was linked to the N-terminus of each TTR subunit. For TTR antibody homotetramer fusion proteins, one of the two heavy chains of the antibody C-terminus was linked to the N-terminus of each TTR subunit. For the TTR Fab homotetramer fusion proteins, the C-terminus of each Fab fragment was linked to the N-terminus of each TTR subunit.

The fusion proteins were generated using standard molecular biology techniques including polymerase chain reaction (PCR), site-directed PCR mutagenesis, restriction endonuclease digestion and enzymatic ligation into mammalian expression plasmids. Poly-histidine tagged Fab-TTR molecules, wherein the $(His)_6$ tag was added to the Fab C-terminus, were also generated.

The cloned TTR fused variant heavy chain and Fab DNAs in combination with their respective cloned anti-CB1, anti-GITR and anti-TR2 antibody light chain (LC) DNAs were used to transfect mammalian cells for the expression of the TTR antibody homodimer, TTR antibody homotetramer, and TTR Fab homotetramer fusion proteins. The techniques were generally performed according to methods that can be reference in *Molecular Cloning: A Laboratory Manual*, $3^{rd}$ ed., Sambrook et al., 2001, Cold Spring Harbor Laboratory Press, cold Spring Harbor, N.Y.

Example 2: Cloning, Expression, and Purification of Anti-CB1 TTR Antibody Homodimer, TTR Antibody Homotetramer, and TTR Fab Homotetramer Fusion Proteins Cloning of Anti-CB1 TTR Antibody Homodimer, TTR Antibody Homotetramer, and TTR Fab Homotetramer Fusion Proteins Anti-CB1 TTR antibody homodimers were generally cloned as follows. pTT5-del-Bsm-BI:VK1O2O12::[hu anti-<huCB1> 10D10.1 VH]::huIgG2TO (construct C59477) was used as a template for the constructs described below. The pTT5-del-Bsm-BI vector is a derivative of the pTT5 vector, where a BsmBI restriction site has been removed.

SEQ ID NO: 5]$_2$-[SEQ ID NO: 1]$_4$ was assembled as follows. PCR1: using C59477 as a template, a 5' PCR primer encoding the amino terminus of the signal sequence, a SalI restriction enzyme site, and an optimized Kozak sequence (5' AGT TTA AAC GAA TTC GTC GAC TAG GCC ACC ATG GAC ATG AGG GTG CC 3' (SEQ ID NO: 73), in combination with a 3' primer, designed to eliminate an existing BamHI restriction site within C59477, (5' GTG CTG GCG AAT CCA GCT CCA ATA GTC ACC 3' (SEQ ID NO: 74)). PCR1 resulted in an approximately 220 base pair product. PCR2a: using C59477 as template, a 5' PCR primer designed to eliminate an existing BamHI restriction site, (5' GAG CTG GAT TCG CCA GCA CCC AGG 3' (SEQ ID NO: 75), in combination with a 3' primer, encoding the carboxyl terminus human heavy chain constant region (CH3) and the amino terminus (5' GGT GCC CGT AGG GCC ACC CGG AGA CAG GGA G 3' (SEQ ID NO: 76)) of TTR (SEQ ID NO: 1). PCR2a resulted in an approximately 1250 base pair product. PCR3a: using TTR (SEQ ID NO: 1) as template, a 5' PCR primer encoding the carboxyl terminus human heavy chain constant region (CH3) and the amino terminus of TTR (5' TCC CTG TCT CCG GGT GGC CCT ACG GGC ACC G 3' (SEQ ID NO: 77)), in combination with a 3' primer, encoding the carboxyl terminus region of TTR (SEQ ID NO: 1), a termination codon and NotI restriction site, (5' AAC GAT ATC GCT AGC GCG GCC GCT CAT TCC TTG GGA TTG GTG 3' (SEQ ID NO: 78)). PCR3a resulted in an approximately 400 base pair product. PCR reactions 1, 2a and 3a were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73494: pTT15d:VK1O2O12::[hu anti-<huCB1> 10D10.1 (huIgG2-TO desK) VH]::TTR3.

[[SEQ ID NO: 5]-[GGGGS]]$_2$-[SEQ ID NO: 1]$_4$ was assembled using PCR1 as described above. PCR2b: using C59477 as template, a 5' PCR primer designed to eliminate an existing BamHI restriction site, (5' GAG CTG GAT TCG CCA GCA CCC AGG 3' (SEQ ID NO:75), in combination with a 3' primer, encoding the carboxyl terminus human heavy chain constant region (CH3), a G4S linker, and the amino terminus (5' GGA TCC GCC ACC ACC ACC CGG AGA CAG GGA G 3' (SEQ ID NO:79) of TTR (SEQ ID NO: 1). PCR2b resulted in an approximately 1250 base pair product. PCR3b:, using TTR (SEQ ID NO: 1) as template, a 5' PCR primer encoding the carboxyl terminus human heavy chain constant region (CH3), a G4S linker and the amino terminus (5' GGT GGT GGT GGC GGA TCC GGC CCT ACG GGC ACC G 3' (SEQ ID NO: 80) of TTR, in combination with a 3' primer, encoding the carboxyl terminus region of TTR, a termination codon and NotI restriction site, (5' AAC GAT ATC GCT AGC GCG GCC GCT CAT TCC TTG GGA TTG GTG 3'(SEQ ID NO: 78)). PCR3b resulted in an approximately 400 base pair product. PCR reactions 1, 2b and 3b were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73499: pTT15d:VK1O2O12::[hu anti-<huCB1> 10D10.1 (huIgG2-TO desK) VH]::G4S::TTR3.

[[SEQ ID NO: 5]-[(GGGGS)$_2$]]$_2$-[SEQ ID NO: 1]$_4$ was assembled using PCR1 as described above. PCR2c: using C59477 as template, a 5' PCR primer designed to eliminate an existing BamHI restriction site, (5' GAG CTG GAT TCG CCA GCA CCC AGG 3' (SEQ ID NO:75)) in combination with a 3' primer, encoding the carboxyl terminus human heavy chain constant region (CH3), a (GGGGS)$_2$ (SEQ ID NO: 48) linker, and the amino terminus (5' GCC GGA CCC TCC CCC ACC GGA TCC GCC ACC TCC ACC CGG AGA CAG GGA G 3' (SEQ ID NO:81)) of TTR (SEQ ID NO: 1). PCR2c resulted in an approximately 1250 base pair product. PCR3c: using TTR as template, a 5' PCR primer encoding the carboxyl terminus human heavy chain constant region (CH3), a (GGGGS)$_2$ (SEQ ID NO:48) linker and the amino terminus of TTR (5' CCG GTG GGG GAG GGT CCG GCC CTA CGG GCA CCG GTG AAT CCA AGG CTC CT 3' (SEQ ID NO: 82)), in combination with a 3' primer, encoding the carboxyl terminus region of TTR, a termination codon and NotI restriction site, (5' AAC GAT ATC GCT AGC GCG GCC GCT CAT TCC TTG GGA TTG GTG 3'(SEQ ID NO: 78)). PCR3c resulted in an approximately 400 base pair product. PCR reactions 1, 2c and 3c were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73500: pTT15d:VK1O2O12::[hu anti-<huCB1> 10D10.1 (huIgG2-TO desK) V$_H$]::(G4S)2::TTR3.

[[SEQ ID NO: 5]-[(GGGGS)$_3$]]$_2$-[SEQ ID NO: 1]$_4$ was assembled as follows. PCR4: using C73500 as template, a 5' PCR primer (5'-AGT TTA AAC GAA TTC GTC GAC TAG GCC ACC ATG GAC ATG AGG GTG CC-3'(SEQ ID NO: 73)), in combination with a 3' primer, encoding the carboxyl terminus human heavy chain constant region (CH3), a (GGGGS)$_3$ (SEQ ID NO: 49) linker, and the amino terminus (5' CGT AGG GCC GGA CCC TCC CCC ACC GGA GCC CCC GCC CCC GGA TCC GCC ACC TCC 3' (SEQ ID NO:83)) of TTR (SEQ ID NO:1). PCR4 resulted in an approximately 1500 base pair product. PCR5: using C73500 as template, a 5' PCR primer encoding a (GGGGS)$_3$ (SEQ ID NO: 49) linker (5' TCC GGG GGC GGG GGC TCC GGT GGG GGA GGG T 3'(SEQ ID NO: 82)), in combination with a 3' primer, encoding the carboxyl terminus region of TTR, a termination codon and NotI restriction site, (5' AAC GAT ATC GCT AGC GCG GCC GCT CAT TCC TTG GGA TTG GTG 3'(SEQ ID NO: 78)). PCR5 resulted in an approximately 450 base pair product. PCR reactions 4 and 5 were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73690: pTT15d:VK1O2O12::[hu anti-<huCB1> 10D10.1 (huIgG2-TO desK) VH]::(G4S)3::TTR3.

[[SEQ ID NO: 5]-[(GGGGS)$_4$]]$_2$-[SEQ ID NO: 1]$_4$ was assembled as follows. PCR6: using C73690 as template, a 5' PCR primer (5'-AGT TTA AAC GAA TTC GTC GAC TAG GCC ACC ATG GAC ATG AGG GTG CC-3'(SEQ ID NO: 73)), in combination with a 3' primer, encoding the carboxyl terminus human heavy chain constant region (CH3) and a (GGGGS) (SEQ ID NO: 50) linker (5' GGA ACC ACC TCC GCC GGA TCC GCC ACC TCC A 3' (SEQ ID NO: 86)). PCR6 resulted in an approximately 1500 base pair product. PCR7: using C73690 as template, a 5' PCR primer encoding a portion of a (GGGGS)$_4$ (SEQ ID NO: 50) linker (5' GGC GGA GGT GGT TCC GGG GGC GGG GGC TCC G 3' (SEQ ID NO: 87)), in combination with a 3' primer, encoding the carboxyl terminus region of TTR (SEQ ID NO: 1), a termination codon and NotI restriction site, (5' AAC GAT ATC GCT AGC GCG GCC GCT CAT TCC TTG GGA TTG GTG 3'(SEQ ID NO: 78)). PCR7 resulted in an approximately 450 base pair product. PCR reactions 6 and 7 were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73729: pTT15d: VK1O2O12::[hu anti-<huCB1>10D10.1 (huIgG2-TO desK) VH]::(G4S)4::TTR3.

[SEQ ID NO: 6]$_4$-[SEQ ID NO: 1]$_4$ was assembled as follows. PCR8:, using C73494 as template, a 5' PCR primer (5'-AGT TTA AAC GAA TTC GTC GAC TAG GCC ACC ATG GAC ATG AGG GTG CC-3'(SEQ ID NO: 73)), in combination with a 3' primer, designed to convert residue glutamate 356 (EU) to lysine within the huIgG2 CH3, (5' CTT GGT CAT CTC CTT CCG GGA TGG GGG CAG G 3' (SEQ ID NO: 88)). PCR8 resulted in an approximately 1200 base pair product. PCR9: using C73494 as template, a 5' PCR primer, designed to convert residue glutamate 356 (EU) to lysine within the huIgG2 CH3, (5'-CTG CCC CCA TCC CGG AAG GAG ATG ACC AAG AAC CA-3' (SEQ ID NO: 89)) in combination with a 3' primer, designed to convert residue aspartate 399 (EU) to lysine within the huIgG2 CH3, (5' GAA GGA GCC GTC GGA CTT CAG CAT GGG AGG TGT 3' (SEQ ID NO: 90)). PCR9 resulted in an approximately 160 base pair product. PCR10: using C73494 as template, a 5' PCR primer, designed to convert residue aspartate 399 (EU) to lysine within the huIgG2 CH3, (5' CCT CCC ATG CTG AAG TCC GAC GGC TCC TTC T 3' (SEQ ID NO: 91)), in combination with a 3' primer, encoding the carboxyl terminus region of TTR, a termination codon and NotI restriction site. PCR10 resulted in an approximately 600 base pair product. PCR reactions 8, 9 and 10 were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73730: pTT15d: VK1O2O12::[hu anti-<huCB1> 10D10.1 (E416K,D459K) (huIgG2-TO desK) VH]::TTR3.

[[SEQ ID NO: 6]-[GGGGS]]$_4$-[SEQ ID NO: 1]$_4$ was assembled as follows. PCR11: using C73499 as template, a 5' PCR primer (5'-AGT TTA AAC GAA TTC GTC GAC TAG GCC ACC ATG GAC ATG AGG GTG CC-3'(SEQ ID NO: 73)), in combination with a 3' primer, designed to convert residue glutamate 356 (EU) to lysine within the huIgG2 CH3, (5' CTT GGT CAT CTC CTT CCG GGA TGG GGG CAG G 3' (SEQ ID NO: 88)). PCR11 resulted in an approximately 1200 base pair product. PCR12:, using C73499 as template, a 5' PCR primer, designed to convert residue glutamate 356 (EU) to lysine within the huIgG2 CH3, (5' CTG CCC CCA TCC CGG AAG GAG ATG ACC AAG AAC CA 3' (SEQ ID NO: 89)) in combination with a 3' primer, designed to convert residue aspartate 399 (EU) to lysine within the huIgG2 CH3, (5' GAA GGA GCC GTC GGA CTT CAG CAT GGG AGG TGT 3' (SEQ ID NO: 90)). PCR12 resulted in an approximately 160 base pair product. PCR13:, using C73499 as template, a 5' PCR primer, designed to convert residue aspartate 399 to lysine within the huIgG2 CH3, (5' CCT CCC ATG CTG AAG TCC GAC GGC TCC TTC T 3' (SEQ ID NO: 91)), in combination with a 3' primer, encoding the carboxyl terminus region of TTR, a termination codon and NotI restriction site, (5' AAC GAT ATC GCT AGC GCG GCC GCT CAT TCC TTG GGA TTG GTG 3'(SEQ ID NO: 78)). PCR13 resulted in an approximately 600 base pair product. PCR reactions 11, 12 and 13 were gel isolated and purified over a Qiagen column. These fragments were then mixed and ligated into a SalI and NotI digested linearized mammalian expression vector pTT15d using a GeneArt Seamless Cloning and Assembly Kit. Amino acid numbering and naming conventions are the same as in the prior constructs description. The resulting construct was termed C73731: pTT15d:VK1O2O12::[hu anti-<huCB1> 10D10.1 (E416K,D459K)(huIgG2-TO desK) VH]::G4S::TTR3.

SEQ ID NO: 7 was constructed as follows. PCR14: using C73494 as template, a 5' PCR primer (5'-AGT TTA AAC GAA TTC GTC GAC TAG GCC ACC ATG GAC ATG AGG GTG CC-3'(SEQ ID NO: 73)), in combination with a 3' primer, designed to convert residue lysine 392 (EU) to aspartate within the huIgG2 CH3, (5' GGG AGG TGT GGT ATC GTA GTT GTT CTC CGG CTG C 3' (SEQ ID NO: 92)). PCR14 resulted in an approximately 1300 base pair product. PCR15: using pTT5-del-Bsm-BI:VK1O2O12:: huFc_(IgG2)(K392D K409D) ("C59541") as template, a 5' PCR primer, designed to convert residue lysine 392 (EU) to aspartate within the huIgG2 CH3, (5' CCG GAG AAC AAC TAC GAT ACC ACA CCT CCC ATG C 3' (SEQ ID NO: 93)) in combination with a 3' primer, encoding the carboxyl terminus region of huIgG2 minus the carboxyl terminal lysine, a termination codon and NotI restriction site, (5' AAC GAT ATC GCT AGC GCG GCC GCT CAA CCC GGA GAC AGG GAG 3' (SEQ ID NO: 94)). PCR15 resulted in an approximately 200 base pair product. PCR reactions 14 and 15 were gel isolated and purified over a Qiagen column. These fragments were then mixed and ligated into a SalI and NotI digested linearized mammalian expression vector pTT15d using a GeneArt Seamless Cloning and Assembly Kit. The resulting construct was termed C73513: pTT15d: VK1O2O12::[hu anti-<huCB1> 10D10.1 (K420D,K437D) (huIgG2-TO desK) VH].

SEQ ID NO: 11 was constructed as follows. PCR16: a 5' PCR primer encoding the amino terminus of the variable region and a BssHIII restriction site (5'-TTT TTT TTG CGC GCT GTG ATA TTG TGA TGA CTC AGT C 3' (SEQ ID NO: 95)) in combination with a 3' primer, encoding the carboxyl terminus of the variable region and a BsiWI restriction site (5'-AAA AAA CGT ACG TTT GAT TTC CAC CTT GGT CC 3' (SEQ ID NO: 96). PCR16 was purified over a Qiagen column. The fragment was then digested with BssHIII and BsiWI, and purified over a Qiagen column. The fragment was then mixed and ligated into a BssHIII and BsiWI digested linearized mammalian expression vector pTT5-del-Bsm-BI containing a signal peptide and kappa constant region. The resulting construct was termed C59474: pTT5-del-Bsm-BI:VK1O2O12::[hu anti-<huCB1> 10D10.1 VL]::huKLC.

Expression of Anti-CB1 TTR Antibody Homodimer, TTR Antibody Homotetramer, and Anti-CB1 TTR Fab Homotetramer Fusion Proteins The anti-CB1 TTR antibody homodimer, TTR antibody homotetramer, and anti-CB1 TTR Fab homotetramer proteins were generally expressed as follows.

HEK 293 6E cells were grown in suspension on a platform shaker in a humidified 37° C. with 5% $CO_2$ incubator with rotation at 120 RPM. The cell culture passage medium was FreeStyle F-17+0.1% (10 mL/L of 10%) Kolliphor P188+500 L/L G418+6 mM (30 mL/L) L-glutamine. The cells were passaged 1-2 days before transfection such that the cell density at transfection was around $1.5e^6$ VC/mL. The transfection complex was mixed in Freestyle F17 medium without supplements at a volume of 10% of the final culture volume. 0.5 µg of DNA was added to the Freestyle F17 medium per mL of culture, add 1.5 µl of PEImax reagent per mL of culture was then added. The medium was then mixed and incubated for 10 min at room temp, then added to cell culture and returned a flask on a shaker platform in the incubator. 25 µL of Yeastolate solution per mL of culture was added, 1-4 hours after transfection. The conditioned medium was harvested at day 6 post transfection.

Freestyle F-17 (Cat #13835), L-glutamine ((Cat #25030), Geneticin G418 (Cat #10131027, liquid) were obtained from Life Technologies. Kolliphor P 188 (Cat #K4894) was obtained from Sigma-Aldrich. Difco TC Yeastolate UF (Cat #292805) was obtained from BD Biosciences. PEI Max (Cat #24765-2) was obtained from Polysciences.

In the gels in FIGS. 2a, 2b, and 2c, 10 µl of sample (not heated) was loaded into each lane of a 4-20% SDS-PAGE and developed with a Coomassie blue based dye system. FIGS. 2a and 2b demonstrate that the anti-CB1 TTR antibody homodimer and the anti-CB1 TTR antibody homotetramer proteins, respectively, are robustly expressed in HEK 293 cells. FIG. 2a demonstrates the anti-CB1 TTR antibody homodimers ([SEQ ID NO: 5]$_2$-[SEQ ID NO: 1]$_4$ and [[SEQ ID NO: 5]-[(GGGGS)$_{1-4}$]]$_2$-[SEQ ID NO: 1]$_4$) are resistant to SDS denaturation and thus form a strong non-covalent complex. Various linker lengths (from shortest ([GGGGS]$_1$ (SEQ ID NO: 47) in Lane 2 to longest ([GGGGS]$_4$ (SEQ ID NO: 50)) in Lane 5); linker length did not appear to substantially impact expression. FIG. 2b demonstrates the formation of anti-CB1 TTR antibody homotetramer, using V1 Fc charge pair mutations (K409D & K392D in one heavy chain and D399K & E356K) (SEQ ID NOs: 6 and 7), also appear to be SDS resistant. Various heavy chain and light chain DNA transfection ratios are shown (from 1:9 LC:HC in Lane 2 to 9:1 LC:HC in Lane 10). LC:HC ratios of 1:1 (Lane 6) and 9:1 (Lane 10) lead to the most robust expression.

FIG. 2c demonstrates that the anti-CB1 TTR Fab homotetramer constructs are robustly expressed in HEK 293 cells and are SDS resistant. TTR fusion was better tolerated at the heavy chain C-terminus (Lanes 2, 4, 6, and 8—less banding) compared to the light chain C-terminus (Lanes 3, 5, 7, and 9—more banding). Location of the His tag did not seem to affect the fusions. The heavy chain-TTR used in Lanes 2 and 4 is [SEQ ID NO: 44]$_4$-[SEQ ID NO: 1]$_4$, and the light chain is SEQ ID NO: 11. The heavy chain used in Lanes 3 and 5 is SEQ ID NO: 44, and the light chain-TTR is [SEQ ID NO: 11]$_4$-[SEQ ID NO: 1]$_4$. The heavy chain-TTR used in Lanes 6 and 8 is [SEQ ID NO: 45]$_4$-[SEQ ID NO: 1]$_4$, and the light chain is SEQ ID NO: 46. The heavy chain used in Lanes 7 and 9 is SEQ ID NO: 45, and the light chain-TTR is [SEQ ID NO: 46]$_4$-[SEQ ID NO: 1]$_4$. Charge pair mutations were included in the anti-CB1 TTR Fab homotetramer constructs tested in Lanes 6-9 (heavy chain having SEQ ID NO: 45, and light chain having SEQ ID NO: 46). SEQ ID NO: 45 contains the S215E charge pair mutation, and SEQ ID NO: 46 contains the charge pair S203K mutation. His tags were also used (see FIG. 2 c).

Purification of Anti-CB1 TTR Fab Homotetramer Fusion Proteins

The anti-CB1 TTR Fab homotetramer proteins were generally purified as follows.

Cell culture media was dialyzed against 2 L of 50 mM $NaH_2PO_4$, 300 mM NaCl, 10 mM imidazole, pH 8.0 for a minimum of 2 hours, twice, using 10 kDa MWCO Slide-a-lyzers (Thermo Fisher Scientific). The molecules were purified from the buffer exchanged cell culture media using an AKTA Purifier (GE Healthcare Life Sciences) tandem liquid chromatography system with a 1 mL Ni-NTA Superflow cartridge (Qiagen, Hilden, Germany) as the first column, and a 5 mL Desalting HiTrap (GE Healthcare Life Sciences) as the second column. The media was loaded directly onto the Ni-NTA column, washed with 8 CV of 50 mM Na-phosphate, 300 mM NaCl, 10 mM imidazole, pH 8.0, and eluted with 2 CV of 50 mM Na-phosphate, 300 mM NaCl, 250 mM imidazole, pH 8.0. The Ni-NTA column eluate was automatically channeled to the Desalting column where the protein was eluted isocratically over 4 CV of 10 mM Na-acetate, 150 mM NaCl, pH 5.2. The samples were sterile filtered through a 3.0 µm glass fiber/0.2 µm Supor membrane (Pall Corporation, Port Washington, New York, USA).

The protein concentration of each purified molecule was determined by UV absorbance at 280 nM (A280) using a NanoDrop 2000 (Thermo Fisher Scientific, Rockford, Illinois, USA). SDS-PAGE analysis was conducted on 3 µg of each final purified molecule on a denaturing, non-reducing 4-12% Bis-Tris NuPAGE gel using MES running buffer (Life Technologies, Carlsbad, California, USA), per manufacturer instructions. HPLC size exclusion chromatography analysis was conducted on 20 µg of each final purified molecule, which was run on a Phenomenex SEC 3000 column, 7.8×300 mm (Phenomenex, Torrance, California, USA) in 50 mM $NaH2PO4$, 250 mM NaCl, pH 6.9 at 1 mL/min observing the absorbance at 280 nm.

Purification of Anti-CB1 TTR Antibody Homodimer and TTR Antibody Homotetramer Fusion Proteins The anti-CB1 TTR antibody homodimer and TTR antibody homotetramer fusion proteins were generally purified as follows.

The fusion proteins were initially purified from cell culture media using an AKTA Purifier (GE Healthcare Life Sciences, Little Chalfont, Buckinghamshire, UK) tandem liquid chromatography system with a 1 mL MabSelect SuRe (MSS) HiTrap (GE Healthcare Life Sciences) as the first column, and a 5 mL Desalting HiTrap (GE Healthcare Life Sciences) as the second column. The media was loaded directly onto the MSS column, washed with 8 column volumes (CV) of 25 mM Tris-HCl, 100 mM NaCl, pH 7.4, and eluted with 2 CV of 100 mM acetic acid. The MSS column eluate was automatically channeled to the Desalting column where the protein was eluted isocratically over 4 CV of 10 mM Na-acetate, 150 mM NaCl, pH 5.2. The samples were sterile filtered through a 3.0 m glass fiber/0.2 µm Supor membrane (Pall Corporation, Port Washington, New York, USA). The protein concentration of each purified molecule was determined by UV absorbance at 280 nM (A280) using a NanoDrop 2000 (Thermo Fisher Scientific, Rockford, Illinois, USA). SDS-PAGE analysis was conducted on 3 µg of each final purified molecule was run on a denaturing, non-reducing 4-12% Bis-Tris NuPAGE gel using MES running buffer (Life Technologies, Carlsbad, California, USA), per manufacturer instructions. HPLC size exclusion chromatography analysis was conducted on 30 μg of each final purified molecule, which was run on a Phenomenex SEC 3000 column, 7.8×300 mm (Phenomenex, Torrance, California, USA) in 50 mM NaH$_2$PO$_4$, 250 mM NaCl, pH 6.9 at 1 mL/min observing the absorbance at 280 nm. FIG. 3 shows a representative HPLC SEC analysis of the anti-CB1 TTR antibody homodimer fusion protein with no linker, a (G$_4$S) linker, a (G$_4$S)$_2$ linker, a (G$_4$S)$_3$ linker, or a (G$_4$S)$_4$ linker.

Example 3: Activity of Anti-CB1 TTR Antibody Homodimer, TTR Antibody Homotetramer, and TTR Fab Homotetramer Fusion Proteins Activity of the anti-CB1 TTR antibody homodimer, TTR antibody homotetramer, and TTR Fab homotetramer fusion proteins was accessed via a CB1 cAMP Assay.

CHO cells stably expressing hCB1 (Euroscreen) were grown in DMEM containing 10% FBS, 1% Pen/Strep/L-glutamine, 25 mM Hepes, 0.1 mM NEAA, 1 mM sodium pyruvate, and 400 μg/ml G418. To determine antibody activity, cells were seeded in 96-well plates at a density of 10,000 cells per well in 80 μl DMEM containing 0.5% FBS, 1% Pen/Strep/L-glutamine, 25 mM Hepes, 0.1 mM NEAA, 1 mM sodium pyruvate, and 400 g/ml G418. After overnight incubation, the media was removed and replaced with 5 μl fresh media followed by 5 μl of media plus 15 M forskolin (EMD Chemicals Cat #344273) and 250 pM CP55,940 (TOCRIS Cat #0949) followed by 40 μl of antibody in 10 mM acetic acid, 150 mM NaCl, pH 5.0. The cells were then incubated for 30 minutes at 37° C. The media was then aspirated and cAMP levels were measured using a DiscoverX XS+cAMP assay kit (90-0075-03) following the manufacturer's protocol. Plates were read for 30 seconds on PerkinElmer ViewLux Microplate Imager.

Figure 4:
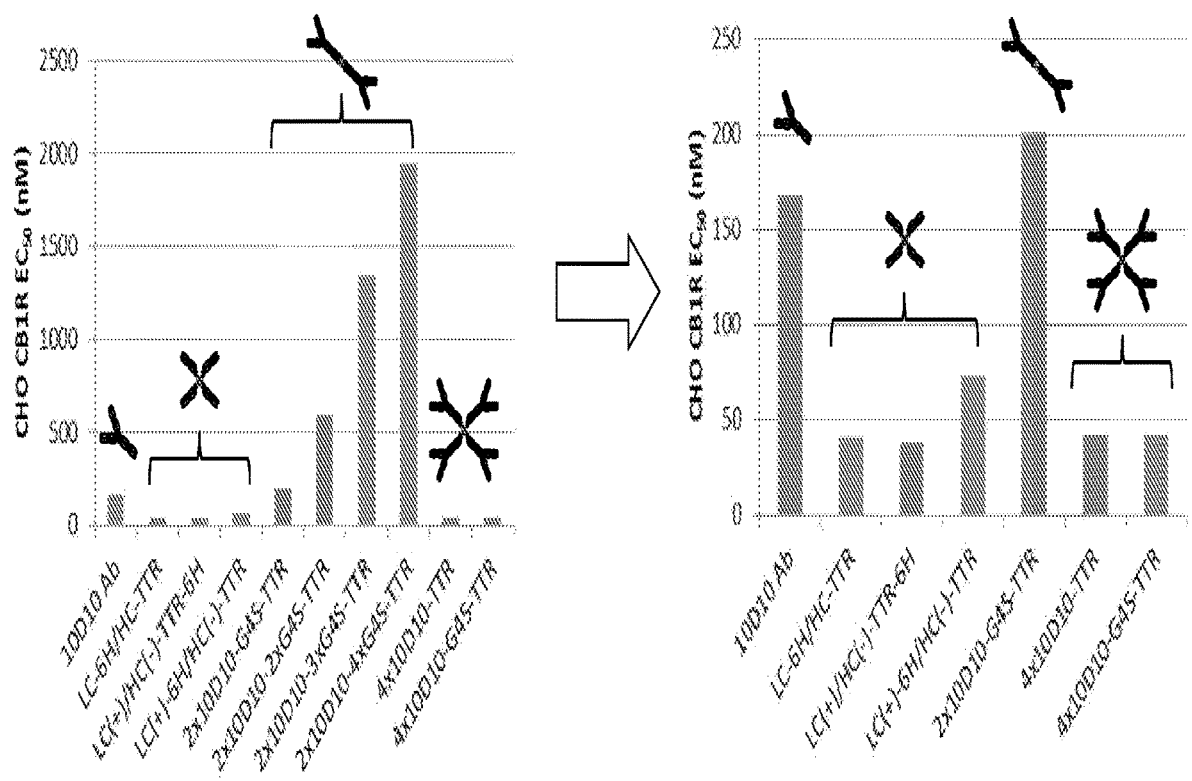
FIG. 4 shows that the TTR anti-CB1 antibody homotetramer and TTR anti-CB1 Fab homotetramer fusion proteins improve $EC_{50}$ compared to parental CB1 Ab.

The results of the assay are represented in FIG. 4. The TTR antibody homotetramer has a 3.9 fold more favorable $EC_{50}$ than the CB1 parent antibody. Some Fabs used charge pair mutations while others did not (see discussion of FIG. 2 in Example 2). These results demonstrate that the TTR antibody homotetramer and TTR Fab homotetramer fusion proteins improve $EC_{50}$ compared to parental CB1 Ab. Interestingly, the anti-CB1 TTR antibody homodimer appears to have a less favorable $EC_{50}$ than the CB1 parent antibody, with worsening $EC_{50}$ as the length of the linker increases.

Example 4: Cloning, Expression, and Purification of Anti-GITR TTR Antibody Homodimer, TTR Antibody Homotetramer, and TTR Fab Homotetramer Fusion Proteins Cloning of Anti-GITR TTR Antibody Homodimer, TTR Antibody Homotetramer, and TTR Fab Homotetramer Fusion Proteins The anti-GITR TTR antibody homodimer and TTR antibody homotetramer fusion proteins were generally cloned as follows. Constructs C74201 (pSLX240p:Native::[hu anti-<huGITR> 9H6 (D72(62)E) VH]::huIgG1z-N297G); C143046 (pTT5d:VK1O2O12::[hu anti-<huGITR> 9H6 (S183E, N297G, E356K, D399K) VH]::TTR(C10A, K15A); C143048(pTT5d:VK1O2O12::[hu anti-<huGITR> 9H6 (S183K, N297G, K392D, K409D) VH]::TTR(C10A, K15A); C137324(VK1O2O12::[hu anti-<huGITR> 9H6 VL]) and C73877(pTT5:Native::[hu anti-<huGITR> 9H6 VL]::huKLC) were used as templates for all constructs described below.

[SEQ ID NO: 18]$_2$-[SEQ ID NO: 1]$_4$ was assembled as follows. PCR17: using C74201 as template, the signal peptide of the anti-GITR MAb 9H6 (w/N297G) was replaced with the VK1 signal peptide (MDMRVPAQLLGLLLLWLRGARC (SEQ ID NO: 97)) by three step overlapping PCR elongation and that the product of that final PCR was then amplified using the 5' signal peptide primer (5'-GTC GAC TAG GCC ACC ATG GAC ATG AGG GTG CCC GCT CAG CTC CTG GGG CT-3' (SEQ ID NO: 98)) and the 3' C-terminal heavy chain/N-terminal TTR primer (GGT GCC CGT AGG GCC ACC CGG AGA CAG GGA GAG G 3' (SEQ ID NO: 99)) to yield the 1450 base pair product. PCR18: using TTR (SEQ ID NO: 1) as template, a 5' PCR primer encoding the amino terminus of TTR (5'-GGC CCT ACG GGC ACC G-3' (SEQ ID NO: 99)), in combination with a 3' primer, encoding the carboxyl terminus region of TTR, a termination codon and NotI restriction site, (5'-TCG CTA GCG CGG CCG CTC ATT CCT TGG GAT TGG TGA CG-3' (SEQ ID NO: 101)). PCR18 resulted in an approximately 400 base pair product. PCR reactions 17 and 18 were gel isolated and purified over a Qiagen column. These fragments were then mixed and ligated into a SalI and NotI digested linearized mammalian expression vector pTT5d using a GeneArt Seamless Cloning and Assembly Kit. The resulting construct was termed C143043: pTT5d:VK1O2O12::[hu anti-<huGITR> 9H6 (N297G) VH]::TTR(C10A, K15A).

[SEQ ID NO: 21]$_4$-[SEQ ID NO: 1]$_4$ was assembled as follows. PCR19: using C74201 as template, the signal peptide of the anti-GITR MAb 9H6 (C74201) was replaced with the VK1 signal peptide (MDMRVPAQLLGLLLL-WLRGARC (SEQ ID NO: 97)) by three step overlapping PCR elongation and that the product of that final PCR was then amplified using the 5' signal peptide primer (5'-GTC GAC TAG GCC ACC ATG GAC ATG AGG GTG CCC GCT CAG CTC CTG GGG CT-3' (SEQ ID NO: 98)) and the 3' C-terminal heavy chain/N-terminal TTR primer (5'-GCT CTC GAG GGA GTA GAG TCC TGA GGA CTG TAG G-3' (SEQ ID NO: 102) to yield the 650 base pair product. PCR20: using C74201 as template, a 5' PCR primer encoding the carboxyl terminus human heavy chain constant region (5'-CTC TAC TCC CTC GAG AGC GTG GTG ACC GTG CC-3' (SEQ ID NO: 103)), in combination with a 3' primer, encoding the human heavy chain constant region (5'-CCT CCT CCA CAA GAT TTG GGC TCA ACT TTC TTG TC-3' (SEQ ID NO: 104). PCR20 resulted in an approximately 130 base pair product. PCR21: using TTR3 as template, a 5' PCR primer encoding the amino terminus of TTR (5'-CAA ATC TTG TGG AGG AGG CCC TAC GGG CAC CG-3' (SEQ ID NO: 105), in combination with two 3' primers, encoding the carboxyl terminus region of TTR, a termination codon and NotI restriction site, (5'-ATG GTG ATG GTG ACC GCC TTC CTT GGG ATT GGT GAC GAC A-3' (SEQ ID NO: 106)) and (5'-ATC GCT AGC GCG GCC GCC TAG TGG TGA TGG TGA TGG TGA CC-3' (SEQ ID NO: 107)). PCR21 resulted in an approximately 450 base pair product. PCR reactions 19, 20 and 21 were gel isolated and purified over a Qiagen column. These fragments were then mixed and ligated into a SalI and NotI digested linearized mammalian expression vector pTT5d using a GeneArt Seamless Cloning and Assembly Kit. The resulting construct was termed C144132: pTT5d:VK1O2O12::[hu anti-<huGITR> 9H6 (S183E) scFab]::TTR(C10A, K15A):: G::G::6×His (note that the (His)₆ tag was included for purification purposes).

[SEQ ID NO: 19]₄-[SEQ ID NO: 1]₄ was assembled as follows. PCR22: using C74201 as template, the signal peptide of the anti-GITR MAb 9H6 (C74201) was replaced with the VK1 signal peptide (MDMRVPAQLLGLLLL-WLRGARC (SEQ ID NO: 97)) by three step overlapping PCR elongation and that the product of that final PCR was then amplified using the 5' signal peptide primer (5'-GTC GAC TAG GCC ACC ATG GAC ATG AGG GTG CCC GCT CAG CTC CTG GGG CT-3' (SEQ ID NO: 98)) and the 3' C-terminal heavy chain/N-terminal TTR primer (5'-TAG GTG CTT CCG TAC TGT TCC TCC CGG GGC TT-3' (SEQ ID NO: 108)) to yield the 990 base pair product. PCR23: using C143046 as template, a 5' PCR primer encoding the carboxyl terminus human heavy chain constant region (CH3) (5'-CCT GAG CAG CGT CGT CAC CGT CCC-3' (SEQ ID NO: 109)), in combination with a 3' primer, encoding the carboxyl terminus human heavy chain constant region (CH3) (5'-TAG GTG CTT CCG TAC TGT TCC TCC CGG GGC TT-3'(SEQ ID NO: 108)). PCR23 resulted in an approximately 370 base pair product. PCR24: using TTR3 as template, a 5' PCR primer encoding carboxyl terminus region of TTR (5'-CAG TAC GGA AGC ACC TAC CGG GTG GTG TC-3' (SEQ ID NO: 110)), in combination with a 3' primer, encoding the carboxyl terminus region of TTR, a termination codon and NotI restriction site (5'-TCG CTA GCG CGG CCG CTC ATT CCT TGG GAT TGG TGA CG-3' (SEQ ID NO: 101)). PCR24 resulted in an approximately 900 base pair product. PCR reactions 22, 23 and 24 were gel isolated and purified over a Qiagen column. These fragments were then mixed and ligated into a SalI and NotI digested linearized mammalian expression vector pTT5d using a GeneArt Seamless Cloning and Assembly Kit. The resulting construct was termed C144127: pTT5d:VK1O2O12::[hu anti-<huGITR> 9H6 (N297G, E356K, D399K) VH]::TTR(C10A, K15A).

SEQ ID NO: 20 was assembled as follows. PCR25: using C143048 as template, a 5' PCR primer encoding the amino terminus of the signal peptide (5'-GTC GAC TAG GCC ACC ATG GAC ATG AGG GTG CCC GCT CAG CTC CTG GGG CT 3' (SEQ ID NO:98)) in combination with a 3' primer, encoding the carboxyl terminus human heavy chain constant region (CH3) (5'-ACG GTG ACG ACG CTG CTC AGG CTG TAC AGG CCG CTG-3' (SEQ ID NO:111)). PCR25 resulted in an approximately 650 base pair product. PCR26: using C143048 as template, a 5' PCR primer encoding the carboxyl terminus human heavy chain constant region (CH3) (5'-CCT GAG CAG CGT CGT CAC CGT CCC-3' (SEQ ID NO: 109)), in combination with a 3' primer, encoding the carboxyl terminus human heavy chain constant region (CH3) (5'-TAG GTG CTT CCG TAC TGT TCC TCC CGG GGC TT-3'(SEQ ID NO: 108)). PCR26 resulted in an approximately 370 base pair product. PCR27: using TTR3 as template, a 5' PCR primer encoding carboxyl terminus region of TTR (5'-CAG TAC GGA AGC ACC TAC CGG GTG GTG TC-3' (SEQ ID NO: 110)), in combination with a 3' primer, encoding the carboxyl terminus region of TTR, a termination codon and NotI restriction site (5'-TCG CTA GCG CGG CCG CTC ATT CCT TGG GAT TGG TGA CG-3' (SEQ ID NO: 101). PCR27 resulted in an approximately 900 base pair product. PCR reactions 25, 26 and 27 were gel isolated and purified over a Qiagen column. These fragments were then mixed and ligated into a SalI and NotI digested linearized mammalian expression vector pTT5d using a GeneArt Seamless Cloning and Assembly Kit. The resulting construct was termed C144130: pTT5d:VK1O2O12::[hu anti-<huGITR> 9H6 (N297G, K392D, K409D) VH].

SEQ ID NO: 25 was assembled as follows. PCR28: using C137324 as template, a 5' PCR primer encoding the amino terminus of the signal sequence (5'-GTC GAC TAG GCC ACC ATG GAC ATG AGG GTG CCC GCT CAG CTC CTG GGG CT 3' (SEQ ID NO: 98)) in combination with a 3' primer, encoding the carboxyl terminus human light chain constant region (5'-TAT CGC TAG CGC GGC CGC-3' (SEQ ID NO: 112)). PCR28 resulted in an approximately 800 base pair product. PCR 28 was gel isolated and purified over a Qiagen column. The fragment was then mixed and ligated into a SalI and NotI digested linearized mammalian expression vector pTT5d using a GeneArt Seamless Cloning and Assembly Kit. The resulting construct was termed C143044: pTT5d:VK1O2O12::[hu anti-<huGITR> 9H6 VL].

SEQ ID NO: 26 was assembled as follows. PCR29: using C137324 as template, a 5' PCR primer encoding the amino terminus of the signal sequence (5'-GTC GAC TAG GCC ACC ATG GAC ATG AGG GTG CCC GCT CAG CTC CTG GGG CT 3' (SEQ ID NO: 98)) in combination with a 3' primer, encoding the carboxyl terminus human light chain constant region (5'-TGG TGC AGC CAC CGT ACG TTT GAT TTC CAC CTT GGT CC-3'). PCR29 resulted in an approximately 400 base pair product. PCR30: using C73877 as template, 5' PCR primers encoding the carboxyl terminus human light chain constant region (5'-ACG GTG GCT GCA CCA TCT G-3') in combination with a 3' primer, encoding the carboxyl terminus human light chain constant region (5'-TAT CGC TAG CGC GGC CGC-3' (SEQ ID NO: 112)). PCR reactions 29 and 30 were gel isolated and purified over a Qiagen column. The fragment was then mixed and ligated into a SalI and NotI digested linearized mammalian expression vector pTT5d using a GeneArt Seamless Cloning and Assembly Kit. The resulting construct was termed C143049: pTT5d:VK1O2O12::[hu anti-<huGITR> 9H6 (S176K) VL].

Expression of Anti-GITR TTR Antibody Homodimer, TTR Antibody Homotetramer, and TTR Fab Homotetramer Fusion Proteins The anti-GITR TTR antibody homodimer, TTR antibody homotetramer, and TTR Fab homotetramer fusion proteins were generally expressed as follows.

Freestyle F-17 (Cat #13835), L-glutamine ((Cat #25030), Geneticin G418 (Cat #10131027, liquid) were obtained from Life Technologies. Kolliphor P 188(Cat #K4894) was obtained from Sigma-Aldrich. Difco TC Yeastolate UF(Cat #292805) was obtained from BD Biosciences. PEI Max (Cat #24765-2) was obtained from Polysciences. HEK 293 6E cells were grown in suspension on a platform shaker in a humidified 37° C. with 5% $CO_2$ incubator with rotation at 120 RPM. The cell culture passage medium was FreeStyle F-17+0.1% (10 mL/L of 10%) Kolliphor P188+500 uL/L G418+6 mM (30 mL/L) L-glutamine. Cells were passaged 1-2 days before transfection such that the cell density at transfection is around $1.5e^6$ VC/mL. Transfection complex was mixed in Freestyle F17 medium without supplements at a volume of 10% of the final culture volume. 0.5 µg of DNA was added to Freestyle F17 medium per mL of culture; then 1.5 µl of PEImax reagent per mL of culture was added. The culture was mixed and incubated for 10 min at room temp, and then added to cell culture. The culture flask was then returned to the shaker platform in the incubator. 25 µL of Yeastolate solution per mL of culture was added, 1-4 hours after transfection. The conditioned medium was then harvested at day 6 post transfection.

The anti-GITR TTR antibody homodimer was alternatively expressed as follows. HEK 293 cells were transiently transfected with the corresponding cDNAs. Suspension HEK 293-6E cells at $1.0\times10^6$ cells/mL were transfected with 0.5 mg/L DNA (0.25 mg/L hu anti-<huGITR> 9H6 (N297G) VH]::TTR(C10A, K15A) in pTT5d vector and 0.25 mg/L hu anti-<huGITR> 9H6 VL in pTT5d vector) (Durocher et al. NRCC, Nucleic Acids. Res. (2002) 30, e9) with 4 mg PEI (Polysciences) to 1 mg DNA in FreeStyle F17 medium (Life Technologies) and incubated in shake flask at 150 RPM at 36° C. Yeastolate (BD Biosciences) for final 0.5% of transfection was added to cultures 4 hour after transfection. Cells were grown in suspension in FreeStyle F17 medium supplemented with 0.1% Pluronic F68 and 50 µg/ml Geneticin for 6 days and harvested for purification.

Figure 5:
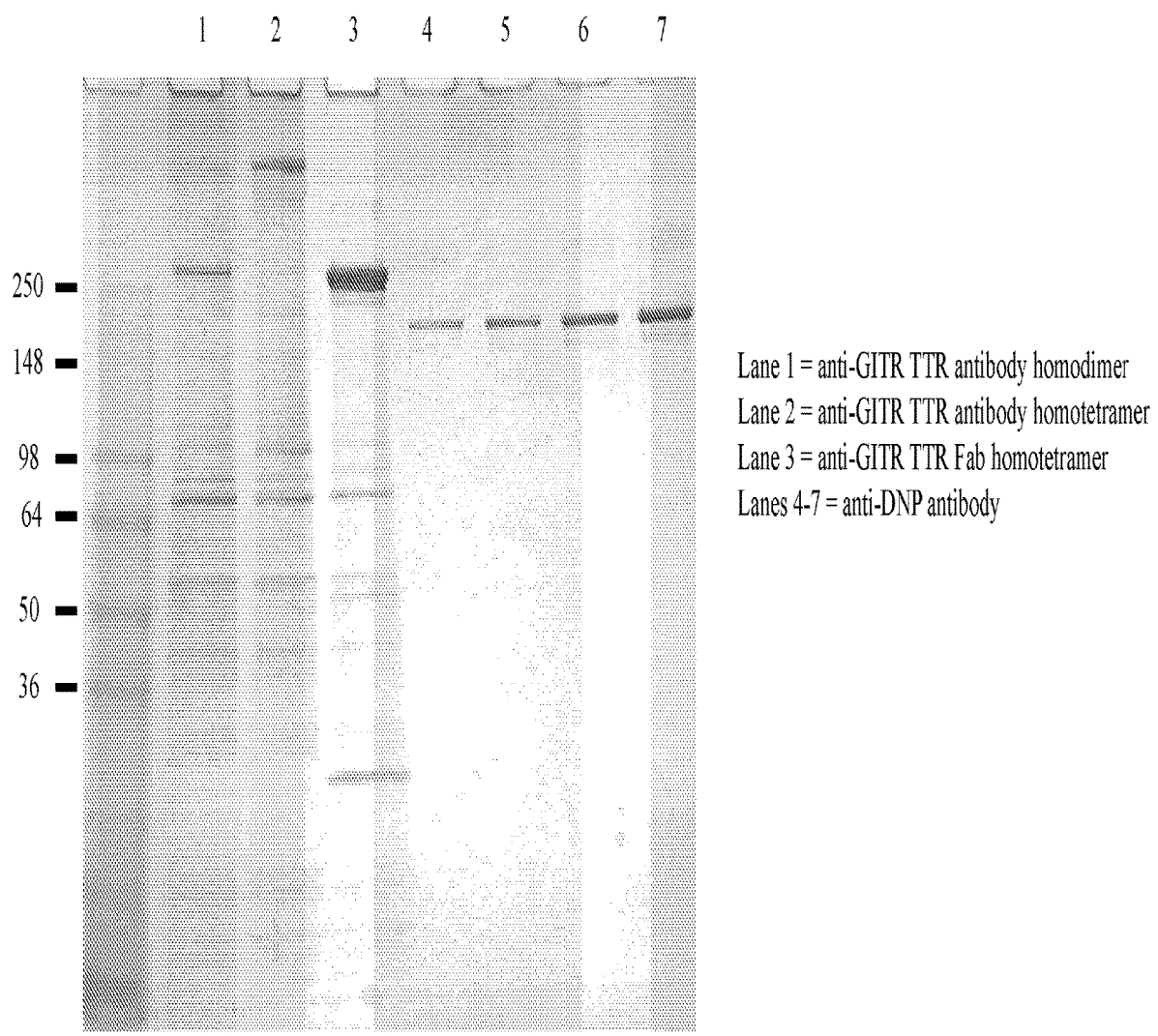
FIG. 5 is an SDS-PAGE gel that demonstrates that the anti-GITR TTR antibody homodimer (Lane 1), anti-GITR TTR antibody homotetramer (Lane 2), and anti-GITR TTR Fab homotetramer proteins (Lane 3), respectively, are expressed in HEK 293 cells. Lanes 4-7 are anti-dinitrophenyl (anti-DNP) antibody.

The conditioned media was analyzed using 4-20% SDS-PAGE and Quick Blue Stain gel. FIG. 5 demonstrates that the anti-GITR TTR antibody homodimer, TTR antibody homotetramer, and TTR Fab homotetramer fusion proteins can be expressed in HEK 293 cells. Expression was most robust for the anti-GITR TTR antibody homotetramer and TTR Fab homotetramer. Lane 1 is 10.3 mg of anti-GITR TTR antibody homodimer (356 KDa); Lane 2 is 29.3 mg of anti-GITR TTR antibody homotetramer (656 KDa); Lane 3 is 143.6 mg of anti-GITR TTR Fab homotetramer (256 KDa); Lane 4 is 100 ng of anti-DNP antibody; Lane 5 is 250 ng of anti-DNP antibody; Lane 6 is 500 ng of anti-DNP antibody; and Lane 7 is 1000 ng of anti-DNP antibody. Anti-DNP antibodies provide information of how an unconjugated antibody would perform in this assay. 10 µl of protein in non-reducing loading buffer was added to each lane. The gels were run without heating.

Purification and Characterization of Anti-GITR TTR Antibody Homodimer, TTR Antibody Homotetramer, and TTR Fab Homotetramer Fusion Proteins The anti-GITR TTR antibody homodimer, TTR antibody homotetramer, and TTR Fab homotetramer fusion proteins were generally purified and characterized as follows.

The anti-GITR TTR antibody homodimer and TTR antibody homotetramer fusion proteins were purified from cell culture media using an AKTA Purifier (GE Healthcare Life Sciences) liquid chromatography system with two, sequentially linked 1 mL rProtein A Sepharose Fast Flow (ProA FF) HiTrap (GE Healthcare Life Science) columns. The media was loaded directly onto the ProA FF columns, washed with 5 CV of Dulbecco's Phosphate Buffered Saline (DPBS) (Life Technologies), and eluted with 8 CV of 100 mM acetic acid. The purified samples were dialyzed against 2 L of 10 mM Na-acetate, 9% sucrose, pH 5.2, twice, using 10 kDa MWCO Slide-a-lyzers (Thermo Fisher Scientific).

TTR Fab homotetramer fusion proteins were purified from cell culture media using an AKTA Purifier liquid chromatography system with a 5 mL HisTrap excel HiTrap (GE Healthcare Life Sciences) column. The media was loaded directly onto the HisTrap column, then washed with 20 CV of 20 mM NaH2PO4, 0.5 M NaCl, 10 mM imidazole, pH 7.4 and eluted with a 20 CV imidazole gradient from 10 mM to 500 mM. A re-purification of the flowthrough fraction was carried out under the same aforementioned conditions, except employing an 8 CV 20 mM NaH2PO4, 0.5 M NaCl, 500 mM imidazole, pH 7.4 step elution instead of a gradient elution due to the lack of chromatographic resolution in the former method. The purified samples were dialyzed against 2 L of 10 mM Na-acetate, 9% sucrose, pH 5.2, twice, using 10 kDa MWCO Slide-a-lyzers.

The protein concentration of the anti-GITR TTR antibody homodimer, TTR antibody homotetramer, and TTR Fab homotetramer fusion proteins was determined by UV absorbance at 280 nM (A280) using a NanoDrop 2000 (Thermo Fisher Scientific, Rockford, Illinois, USA).

Figure 6:
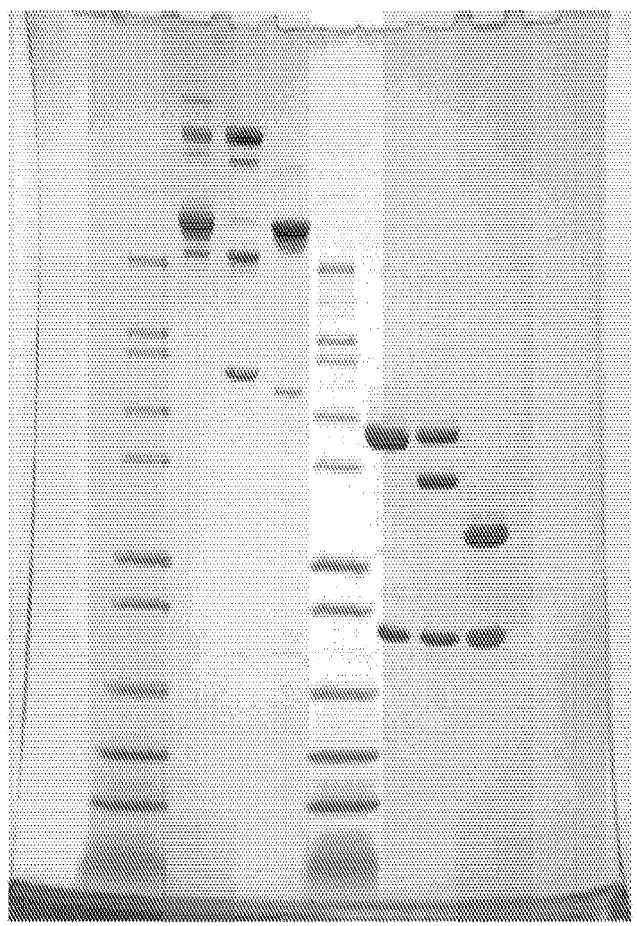
FIG. 6 is an SDS-PAGE gel that demonstrates that the anti-GITR TTR antibody homodimer (Lanes 1 and 4), anti-GITR TTR antibody homotetramer (Lanes 2 and 5), and anti-GITR TTR Fab homotetramer proteins (Lanes 3 and 6) correctly assemble based on the non-heated, non-reduced lanes. Upon heating and reduction, the three protein fusion constructs break down to their expected component chains (upper band(s) are heavy chains and lowest band is light chain).

SDS-PAGE analysis (carried out on 3 µg of each of the anti-GITR TTR antibody homodimer, TTR antibody homotetramer, and TTR Fab homotetramer fusion proteins) was run on a denaturing, non-reducing 4-12% Bis-Tris NuPAGE gel using MES running buffer (Life Technologies, Carlsbad, California, USA), per manufacturer instructions. See FIG. 6. Lanes 1 and 4 are anti-GITR TTR antibody homodimer; Lanes 2 and 5 are anti-GITR TTR antibody homotetramer; Lanes 3 and 6 are anti-GITR TTR Fab homotetramer. FIG. 6 demonstrates that partially purified products for all three protein fusion constructs correctly assemble based on the non-heated, non-reduced lanes. Upon heating and reduction, the three protein fusion constructs break down to their expected component chains (upper bands are heavy chains and lowest band is light chain).

HPLC size exclusion chromatography analysis was carried out on 30 µg of each of the anti-GITR TTR antibody homodimer, TTR antibody homotetramer, and TTR Fab homotetramer fusion proteins. The chromatography utilized a Phenomenex SEC 3000 column, 7.8×300 mm (Phenomenex, Torrance, California, USA) in 50 mM NaH$_2$PO$_4$, 250 mM NaCl, pH 6.9 at 1 mL/min observing the absorbance at 280 nm.

The anti-GITR TTR antibody homodimer, TTR antibody homotetramer, and TTR Fab homotetramer fusion proteins were analyzed via reduced LCMS analysis. 20 µg of material was denatured in 8M guanidine HCl/TRIS pH 8.0 (Teknova, Hollister, CA), and reduced with 10 mM DTT (EMD Millipore, Darmstadt, Germany) at 50° C. for 20 minutes. The samples were acidified with trifluoroacetic acid, and 10 µg injected on a Zorbax reverse phase C8 column using an Agilent 1260 HPLC (Agilent Technologies, Santa Clara, CA). The column effluent was introduced to an electrospray source of an Agilent 6230 ESI-TOF mass spectrometer (Agilent Technologies, Santa Clara, CA) and mass spectra were collected. Relevant spectra were deconvoluted using the MaxEnt algorithm within the Agilent MassHunter software package. The resulting mass spectra for the LC and HC were compared to the theoretically calculated masses for each chain.

The purified anti-GITR TTR antibody homodimer was further purified (to remove aggregates that had accumulated over time) on a 320 mL Superdex 200 (GE Healthcare Life Science) isocratically over 1.4 CV of 10 mM Na-acetate, 150 mM NaCl, pH 5.0. Fractions were selected for pooling by HPLC-SEC purity. The Superdex pools were concentrated using VivaSpin 10 kDa MWCO centrifugal filtration units (Sartorius) and then sterile filtered through 0.2 µm Supor syringe filters (Pall). HPLC size exclusion chromatography analysis was carried out on a Sepax Zenix-C, 7.8×300 mm column (Sepax, Newark, Delaware, USA) in 50 mM NaH2PO4, 250 mM NaCl, pH 6.9 at 1 mL/min observing the absorbance at 280 nm.

Figure 7:
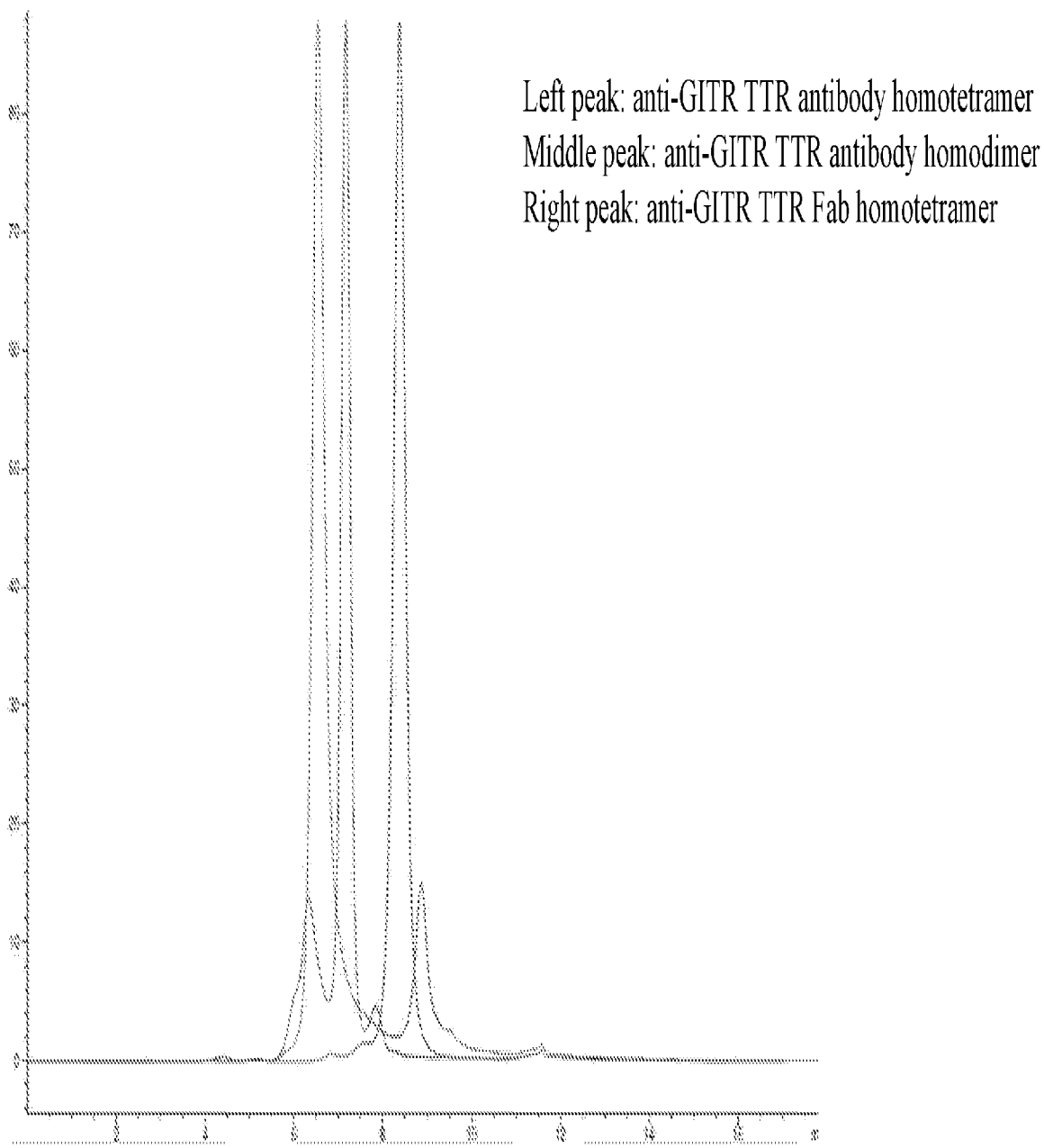
FIG. 7 is an HPLC SEC analysis of each of the anti-GITR TTR antibody homodimer (middle peak), TTR antibody homotetramer (left peak), and TTR Fab homotetramer (right peak) fusion proteins.

FIG. 7 shows the results of the HPLC size exclusion chromatography (SEC) analysis of each of the anti-GITR TTR antibody homodimer (middle peak), TTR antibody homotetramer (left peak), and TTR Fab homotetramer (right peak) fusion proteins. The SEC chromatograms demonstrate that the main peak elutes at the expected position consistent with correctly assembled molecules. Moreover, the non-denaturing SEC purification (unlike SDS-PAGE) supports the notion that the fusion proteins are not aggregated.

Reduced LCMS reanalysis of the repurified anti-GITR TTR antibody homodimer was carried out. About 10 µg of anti-GITR TTR antibody homodimer was dried down in a Speed-Vac, then resuspended in 20 μL of a solution of 8M Gu-HCl, pH 8.0 with 20 mM DTT. The sample was incubated at 37° C. for 1 hour to reduce each sample into individual protein chain components. Each reduced sample was then acidified by the addition of 0.1% TFA. For LC-MS, about 5 μg of the reduced sample was injected onto an Agilent Technologies 1100 capillary HPLC spraying into an Agilent Technologies 6224 ESI-TOF mass spectrometer. The capillary HPLC used a 1.0 mm×50 mm Agilent Zorbax 300SBC8 column with a flow rate of 50 μL/min and a column temperature of 75° C. The HPLC used the following buffers: Buffer A—0.1% TFA/H2O; Buffer B—0.1% TFA/H2O/90% n-propanol. The gradient consisted of initial conditions at 2% B for 5 minutes, a ramp up to 45% B over 20 minutes, up to 95% B over 3 minutes, isocratic at 95% B for 4 minutes, and then back down to 2% B over 1 minute. The MS method for the ESI-TOF instrument scanned m/z [750-6000] at a rate of 1 spectra/second. Other MS instrumental parameters include capillary voltage (VCap)=3200V, fragmentor voltage=225V, skimmer=60V, and OCT 1 RF Vpp=800V. For data analysis of the LC-MS data, the appropriate LC-MS spectra for each protein chain were combined and deconvoluted using the Agilent MassHunter software. The deconvoluted output mass range was [15,000-75,000] with a mass step of 1.0 Da and a signal/noise (S/N) threshold of 30.0. The correct reduced chain masses were observed for each sample. There was trace Asp-Pro cleavage observed in the anti-GITR TTR antibody homodimer heavy chain, the result of using an analytical temperature of 75° C.

Figure 8:
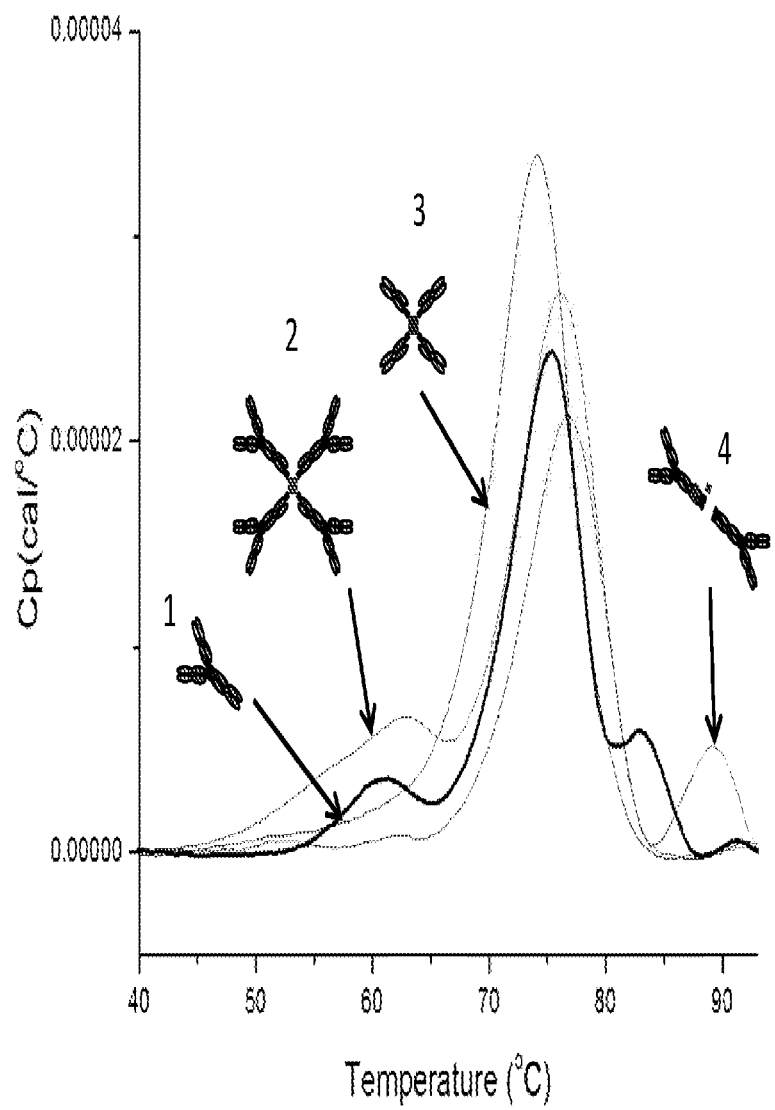
FIG. 8. is a differential scanning calorimetry (DSC) analysis of the anti-GITR TTR parental mAb ("1"), anti-GITR TTR antibody homotetramer ("2"), anti-GITR TTR Fab homotetramer ("3"), and anti-GITR TTR antibody homodimer ("4") fusion proteins.

Differential Scanning Calorimetry (DSC) of the anti-GITR TTR parental mAb 9H6 ("1"), anti-GITR TTR antibody homodimer ("4"), TTR antibody homotetramer ("2"), and TTR Fab homotetramer ("3") fusion proteins was performed on a Malvern MicroCal VP-Capillary DSC. See FIG. 8. The following parameters were used: scanning range: 10-100° C.; scanning rate: 1° C./min; pre-scan thermostat 15 min. Typically 400 μL of 1 mg/mL sample is consumed for each analysis. Data is processed in Origin 7 software. The analyzed proteins were expressed in HEK 293-6E cells. Although the parental Ab ("1") is glycosylated, the TTR fusions are N297G a-glyco variants. The results in FIG. 8 demonstrate that the melting temperatures of the TTR fusion proteins are comparable or better than the parental Ab, indicating that the formed TTR fusion proteins are robust. The anticipated heat induced transition order was CH2, Fab, CH3.

Figure 10:
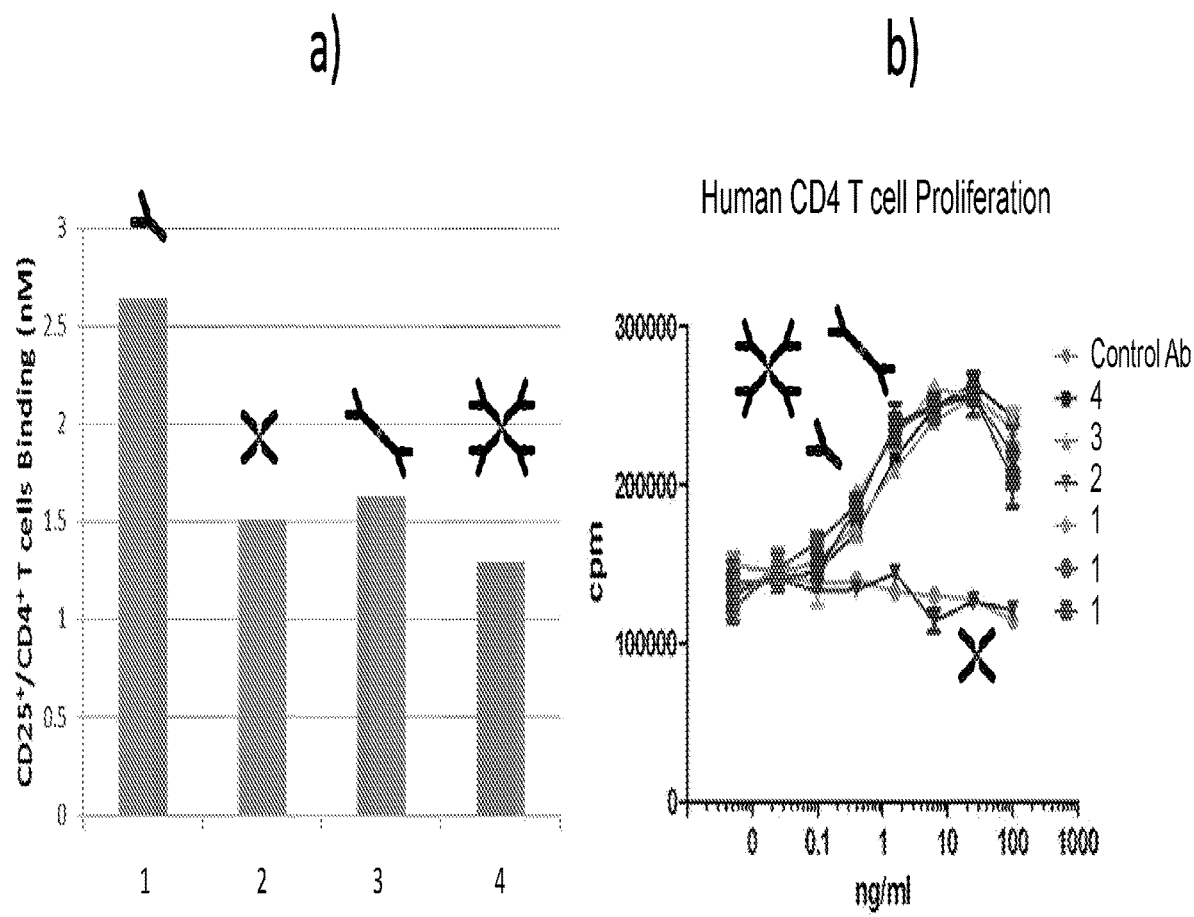
FIG. 10 a) demonstrates that the binding affinity of the anti-GITR TTR Fab homotetramer ("2"), anti-GITR TTR antibody homodimer ("3"), and anti-GITR TTR antibody homotetramer ("4") fusion proteins is better than the parental anti-GITR mAb ("1").

Example 5: Activity and PK Profile of Anti-GITR TTR Antibody Homodimer, TTR Antibody Homotetramer, and TTR Fab Homotetramer Fusion Proteins The activity and PK profile of the parental anti-GITR mAb, anti-GITR TTR antibody homodimer, anti-GITR TTR antibody homotetramer, and anti-GITR TTR Fab homotetramer fusion proteins was evaluated.
Activity Evaluation The binding and potency activity of the parental anti-GITR mAb, anti-GITR TTR antibody homodimer, anti-GITR TTR antibody homotetramer, and anti-GITR TTR Fab homotetramer fusion proteins was evaluated via the following assays. Results from these assays are illustrated in FIG. 10.

Assay with cross-linking. 96-well high-binding plates (Corning 3369) were coated overnight at 4° C. with anti-CD3 Ab (OKT3) and cross-linker Ab (either goat anti-human IgG Fc Cross-Adsorbed Ab (Thermo Scientific 31125) or goat anti-human IgG (H+L) (Pierce 31119)) at 1 and 0.3 μg/ml respectively. The next day Abs were washed out and anti-GITR mAb, anti-GITR TTR antibody homodimer, anti-GITR TTR antibody homotetramer, anti-GITR TTR Fab homotetramer fusion proteins TTRs, or isotype control mAb was added to the plates for capture for 1 hr at 37° C. After incubation, the plates were washed out and naïve T cells were added to the wells (50K/well in RPMI1640 supplemented with 10% FBS, 2 mM L-Glut, 10 mM HEPES, 1 mM NaPyr, 0.1 mM NEAA, and 50 μM 2ME) and cultured for 4 days. Proliferation was measure using CellTiterGlo (Promega).

Assay without cross-linking. 96-well high-binding plates (Corning 3369) were coated overnight at 4° C. with anti-CD3 Ab at 1 μg/ml. The next day anti-CD3 Ab was washed out and anti-GITR mAb, anti-GITR TTR antibody homodimer, anti-GITR TTR antibody homotetramer, anti-GITR TTR Fab homotetramer fusion proteins TTRs, or isotype control mAb was added to the plates followed by addition of naïve T cells (50K/well in RPM11640 supplemented with 10% FBS, 2 mM L-Glut, 10 mM HEPES, 1 mM NaPyr, 0.1 mM NEAA, and 50 μM 2ME. After 4 days of culture proliferation was measure using CellTiterGlo (Promega).
PK Profile Evaluation PK profiles were determined by intravenous injection in male CD-1 mice (n=3 per group) molar equivalent normalized at 8.75 mg/kg of anti-GITR TTR antibody homotetramer, 4.75 mg/kg of anti-GITR TTR antibody homodimer, 3.4 mg/kg of anti-GITR TTR Fab homotetramer, and 2 mg/kg for the anti-GITR antibody. The serum samples were collected from 75 μl of blood samples collected at 0.5, 2, 8, 24, 48, 72, 96, 168, 336, 504, 672, and 840 hours post-dose. Each blood sample was maintained at room temperature after collection, and following a 30-40 minute clotting period, samples were centrifuged at 2-8° C. at 11,500 RPM for about 10 minutes using a calibrated Eppendorf 5417R Centrifuge System (Brinkmann Instruments, Inc., Westbury, NY). The collected serum was then transferred into a pre-labeled (for each rat), cryogenic storage tube and stored at −60° C. to −80° C. for future bioanalysis.

The following PK assay was used to measure total anti-GITR species (i.e., any anti-GITR binding species present) of the parental anti-GITR mAb, the anti-GITR TTR antibody homodimer, the anti-GITR TTR antibody homotetramer, and the anti-GITR TTR Fab homotetramer fusion proteins, in mouse serum by Meso Scale Discovery (MSD) assay. A regular binding 96 well MSD plate (Meso Scale Discovery, Gaithersburg, MD) was coated with 2 μg/ml of mouse anti-idiotypic anti-GITR antibody, Mab 1.2.1 (Amgen Inc., Thousand Oaks, CA) in PBS and then incubated overnight at 4° C. The plate was then washed and blocked with I-Block™ (Life Technologies, Carlsbad, CA) overnight at 4° C. The standards and quality controls (QC) were prepared in mouse serum, and PK samples were diluted in naïve CD-1 mouse serum if dilution was required. The standards, QCs, and samples were then diluted 1:20 in a buffer containing PBS, 1M NaCl, 0.5% Tween 20 and 1% bovine serum albumin. The plate was washed three times with approximately 200 μl of 1×KPL buffer (KPL, Gaithersburg, MD), and subsequently 50 μl samples of diluted standards, QCs, and samples were transferred into the Mab 1.2.1 antibody coated plate and incubated for 1.5 h at room temperature (approximately 25° C.). The plate was washed three times with approximately 200 μl of 1×KPL wash buffer, and then 50 μl of 250 ng/ml of mouse anti-idiotypic anti-GITR antibody, Mab 1.1.1 conjugated to biotin was added and incubated for 1.5 hr. After washing the plate three times with 1×KPL wash buffer, 50 µl of 100 ng/ml of Streptavidin conjugated to MSD SULFO-TAG (Amgen, Inc.) was added and incubated or 15 min. The plate was washed six times with approximately 200 µl of 1×KPL wash buffer, followed by addition of 150 µl 1× Read Buffer T (Meso Scale Discovery), and the electrochemiluminescent signal was measured using a MSD 6000 plate reader (Meso Scale Discovery). Serum concentration data were analyzed using non-compartmental methods with Phoenix® (Phoenix 64, Build 6.4.0.768, Pharsight® Corp. Mountain View, CA).

The following PK assay was used to measure the presence of both anti-GITR binding species and TTR species in the anti-GITR TTR antibody homodimer, anti-GITR TTR antibody homotetramer, and anti-GITR TTR Fab homotetramer fusion proteins in mouse serum by MSD assay of mouse serum samples. A regular binding 96 well MSD plate (Meso Scale Discovery, Gaithersburg, MD) was coated with 2 µg/ml of rabbit anti-TTR polyclonal antibody (Amgen Inc., Thousand Oaks, CA) in PBS and then incubated overnight at 4° C. The plate was then washed and blocked with I-Block™ (Life Technologies, Carlsbad, CA) overnight at 4° C. The standards and quality controls (QC) were prepared in mouse serum, and PK samples were diluted in naïve CD-1 mouse serum if dilution was required. The standards, QCs, and samples were then diluted 1:20 in a buffer containing PBS, 1M NaCl, 0.5% Tween 20 and 1% bovine serum albumin buffer. The plate was washed three times with approximately 200 µl of 1×KPL buffer (KPL, Gaithersburg, MD), and subsequently 50 µl samples of diluted standards, QCs, and samples were transferred into the anti-TTR antibody coated plate and incubated for 1.5 h at room temperature. The plate was washed three times with approximately 200 µl of 1×KPL wash buffer, and then 50 µl of 250 ng/ml of mouse anti-idiotypic anti-GITR antibody, Mab 1.1.1 conjugated to biotin was added and incubated for 1.5 hr. After washing the plate three times with 1×KPL wash buffer, 50 µl of 100 ng/ml of Streptavidin conjugated to MSD SULFO-TAG (Amgen, Inc.) was added and incubated or 15 min. The plate was washed six times with approximately 200 µl of 1×KPL wash buffer, followed by addition of 150 µl 1× Read Buffer T (Meso Scale Discovery), and the electrochemiluminescent signal was measured using a MSD 6000 plate reader (Meso Scale Discovery). Serum concentration data were analyzed using non-compartmental methods with Phoenix® (Phoenix 64, Build 6.4.0.768, Pharsight® Corp. Mountain View, CA).

The results of the PK analysis can be found in FIG. 9. As demonstrated by FIG. 9 a) (measure of any anti-GITR binding species present): [1] the PK of the anti-GITR TTR antibody homodimer ("1") is more desirable than the PK of the parental Ab ("2"); [2] the PK of the anti-GITR TTR Fab homotetramer ("4") is less desirable and this is likely attributed to the fact that the Fab lacks an Fc region and thus lacks the ability to mediate/extend its half-life; and [3] the PK of the anti-GITR TTR antibody homotetramer ("3"), although not as robust as the parental mAb, demonstrates significantly enhanced PK compared to the Fab. FIG. 9 b) (measure of presence of both anti-GITR binding species and TTR species) demonstrates that the PK of the intact anti-GITR TTR fusion proteins is in line with that observed in FIG. 9 a), indicating that in vivo proteolysis is not freeing the anti-GITR binding portion from each TTR fusion protein.

As demonstrated in FIG. 10, the multimerization—via TTR fusions—of the parental anti-GITR mAb 9H6 improves binding but not potency. It is known that activation of GITR prevents suppression by regulatory T cells. It is also known that clustering and FcγR binding is required for anti-GITR antibody mediated activation of cell proliferation, cytokine production and induction of CD4+Th9 cells. FIG. 10 a) indicates that the binding affinity of the anti-GITR TTR antibody homodimer ("3"), TTR antibody homotetramer ("4"), and TTR Fab homotetramer ("2") fusion proteins is more desirable than the parental anti-GITR mAb 9H6 ("1"). Notably, the higher affinity did not translate to higher potency in cell based assays, as demonstrated by FIG. 10 b). The Control Ab in FIG. 10 b) is a non-binding control version of the anti-GITR mAb.

A comparison of the data in FIGS. 9a and 9b indicates that there is little partial molecular degradation of the TTR constructs.

Example 6: Cloning, Expression, and Purification of Anti-TRAILR2 TTR Antibody Homodimer, TTR Antibody Homotetramer, and TTR Fab Homotetramer Fusion Proteins Cloning of Anti-TRAILR2 TTR Antibody Homodimer, TTR Antibody Homotetramer, and TTR Fab Homotetramer Fusion Proteins Anti-TRAILR2 TTR antibody homodimer, TTR antibody homotetramer, and TTR Fab homotetramer fusion proteins were generally cloned as follows. In these experiments, the anti-TRAILR2 antibody is conatumumab (AMG 655) and the anti-TRAILR2 Fab is a Fab portion of conatumumab.

The GITR TTR expression plasmids (see Example 4) were used as templates for construction of these anti-TRAILR2 TTR fusions. Constructs C36606 (pTT5:Native:: [hu anti-<huTRAILR2> XG1048 (W) VH]::huIgG1(f)) and C9448 (VK3_A27L::[hu anti-<huTRAILR2> XG1048 VL]::huKLC) were the templates used for the anti-TRAILR2 heavy chain and light chain variable region sequences, respectively. In these experiments, the anti-TRAILR2 antibody is conatumumab (AMG 655). Since the anti-TRAILR2 sequence template did not have a VK1 (VK1O2O12) signal peptide pSLX240puro, pSLX240hygro, and pSLX240neo constructs were found that contain VK1 with a BssHII site on the carboxy terminus of the signal peptide sequence.

[SEQ ID NO: 31]$_2$-[SEQ ID NO: 1]$_4$ was assembled as follows. PCR31: using C36606 as template, a 5' PCR primer encoding the amino terminus of the heavy chain sequence and the VK1 (VK1O1O12) signal sequence (5'-CTG CTG TGG CTG AGA GGT GCG CGC TGT CAG GTG CAG CTG CAG GAG-3' (SEQ ID NO: 113)), in combination with a 3' primer, designed to amplify the anti-TRAILR2 variable heavy chain region (5'-GCT GAG GAG ACG GTG ACC GT-3' (SEQ ID NO: 114)). PCR31 resulted in a 395 base pair product. PCR 32: using C-143043 as a template, a 5' primer encodes the amino terminus of the heavy chain constant region and the last 18 bases of the anti-TRAILR2 variable heavy chain (5'-GGT CAC CGT CTC CTC AGC TAG CAC CAA GGG CCC A-3' (SEQ ID NO: 115)) in combination with a 3' primer, encoding the carboxyl terminus of TTR, a termination codon, NotI site, and an 18 base overhang encoding the amino terminus of the linearized pSLX240p plasmid (5'-TTA AAC GAT ATC GCT AGC GCG GCC GCT CAT TCC TTG GGA TTG GTG ACG-3' (SEQ ID NO: 116). PCR 32 resulted in a 1390 base product. PCR reactions 31 and 32 were purified over a Qiagen column. These fragments were then combined with a pSLX240p:VK1 plasmid linearized at BssHII and NotI sites in a ligation independent cloning reaction (Geneart Seamless Cloning and Assembly Kit). The resulting construct was termed C-150225: pSLX240p:VK1O2O12::[hu anti-<huTRAILR2> AMG 655 VH]::IgG1z_SEFL(desK)::TTR (C10A,K15A).

SEQ ID NO:38 was assembled as follows. PCR33: using C9448 as template, a 5' PCR primer encoding the amino terminus of the anti-TRAILR2 light chain variable region and the signal sequence (5'-CTG CTG TGG CTG AGA GGT GCG CGC TGT GAA ATT GTG TTG ACG CAG-3' (SEQ ID NO: 117)), in combination with a 3' primer (5'-AGC CAC CGT TCG TTT GAT TTC CAC CTT-3' (SEQ ID NO: 118)) amplifies the anti-TRAILR2 light chain variable region to produce a 363 base pair product. PCR34, using C-143044 (pTT5d:VK1O2O12:: [hu anti-<huGITR> 9H6 VL]) as a template, a 5' primer encoding the amino terminus of the kappa light chain constant region and the last 9 bases of the anti-TRAILR2 variable region (5'-ATC AAA CGA ACG TGT GCT GCA CCA TCT-3' (SEQ ID NO: 119)), in combination with a 3' primer encoding the carboxyl terminus of the human kappa light chain constant region, termination codon, and NotI restriction enzyme (5'-TGT TTA AAC GAT ATC GCT AGC GCG GCC GCC TAA CAC TCT CCC CTG TTG AAG-3' (SEQ ID NO: 120)). PCR34 produced an approximately 330 base pair product. PCR reactions 33 and 34 were purified over a Qiagen column. These fragments were then combined with a pSLX240h:VK1 plasmid linearized at BssHII and NotI sites in a ligation independent cloning reaction (Geneart Seamless Cloning and Assembly Kit). The resulting construct was termed C-150226: pSLX240h:VK1O2O12::[hu anti-<huTRAILR2> AMG655 VL]::huKLC.

[SEQ ID NO: 32]$_4$-[SEQ ID NO: 1]$_4$ was assembled as follows. PCR 31 was utilized as described above. PCR35: using C-144127 as a template, a 5' primer encoding the amino terminus of the heavy chain constant region and the last 18 bases of the anti-TRAILR2 heavy chain variable region (5'-GGT CAC CGT CTC CTC AGC CTC CAC CAA GGG CCC C-3' SEQ ID NO: 121)) in combination with a 3' primer encoding the carboxyl terminus of the TTR (5'-TTAAACGATATCGCTAGCGCGGCCGCTCAT-TCCTTGGGATTGGTGACG-3' (SEQ ID NO: 121)) produces an approximately 1390 base pair product. PCR reactions 31 and 35 were purified over a Qiagen column. These fragments were then combined with a pSLX240p: VK1 plasmid linearized at BssHII and NotI sites in a ligation independent cloning reaction (Geneart Seamless Cloning and Assembly Kit). The resulting construct was termed C-150227: pSLX240p:VK1O2O12::[hu anti-<huTRAILR2> AMG 655 VH]:: IgG1z(N297G,KK)::TTR (C10A,K15A).

SEQ ID NO: 33 was assembled as follows. PCR31 was utilized as described above. PCR36: using C-144130 as a template, a 5' primer (5'-GGT-CACCGTCTCCTCAGCCTCCACCAAGGGCCCC-3' (SEQ ID NO: 121)) in combination with a 3' primer encoding the carboxyl terminus of the heavy chain constant region, termination codon, and NotI site (5'-TTA AAC GAT ATC GCT AGC GCG GCC GCT CAA CCC GGG GAG AGG CTC A-3' (SEQ ID NO: 122)) resulted in an approximately 1 kb size product. PCR reactions 31 and 36 were purified over a Qiagen column. These fragments were then combined with a pSLX240n:VK1 plasmid linearized at BssHII and NotI sites in a ligation independent cloning reaction (Geneart Seamless Cloning and Assembly Kit). The resulting construct was termed C-150228: pSLX240n: VK1O2O12::[hu anti-<huTRAILR2> AMG 655 VH]:: IgG1z(N297G,DD).

[SEQ ID NO: 34]$_4$-[SEQ ID NO: 1]$_4$ was assembled as follows. PCR31 was utilized as described above. PCR37: using C144132 as a template, a 5' primer (5'-GGT-CACCGTCTCCTCAGCTAGCACCAAGGGCCCA-3' (SEQ ID NO: 115)) in combination with a 3' primer encoding a 6×His, termination codon, and NotI site (5'-TTA AAC GAT ATC GCT AGC GCG GCC GCC TAG TGG TGA TGG TGA TGG TGA CC-3' (SEQ ID NO: 123)) produced an approximately 740 base pair product. PCR reactions 31 and 37 were purified over a Qiagen column. These fragments were then combined with a pSLX240p:VK1 plasmid linearized at BssHII and NotI sites in a ligation independent cloning reaction (Geneart Seamless Cloning and Assembly Kit). The resulting construct was termed C-150237: pSLX240p:VK1O2O12::[hu anti-<huTRAILR2> AMG 655 (S183E) scFab]::G2::TTR (C10A,K15A)::G2::6×His (note that the (His)$_6$ tag was included for purification purposes).

SEQ ID NO: 39 was assembled as follows. PCR33 was utilized as described above. PCR38: using C-143049 as template, a 5' primer (6186-65) in combination with a 3' primer encoding the carboxyl terminus of the kappa light chain constant region, termination codon, and NotI site (5'-TGT TTA AAC GAT ATC GCT AGC GCG GCC GCT CAA CAC TCT CCC CTG TTG AA-3' (SEQ ID NO: 124)) produced an approximately 330 base pair product. PCR reactions 33 and 38 were purified over a Qiagen column. These fragments were then combined with a pSLX240h: VK1 plasmid linearized at BssHII and NotI sites in a ligation independent cloning reaction (Geneart Seamless Cloning and Assembly Kit). The resulting construct was termed C-150238: pSLX240h:VK1O2O12::[hu anti-<huTRAILR2> AMG 655 VL]::huKLC-S176K.

Expression of Anti-TRAILR2 TTR Antibody Homodimer, TTR Antibody Homotetramer, and TTR Fab Homotetramer Fusion Proteins The anti-TRAILR2 TTR antibody homodimer, TTR antibody homotetramer, and TTR Fab homotetramer fusion proteins were generally expressed as follows.

The TTR fusion proteins were stably expressed in suspension adapted CHO-K1 cells. Transfections were performed using Lipofectamine LTX (Invitrogen™) according to the manufacturer's protocol. A total of 30-36 µg of the mammalian expression plasmid DNA was used at a 1:1 ratio for the anti-TRAILR2 TTR antibody homodimer and TTR Fab homotetramer (1 HC or Fab-HC to 1 LC), or 1:1:1 ratio for the TTR antibody homotetramer (1 HC+ to 1 HC– to 1 LC). For each, the plasmid DNA was added to 3-4 ml OPTI-MEM (Gibco) and mixed. In a separate tubes, 72-75 µl Lipofectamine LTX was added to 3-4 ml OPTI-MEM. The solutions were incubated for 5 minutes at room temperature. To form the transfection complex, the DNA and Lipofectamine LTX mixtures for each were combined and incubated at room temperature for an additional 20 minutes. Log phase CHO-K1 cells were pelleted by centrifugation (1200-1500 RPM for 5 minutes), washed one time with 1×PBS (Gibco) and resuspended to 1.5-2e$^6$ viable cells/mL in OPTI-MEM. For each transfection, 5-6 mL of the washed cells were added to a 125 mL volume shake flask. The DNA transfection complex was added to the cells for each. The flasks were incubated at 36° C., 5% CO$_2$, shaking at 150 RPM for 6 hours. To stop the transfection, 9-12 ml growth media was added to each flask and incubated for 48-72 hours.

To begin selection, cells were pelleted by centrifugation (1200-1500 RPM for 5 minutes) 72 hours post-transfection and the media was replaced with 23-25 mL of growth media supplemented with antibiotics. Selection media was changed 2-3 times per week, diluting cultures when needed to ensure cultures did not over-grow (<5-6 $e^6$ vc/mL), until cell viability and density recovered.

Large scale productions (2.3 L-2.5 L) were carried out in shake flasks at 36° C. Productions were seeded at $2e^6$ vc/mL in production media. Conditioned media was harvested on day 5 by centrifugation followed by filtration (0.45 m).

Figure 11:
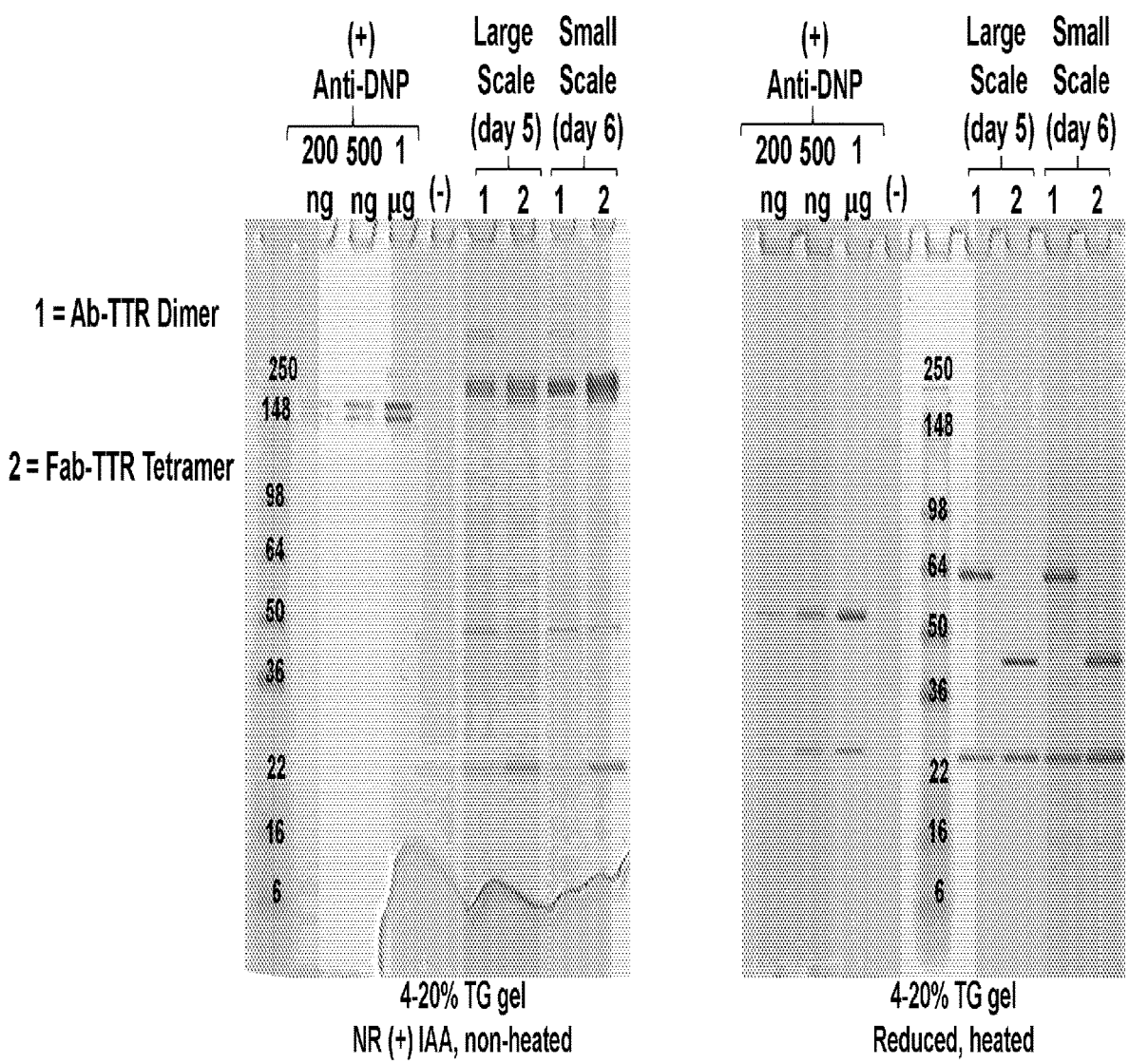
FIG. 11 is a series of SDS-PAGE gels that demonstrate that the anti-TRAILR2 TTR antibody homodimer (1) and anti-TRAILR2 TTR Fab homotetramer (2) proteins, respectively, are expressed well and assemble correctly in mammalian cells.

As demonstrated in FIG. 11, the anti-TRAILR2 TTR antibody homodimer and TTR Fab homotetramer fusion proteins express well and assemble correctly (see FIG. 11 a)). FIG. 11 b) demonstrates that the expected fusion protein components are present upon heating and reduction. 5 µl of condition media was loaded per lane and was run on a 4-20% TG gel. As seen in FIG. 11 a), the anti-TRAILR2 TTR antibody homodimer and TTR Fab tetramer migrate on SDS-PAGE as a complexes larger than a standard antibody as expected for fully assembled complexes. As seen in FIG. 11 b), the anti-TRAILR2 TTR antibody homodimer and TTR Fab homotetramer migrate on reduced SDS-PAGE as expected for the fusion molecules with the heavy chains (upper bands) as well as the free light chains (lower bands).

Figure 12:
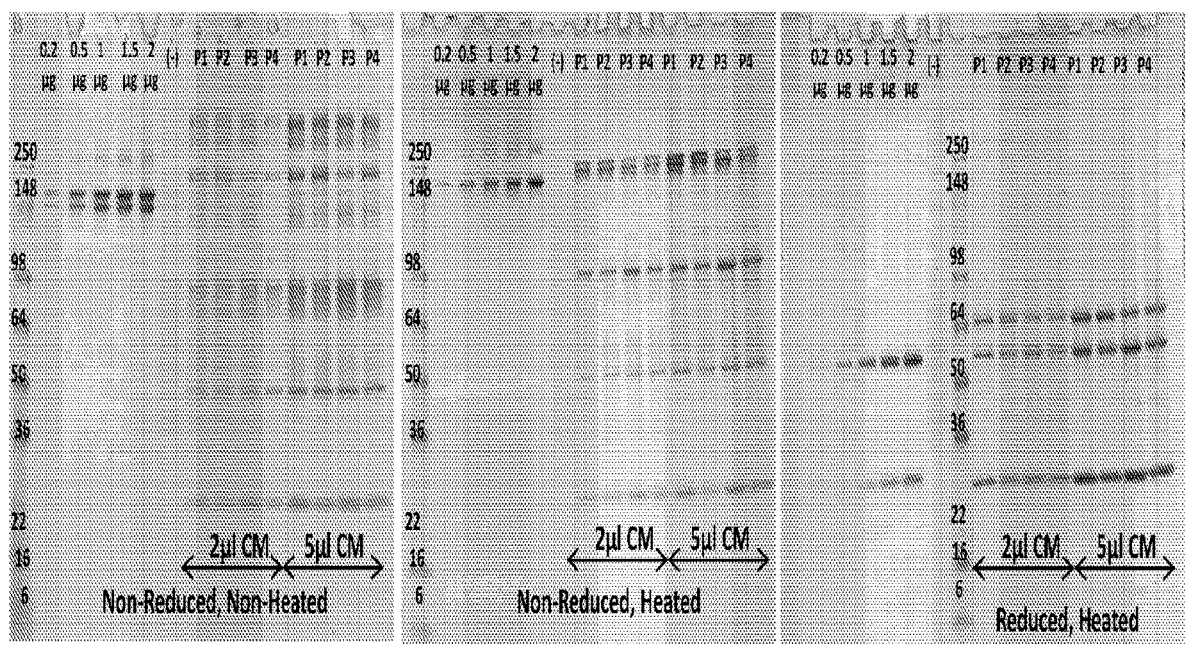
FIG. 12 is a series of SDS-PAGE gels that demonstrate that the anti-TRAILR2 TTR antibody homotetramer is expressed well and assembles correctly in CHO-K1 cells.

As demonstrated in FIG. 12, the anti-TRAILR2 TTR antibody homotetramer expresses well (at ~150 mg/L) and assembles correctly in CHO-K1 cells (see FIG. 12 a), top bands). FIG. 12 b) shows that the homotetramer complexes are broken down into their expected components upon heating, while FIG. 12 c) shows that the homotetramer complexes are broken down into their expected components upon heating and reduction. 2-5 µl of condition media was loaded per lane and was run on a 4-20% TG gel.

FIG. 13 shows that the anti-TRAILR2 TTR Fab homotetramer, anti-TRAILR2 TTR antibody homodimer, and anti-TRAILR2 TTR antibody homotetramer are correctly assembled and that, upon heating and reduction, the molecules break down to their expected component chains (upper band(s) are heavy chains and lowest band is light chain). FIG. 13 demonstrates that the TTR constructs can be generated with a variety of antibodies.

Purification and Characterization of Anti-TRAILR2 TTR Antibody Homodimer, TTR Antibody Homotetramer, and TTR Fab Homotetramer Fusion Proteins The anti-TRAILR2 TTR antibody homodimer and TTR antibody homotetramer fusion proteins were generally purified as follows. The molecules were purified from cell culture media using an AKTA Purifier (GE Healthcare Life Sciences) liquid chromatography system with two, sequentially linked 5 mL ProA FF HiTrap (GE Healthcare Life Science) columns. The media was loaded directly onto the ProA FF columns, then washed with 5 CV of DPBS (Life Technologies) and eluted with 8 CV of 50 mM acetic acid, pH 3.2. The ProA FF elution pools were titrated to pH 5.0 using 2 M Tris-HCl, pH 9.2, then diluted with nine volumes of sterile water. The conditioned ProA FF pools were dialyzed against 2 L of 20 mM HEPES, 150 mM NaCl, pH 7.0, twice, using 10 kDa MWCO Slide-a-lyzers (Thermo Fisher Scientific). The dialyzed pools were purified on an 18 mL SP Sepharose High Performance (SP HP) (GE Healthcare Life Science) column, employing a 5 CV wash with 20 mM NaH2PO4, pH 7.0 and eluted with a 20 CV NaCl gradient from 0 mM to 500 mM. Fractions were selected for pooling by SDS-PAGE and HPLC-SEC purity. The SP HP pools were concentrated using VivaSpin 10 kDa MWCO centrifugal filtration units (Sartorius, Gottingen, Germany) and then purified on a 320 mL Superdex 200 (GE Healthcare Life Science) isocratically over 1.4 CV of 20 mM HEPES, 300 mM NaCl, pH 7.0. Fractions were selected for pooling by SDS-PAGE and HPLC-SEC purity. The SP HP pools were dialyzed against 2 L of 10 mM MES, 150 mM NaCl, pH 7.0, twice, using 10 kDa MWCO Slide-a-lyzers (Thermo Fisher Scientific). The dialyzed samples were concentrated using VivaSpin 10 kDa MWCO centrifugal filtration units (Sartorius) and then sterile filtered through 0.2 m Supor syringe filters (Pall).

The anti-TRAILR2 Fab homotetramer fusion proteins were generally purified as follows. The molecule was purified from cell culture media using an AKTA Purifier (GE Healthcare Life Sciences) liquid chromatography system with a 50 mL Ni Sepharose excel (Ni excel) (GE Healthcare Life Sciences) column. The media was loaded directly onto the HisTrap column, then washed with 10 CV of 20 mM $NaH_2PO_4$, 0.5 M NaCl, 10 mM imidazole, pH 7.4 and eluted with 8 CV imidazole gradient from 10 mM to 500 mM. The Ni excel pool was dialyzed against 2 L of 20 mM HEPES, 150 mM NaCl, pH 7.0, twice, using 10 kDa MWCO Slide-a-lyzers (Thermo Fisher Scientific). The dialyzed pools were purified on an 18 mL SP Sepharose High Performance (SP HP) (GE Healthcare Life Science) column, employing a 5 CV wash with 20 mM NaH2PO4, pH 7.0 and eluted with a 20 CV NaCl gradient from 0 mM to 500 mM. Fractions were selected for pooling by SDS-PAGE and HPLC-SEC purity. The SP HP pool was dialyzed against 2 L of 10 mM MES, 150 mM NaCl, pH 7.0, twice, using a 10 kDa MWCO Slide-a-lyzer (Thermo Fisher Scientific). The dialyzed sample was concentrated using a VivaSpin 10 kDa MWCO centrifugal filtration unit (Sartorius) and then sterile filtered through a 0.2 µm Supor syringe filter (Pall). The protein concentration was determined by UV absorbance at 280 nM (A280) using a NanoDrop 2000 (Thermo Fisher Scientific, Rockford, Illinois, USA). Samples were analyzed by denaturing, non-reducing 4-12% Bis-Tris NuPAGE gel using MES running buffer (Life Technologies, Carlsbad, California, USA), per manufacturer instructions. Samples were analyzed on a Phenomenex SEC 3000 column, 7.8× 300 mm (Phenomenex, Torrance, California, USA) in 50 mM NaH2PO4, 250 mM NaCl, pH 6.9 at 1 mL/min observing the absorbance at 280 nm.

Figure 14:
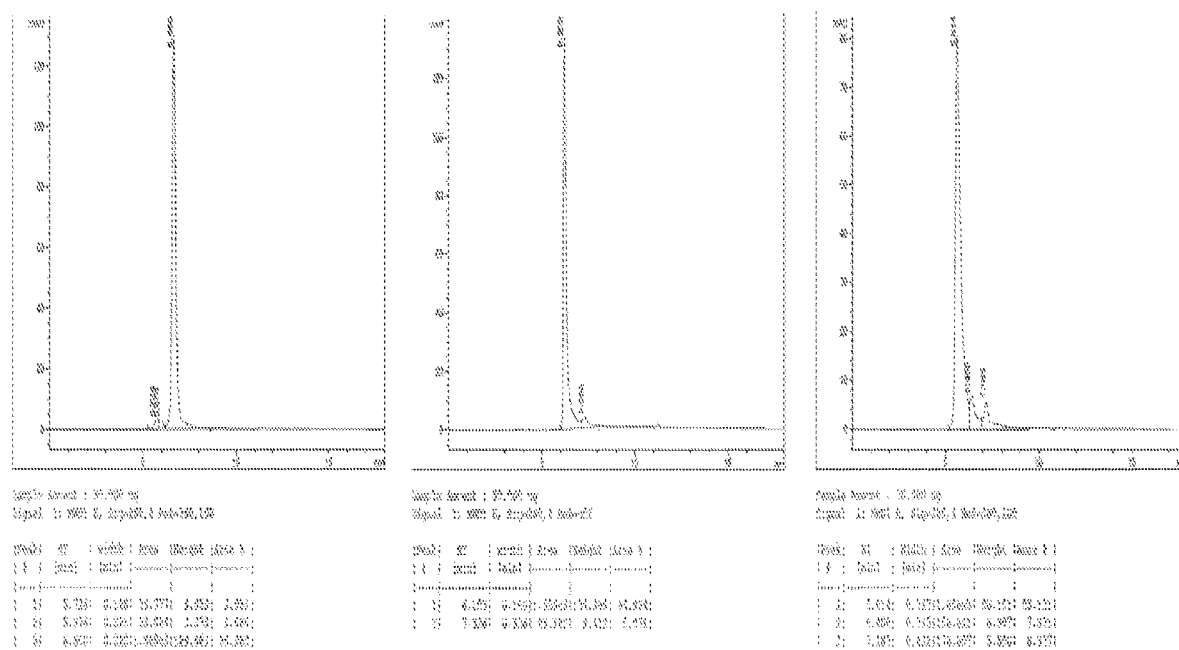
FIG. 14 is an HPLC SEC analysis of each of the anti-TRAILR2 TTR antibody homodimer (middle chromatogram), TTR antibody homotetramer (right chromatogram), and TTR Fab homotetramer (left chromatogram) fusion proteins.

FIG. 14 shows the results of the HPLC size exclusion chromatography (SEC) analysis of each of the anti-TRAILR2 TTR antibody homodimer (middle chromatogram), TTR antibody homotetramer (right chromatogram), and TTR Fab homotetramer (left chromatogram) fusion proteins. The SEC chromatograms demonstrate that the main peak elutes at the expected position consistent with correctly assembled molecules.

Reduced LC/MS analysis of the anti-TRAILR2 TTR antibody homodimer, TTR antibody homotetramer, and TTR Fab homotetramer fusion proteins was performed. Samples were buffer exchanged into 200 mM ammonium acetate and made to 5 M as a final MS-working solution for native MS studies. Samples were also denatured in 8M guanidine HCl and reduced in 20 mM DDT for LC-MS analysis. 2 µg of material was then injected on to the LC-MS system.

Native MS and Ion Mobility Analysis of the anti-TRAILR2 TTR antibody homodimer, TTR antibody homotetramer, and TTR Fab homotetramer fusion proteins was performed on an RF-confining drift-tube using a modified Synapt G1 HDMS instrument, which was operated in positive nanoflow ESI mode. Critical instrument voltages and pressures were as follows: capillary voltage 0.8 to 1.0 kV; sample cone 40 V, extraction cone 1 V; source block temperature 30° C.; trap collision energy 4.0 V; transfer collision energy 60 to 200 V, corresponding to 3.3 V to 11.1 V/cm applied across the RF-confining drift cell; trap entrance 3.0 V; trap bias 16 V (N2; an increased potential is required to inject the ions in the drift cell when operated with N2); IMS DC entrance 5.0 V; IMS DC exit 0.0 V; transfer DC entrance 0.0 V; transfer DC exit 2.0 V; transfer wave velocity 70 m/sec; transfer wave amplitude 4.0 V; mobility trapping release time 250 sec; trap height 20.0 V; extract height 0.0 V; source RF amplitude (peak-to-peak) 450 V; triwave RF amplitudes (peak-to-peak), trap 380 V, IMS 150 V, transfer 380 V; source backing pressure 6.0 mbar; trap/transfer pressure SF6, $3.3e^{-2}$ mbar (Pirani gauge indicated; flow rate 3.0 mL/min); IMS pressure N2 2.05 mbar (1.54 Torr; flow rate 38 mL/min); IMS pressure He 2.70 mbar (2.03 Torr; flow rate 70 mL/min). The pressure within the RF-confining drift cell was accurately measured using an MKS Baratron capacitance manometer, type 626 (range 10 Torr; accurate to 0.25%) and an MKS PDR2000 power supply. Ambient temperature was measured using an Oakton Temp10T thermocouple. The temperature was measured at the point where the capacitance manometer is connected to the instrument ion optics lid. Instrument control and data acquisition was carried out through MassLynx 4.1 SCN 639, SCN744. The mobilities and, therefore, the 2 values were made by accurately measuring the pressure within the drift-cell device and the ambient temperature of drift cell and making up to 10 mobility measurements at different drift-cell voltages (60 V to 200 V). Individual temperature and pressure measurements were taken for each acquisition, and for the final $\Omega$ value calculation, an average temperature and pressure value was used. Typical temperature and pressure variations over 10 minutes were $\leq 0.2°$ C. and $\leq 0.002$ Torr.

Denaturing LC-MS analysis of the anti-TRAILR2 TTR antibody homodimer, TTR antibody homotetramer, and TTR Fab homotetramer fusion proteins was performed was carried by injecting 2 μg of denatured and reduced protein directly on to a C4 BEH 2.1×50 mm analytical column operated at 45° C. and a flow rate of 400 L/min. MS-detection was performed on a Waters XevoQ-ToF mass spectrometer. The sample cone and extraction cone were set to 35 V and 1 V respectively.

Mass Spectrometric and Ion Mobility Results: anti-TRAILR2 TTR antibody homotetramer: native-MS measured MW was 645.9 kDa, and the ion mobility measured N2-CCS value was 190.1 nm2, and the denatured and reduced MW of subunits was 23,388 Da, 49,180 Da and 62,872 Da. Anti-TRAILR2 TTR Fab homotetramer fusion protein: native-MS measured MW was 250.5 kDa, and the ion mobility measured N2-CCS value was 130.3 nm2, and the denatured and reduced MW of the subunits was 23,429 Da and 38,582 Da. Anti-TRAILR2 TTR antibody homodimer fusion protein native-MS measured MW was 347.2 kDa, and the ion mobility measured N2-CCS value was 124.0 nm2, and the denatured and reduced MW of the subunits was 23,391 Da and 62,867 Da.

SEC-Multiple Angle Light Scattering (MALS) of the anti-TRAILR2 TTR antibody homodimer, TTR antibody homotetramer, and TTR Fab homotetramer fusion proteins was performed on an Agilent 1100 HPLC equipped with Wyatt Heleos II and OptiLab-TrEX detectors. The column used was Superdex 200 (10/300GL). The mobile phase was 2×PBS with a flow rate of 0.4 ml/min. Run time was 70 minutes per sample. Injection amounts for the four SP fractions of the anti-TRAILR2 TTR antibody homodimer and TTR antibody homotetramer fusion proteins (A3, A8, A12 and C1) were 81, 63, 75 and 75 μg, respectively, while the injection amount for the final pool of anti-TRAILR2-TTR was 77 ug. Run setup, data collection and analysis procedures were performed on Agilent's Chemstation (v B.04.02 96) and Wyatt's ASTRA (v 6.1.1.17) software.

Example 7: Activity and PK Profile of Anti-TRAILR2 TTR Antibody Homodimer, TTR Antibody Homotetramer, and TTR Fab Homotetramer Fusion Proteins The activity and PK profile of the parental anti-TRAILR2 mAb (conatumumab), anti-TRAILR2 TTR antibody homodimer, anti-TRAILR2 TTR antibody homotetramer, and anti-TRAILR2 TTR Fab homotetramer fusion proteins was evaluated.

PK Profiles

The PK profiles of the anti-TRAILR2 TTR antibody homodimer, TTR antibody homotetramer, and TTR Fab homotetramer fusion proteins were determined by intravenous injection in male CD-1 mouse (n=3 per group) molar equivalent normalized at 6.5 mg/kg of TTR antibody homotetramer, 3.5 mg/kg of TTR antibody homodimer, 2.5 mg/kg of TTR Fab homotetramer, and 1.5 mg/kg for the conatumumab and conatumumab-341-G1 (conatumumab-341-G1 is an Ab engineered to no longer bind TRAILR2) antibodies. Serum samples were collected from 75 μl of blood samples collected at 0.5, 2, 8, 24, 48, 72, 96, 192, 336, 504, 672, and 840 hours post-dose. Each blood sample was maintained at room temperature after collection, and following a 30-40 minute clotting period, samples were centrifuged at 2-8° C. at 11,500 rpm for about 10 minutes using a calibrated Eppendorf 5417R Centrifuge System (Brinkmann Instruments, Inc., Westbury, NY). The collected serum was then transferred into a pre-labeled (for each rat), cryogenic storage tube and stored at −60° C. to −80° C. for future bioanalysis.

The following PK assay was used to measure total anti-TRAILR2 species (i.e., any anti-TRAILR2 binding species present) of conatumumab, the anti-TRAILR2 TTR antibody homodimer, anti-TRAILR2 TTR antibody homotetramer, and anti-TRAILR2 TTR Fab homotetramer fusion proteins, in mouse serum by Meso Scale Discovery (MSD) assay. To measure the total amount of conatumumab in mouse serum samples, a regular binding 96 well MSD plate (Meso Scale Discovery, Gaithersburg, MD) was coated with 2 μg/ml of rabbit anti-conatumumab polyclonal antibody (Amgen Inc., Thousand Oaks, CA) in PBS and then incubated overnight at 4° C. The plate was then washed and blocked with I-Block™ (Life Technologies, Carlsbad, CA) overnight at 4° C. The standards and quality controls (QC) were prepared in mouse serum, and PK samples were diluted in naïve CD-1 mouse serum if dilution was required. The standards, QCs, and samples were then diluted 1:20 in a buffer containing PBS, 1M NaCl, 0.5% Tween 20 and 1% bovine serum albumin. The plate was washed three times with approximately 200 μl of 1×KPL buffer (KPL, Gaithersburg, MD), and subsequently 50 μl samples of diluted standards, QCs, and samples were transferred into the anti-conatumumab antibody coated plate and incubated for 1.5 h at room temperature (approximately 25° C.). The plate was washed three times with approximately 200 μl of 1×KPL wash buffer, and then 50 μl of 100 ng/ml of mouse anti-hu Fc antibody, clone 1.35.1, conjugated to MSD SULFO-TAG (Amgen Inc., Thousand Oaks, CA) in I-Block™ containing 5% BSA was added and incubated for 1.5 h at room temperature. For the anti-TRAILR2 TTR Fab homotetramer construct, 50 μl of 250 ng/ml of the mouse anti-kappa LC, clone KCF-9 conjugated to biotin was added and incubated for 1.5 hr; then, after washing the plate with 1×KPL wash buffer, 50 μl of 100 ng/ml of Streptavidin conjugated to MSD SULFO-TAG (Amgen, Inc.) was added and incubated or 15 min. The plate was then washed six times with approximately 200 μl of 1×KPL wash buffer, followed by addition of 150 μl 1× Read Buffer T (Meso Scale Discovery), and the electrochemiluminescent signal was measured using a MSD 6000 plate reader (Meso Scale Discovery). Serum concentration data were analyzed using non-compartmental methods with Phoenix® (Phoenix 64, Build 6.4.0.768, Pharsight® Corp. Mountain View, CA).

The following PK assay was used to measure the presence of both anti-TRAILR2 TTR binding species and TTR species in the anti-TRAILR2 TTR antibody homodimer, anti-TRAILR2 TTR antibody homotetramer, and anti-TRAILR2 TTR Fab homotetramer fusion proteins in mouse serum by MSD assay of mouse serum samples. A regular binding 96 well MSD plate (Meso Scale Discovery, Gaithersburg, MD) was coated with 2 μg/ml of rabbit anti-TTR polyclonal antibody (Amgen Inc., Thousand Oaks, CA) in PBS and then incubated overnight at 4° C. The plate was then washed and blocked with I-Block™ (Life Technologies, Carlsbad, CA) overnight at 4° C. The standards and quality controls (QC) were prepared in mouse serum, and PK samples were diluted in naïve CD-1 mouse serum if dilution was required. The standards, QCs, and samples were then diluted 1:20 in a buffer containing PBS, 1M NaCl, 0.5% Tween 20 and 1% bovine serum albumin buffer. The plate was washed three times with approximately 200 μl of 1×KPL buffer (KPL, Gaithersburg, MD), and subsequently 50 μl samples of diluted standards, QCs, and samples were transferred into the anti-TTR antibody coated plate and incubated for 1.5 h at room temperature. The plate was washed three times with approximately 200 μl of 1×KPL wash buffer, and then 50 μl of 250 ng/ml of rabbit anti-conatumumab polyclonal antibody conjugated to biotin was added and incubated for 1.5 hr. After washing the plate three times with 1×KPL wash buffer, 50 μl of 100 ng/ml of Streptavidin conjugated to MSD SULFO-TAG (Amgen, Inc.) was added and incubated or 15 min. The plate was washed six times with approximately 200 μl of 1×KPL wash buffer, followed by addition of 150 μl 1× Read Buffer T (Meso Scale Discovery), and the electrochemiluminescent signal was measured using a MSD 6000 plate reader (Meso Scale Discovery). Serum concentration data were analyzed using non-compartmental methods with Phoenix® (Phoenix 64, Build 6.4.0.768, Pharsight® Corp. Mountain View, CA).

The results of the PK analysis can be found in FIG. 15. As demonstrated by FIG. 15 a) (measure of any anti-TRAILR2 binding species): [1] the PK of the anti-TRAILR2 TTR antibody homodimer ("1") is better than the PK of the parental Ab (conatumumab ("3"); and conatumumab-341-G1 ("2")); [2] the PK of the anti-TRAILR2 TTR Fab homotetramer ("5") is poor and this is likely attributed to the fact that the Fab lacks an Fc region and thus lacks the ability to mediate/extend its half-life; and [3] the PK of the anti-TRAILR2 TTR antibody homotetramer ("4") is similar to that of the parental mAb (conatumumab). Notably, the anti-TRAILR2 TTR antibody homotetramer demonstrates a much better PK compared to its parent (conatumumab), which differs from that observed with respect to the anti-GITR TTR antibody homotetramer (which was not as robust as the parental mAb, though it still demonstrated significantly enhanced PK compared to the Fab). This observation suggests that the PK of TTR antibody homotetramer fusion proteins may be antibody and/or target dependent. FIG. 15 b) (measure of both anti-TRAILR2 TTR binding species and TTR species) demonstrates that the PK of the intact anti-TRAILR2 TTR fusion proteins is in line with that observed in FIG. 15 a), indicating that in vivo proteolysis is not freeing the anti-TRAILR2 binding portion from each TTR fusion protein. The anti-TRAILR2 TTR antibody homodimer ("1"); anti-TRAILR2 TTR antibody homotetramer ("2"); and anti-TRAILR2 TTR Fab homotetramer ("3") are evaluated in FIG. 15 b).

Cell-Based Activity Assays

The activity of the anti-TRAILR2 TTR fusion proteins vs. conatumumab+Protein G on the melanoma cell line WM35 (ATCC) was evaluated. WM35 expresses DR5 but not DR4, was evaluated. TRAIL activates both DR5 and DR4. WM35 cells were plated at $10^4$ cells per well of a microtiter plate, and then incubated with conatumumab, anti-TRAILR2 TTR antibody homodimer, anti-TRAILR2 TTR antibody homotetramer, or anti-TRAILR2 TTR Fab homotetramer fusion proteins in the absence or presence of 1 g/ml Protein G (Pierce) to promote crosslinking. Triplicate samples were analyzed. After 24 h incubation at 37° C., 5% $CO^2$, cell viability was assessed using a Cell Titer-glo assay (Promega). The Cell Titer-glo reaction was carried out according to the manufacturer's instructions, and luminescence was measured using a Perkin Elmer Envision. The y-axis shows the luminescent signal as relative light units (RLU); decreased RLU reflects a decrease in ATP production and decreased number of viable cells. The x-axis shows the protein concentration.

Figure 16:
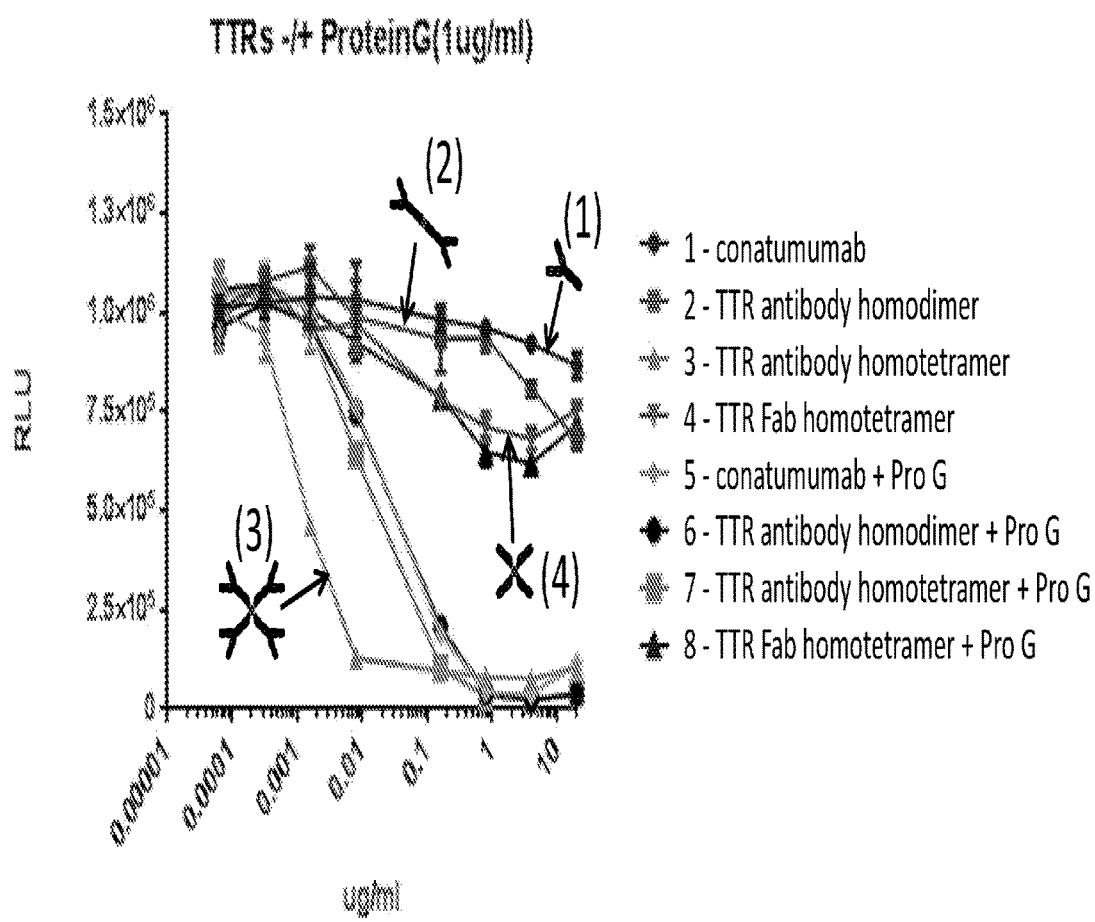
FIG. 16 shows the potency of the anti-TRAILR2 TTR fusion proteins compared to the parental mAb (conatumumab) in a WM35 cell killing assay.

FIG. 16 illustrates the results of the WM35 assay. Conatumumab ("1") is ineffective at killing cells, unless it is clustered with Protein G (which has two Ig binding sites; "5"). The anti-TRAILR2 TTR antibody homodimer ("2") is slightly better that killing WM35 cells than the parent conatumumab. The anti-TRAILR2 TTR Fab homotetramer ("4") has slightly better WM35 cell killing ability than conatumumab. However, the anti-TRAILR2 TTR antibody homotetramer ("3") is significantly more potent than conatumumab at killing WM35 cells and is even more potent than the conatumumab/Protein G clustered complex. In addition, clustering of the anti-TRAILR2 TTR antibody homodimer ("6") with Protein G improved potency of the fusion proteins, while clustering of the anti-TRAILR2 TTR Fab homotetramer with Protein G ("8") had little effect. Interestingly, clustering of the anti-TRAILR2 TTR antibody homotetramer with Protein G ("7") slightly impaired the protein fusion's potency. These results demonstrate that TTR antibody homotetramer-mediated clustering can enhance anti-tumor activity.

The activity of the anti-TRAILR2 TTR fusions vs. conatumumab+Protein G on primary human keratinocytes (Lonza) was also evaluated. Primary keratinocytes were plated at $10^4$ cells per well of a microtiter plate, and then incubated with TRAIL alone, conatumumab with 1 μg/ml Protein G (Pierce) to promote crosslinking, or TRAIL plus 1 μg/ml conatumumab. Samples were prepared in triplicate for each condition. After 24 h incubation at 37° C., 5% CO2, cell viability was assessed using a Cell Titer-glo assay (Promega). Primary keratinocytes were also plated at $10^4$ cells per well of a microtiter plate, and then incubated with anti-TRAILR2 TTR antibody homotetramer, anti-TRAILR2 TTR Fab homotetramer, conatumumab, or TRAIL at the concentrations indicated. TRAIL combined with 1 g/ml conatumumab was also tested. Samples were prepared in triplicate. After 24 h incubation at 37° C., 5% $CO_2$, cell viability was measured using a Cell Titer-glo assay (Promega).

Figure 17:
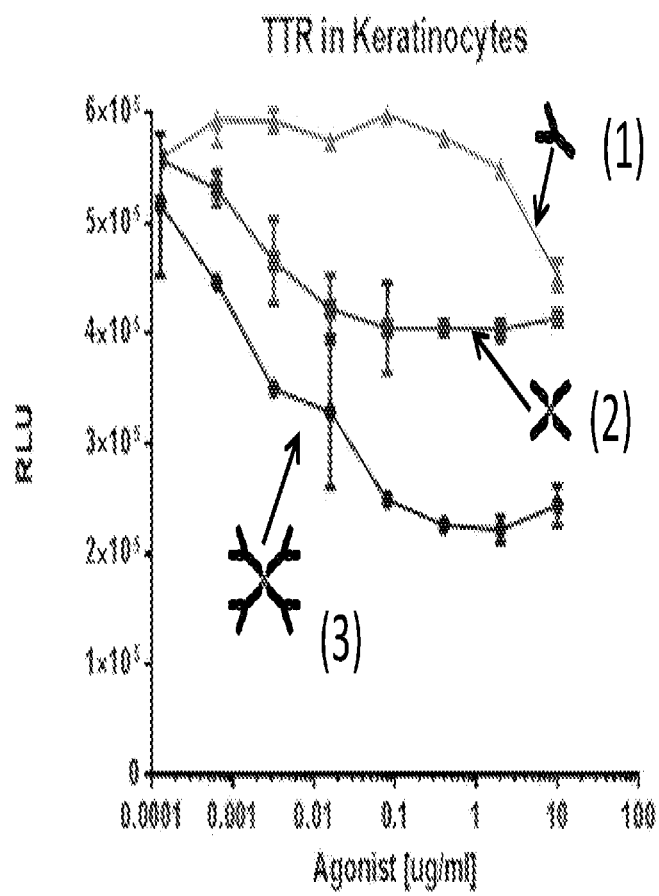
FIG. 17 shows the potency of the anti-TRAILR2 TTR Fab homotetramer ("2") and TTR antibody homotetramer ("3") compared to the parental mAb (conatumumab; ("1") in a primary human keratinocyte cell killing assay.

FIG. 17 illustrates the results of the keratinocyte assay. Again, conatumumab ("1") was ineffective in killing the primary human keratinocyte cells. The anti-TRAILR2 TTR Fab homotetramer ("2") demonstrates slightly better potency than conatumumab. Again, the anti-TRAILR2 TTR antibody homotetramer ("3") is substantially more potent than conatumumab at killing human primary keratinocyte cells. These results again demonstrate that TTR antibody homotetramer-mediated clustering can enhance activity in in vitro cell killing assays.

Murine Colo 205 Adenocarcinoma Model-Based Activity Assays

The activity of conatumumab, anti-TRAILR2 TTR antibody homodimer, anti-TRAILR2 TTR antibody homotetramer, and anti-TRAILR2 TTR Fab homotetramer fusion proteins was evaluated in an murine Colo205 human colon adenocarcinoma model. Colo205 human colon adenocarcinoma cells were maintained at 37° C. at 5% $CO_2$ in RPMI-1640 culture medium supplemented with 10% FBS (Sigma, 2442-500 mL), 4 mM L-glutamine (Hyclone, SH30034.01), 1 mM HEPES (Hyclone, SH30237.01), 1 mM Sodium Pyravate (Sigma, S8636-100 mL) and 2.5 g/L glucose (Sigma, G8769). At passage 3, cells were harvested and re-suspended in serum-free media to yield a final concentration of $10 \times 10^6$ cells/mL. Cell viability was determined by trypan-blue exclusion to be 98%.

Sixty female NU/NU Nude mice were injected with $1 \times 10^6$ cells (in 100 μL volume) subcutaneously in the right flank while mice were anesthetized with isofluorane. On day 7 post-tumor implantation, 50 mice with tumor volumes between 34 $mm^3$ and 99 $mm^3$ were distributed into 5 treatment groups with 10 mice each such that each group had similar mean tumor volumes ranging from 40 $mm^3$ to 48 $mm^3$. Ten mice with smaller or larger tumors were excluded from this study.

Five groups of animals received twice a week (b.i.w) intraperitoneal doses of conatumumab (0.69 M/animal), conatumumab-341-G1 (0.69 M/animal), anti-TRAILR2 TTR antibody homodimer (0.34 μM/animal), anti-TRAILR2 TTR antibody homotetramer (0.17 μM/animal), and anti-TRAILR2 TTR Fab homotetramer (0.17 μM/animal), for 3 weeks and total 6 treatments. Treatments were normalized so that all had the same number of binding sites as conatumumab, except the anti-TRAILR2 TTR Fab homotetramer (which only had half of the binding sites compared with the rest of the treatments). All treatments started on day 8 and ended on day 25 post tumor implantation (treatments were on day 8, 11, 15, 19, 22 and 25). All treatments were freshly prepared in diluent (DPBS) on the treatment date just prior to injection.

Tumor volume measurement: the length and width of tumors were measured with an ABS Digimatic solar caliper, model #Cd-S6"C (Mitutoyo Corporation, Japan). The tumor volume was calculated as $0.5 \times L \times W2$ where W was the smaller of the two measurements and expressed in $mm^3$.

Body weight measurement: for body weight measurements, animals were placed on into a weight dish on a scale (Mettler Toledo model PB602-S, Switzerland). Average body weights over a 3 second period were determined using the dynamic weight function of the scale. Body weights are reported as Body Weight Change which is calculated as $100 \times (We/Wi)$, where We is the current body weight and Wi is the body weight at treatment initiation. For this study day 4 body weights were used as Wi for all animals.

Euthanasia: five animals were euthanized prior to the end of the study because tumor size reached 1500-2000 $mm^3$. Conatumumab-341-G1 group: two mice were euthanized due to excessive tumor volume on Day 25; another two mice were euthanized due to excessive tumor volume on Day 35. Ten mice in anti-TRAILR2 TTR antibody homodimer group and the remaining six mice in conatumumab-341-G1 group were euthanized on Day 42 due to average tumor volume >1200 $mm^3$ or loss of more than half of the mice in the cohort. One mouse from the anti-TRAILR2 TTR Fab homotetramer group was euthanized due to tumor size >2000 $mm^3$ on Day 42. One mouse from the anti-TRAILR2 TTR Fab homotetramer group was euthanized due to excessive tumor volume on Day 49. All remaining animals were euthanized on day 63 as study termination. The animals were euthanized by an isofluorane overdose followed by blood collection by cardiac puncture.

Tumor measurements: data from between day 4 through day 63 were expressed as means plus or minus standard errors and plotted as a function of time. Statistical significance of observed differences between growth curves was evaluated by repeated measures analysis of variance of the transformed tumor volume data with Dunnett adjusted multiple comparisons. The analysis was done using SAS PROC MIXED procedure with model effects of transformed baseline tumor volume, day, treatment, and day-by-treatment interaction; a REPEATED statement where day was a repeated value, animal the subject and a Toeplitz covariance structure; and an LSMEANS statement to do a Dunnett analysis comparing the control group to the other treatment groups. The data was log or square root transformed according to Horwitz's method, and transformed baseline tumor volume was included as a covariate in the model to account for possible pre-treatment tumor volume differences. If the log or square root transformation failed to achieve a proper residual distribution, a nonparametric repeated measure analysis of variance model was used with the same model effects on rank of the tumor volume. P values of <0.05 were considered statistically significant. Conatumumab (wild type) and conatumumab-341-G1 groups were used as the control groups in the analysis.

Figure 18:
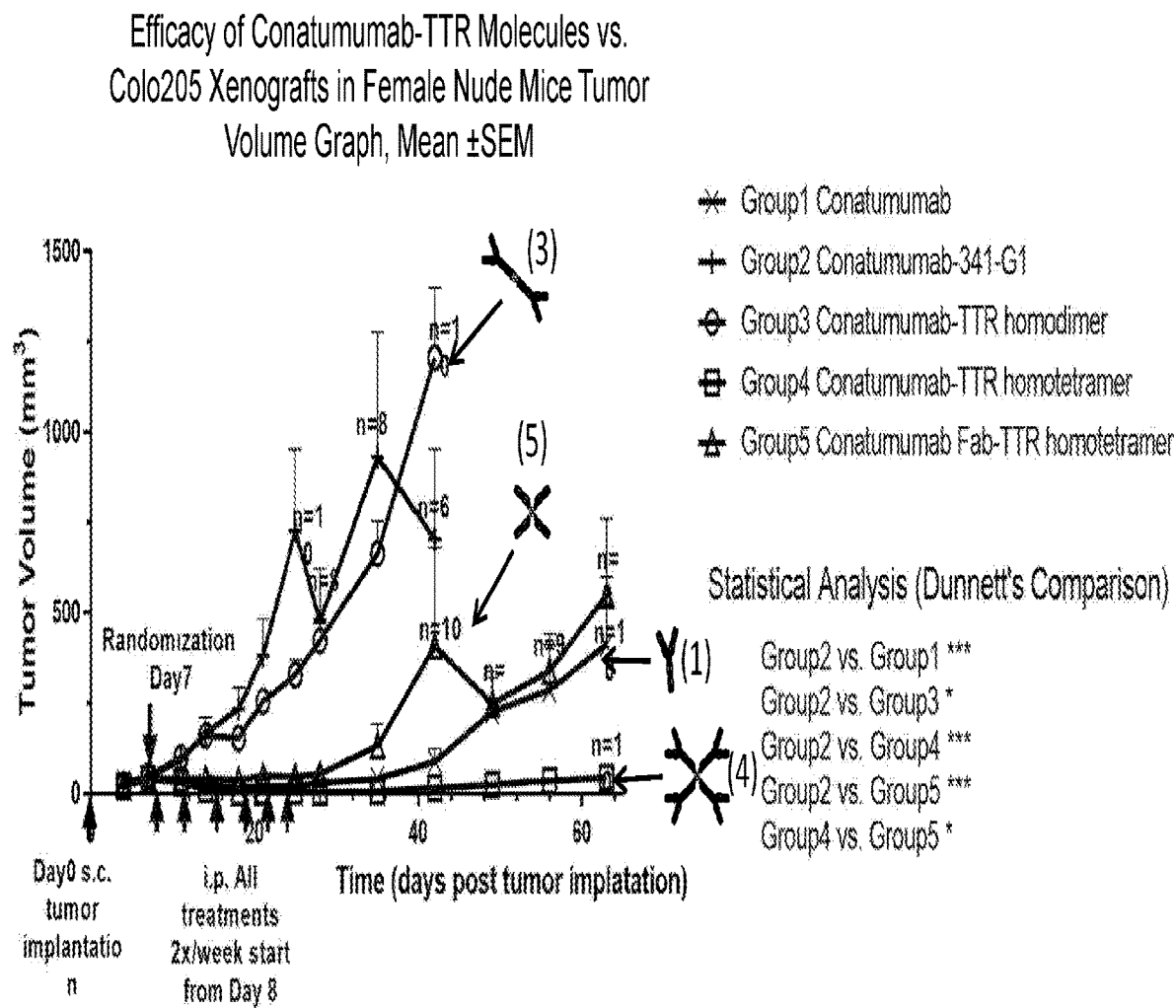
FIG. 18 shows the ability of anti-TRAILR2 TTR fusion proteins to suppress tumor growth compared to the parental mAb (conatumumab) in a murine colo205 model.

FIG. 18 illustrates the results of the murine colo205 model testing. Conatumumab ("Group 1"; 0.69 μM/animal), the anti-TRAILR2 TTR antibody homotetramer ("Group 4"; 0.17 μM/animal), and anti-TRAILR2 TTR Fab homotetramer ("Group 5"; 0.17 μM/animal) all suppress in vivo tumor growth during dosing, with the anti-TRAILR2 TTR antibody homotetramer demonstrating the best level of suppression during dosing. The anti-TRAILR2 TTR antibody homodimer ("Group 3"; 0.34 μM/animal) was only marginally better than the vehicle control (conatumumab-341-G1, "Group 2"; 0.69 μM/animal) at suppressing tumor growth. Notably, the anti-TRAILR2 TTR antibody homotetramer continued to suppress tumor growth long after dosing was halted. In addition, and surprisingly, although the anti-TRAILR2 TTR Fab homotetramer has a poor PK profile (FIG. 15), the construct is as effective as conatumumab in suppressing tumor growth. Without being bound by a particular theory, it is possible that the initial exposure to the anti-TRAILR2 TTR Fab homotetramer sets off a chain of events in the target cell that results in death and without requiring long term binding. In addition, the relatively small size of the Fab construct may provide it better access to the tumor environment, compensating for the poor PK. Finally, the physical configuration of the Fab construct may be more effective in vivo.

Murine SW403 Adenocarcinoma Model-Based Activity Assays

SW403 human colon adenocarcinoma cells were maintained at 37° C. in 5% $CO_2$ in RPMI-1640 culture medium (Sigma R0883) supplemented with 10% FBS (Sigma, 2442-500 mL), 4 mM L-glutamine (Hyclone, SH30034.01). At passage 5, cells were harvested and re-suspended in serum-free media to yield a final concentration of 50×10⁶ cells/mL. Cell viability was determined by trypan-blue exclusion to be 95%.

Seventy five female NU/NU Nude mice were injected with 5×10⁶ cells (in 100 µL volume) subcutaneously in the right flank while mice were anesthetized with isofluorane. On day 7 post-tumor implantation, 60 mice with tumor volumes between 21 mm³ and 160 mm³ were distributed into 6 treatment groups with 10 mice each such that each group had similar mean tumor volumes ranging from 58 mm³ to 66 mm³. Fifteen mice with smaller or larger tumors were excluded from this study.

Six groups of animals received twice a week (b.i.w) intraperitoneal doses of conatumumab Wild Type (1.38 µM/animal), conatumumab-341-G1 (1.38 µM/animal), anti-TRAILR2 TTR antibody homodimer (0.69 uM/animal), anti-TRAILR2 TTR antibody homotetramer (0.34 µM/animal), anti-TRAILR2 TTR Fab homotetramer (0.34 µM/animal), and DPBS (vehicle control), for 3 weeks and total 6 treatments. Treatments were normalized so that each had an equal number of binding sites as conatumumab Wild Type, except the anti-TRAILR2 TTR Fab homotetramer which only had half of the binding sites compared with rest treatments. All treatments started on day 15 and ended on day 32 post tumor implantation (treatments were on day 15, 19, 22, 26, 29 and 32). All treatments were freshly prepared in Diluent (DPBS) on the treatment date just prior to injection.

Tumor volume measurement: length and width of tumors were measured with an ABS digimatic solar caliper, model #Cd-S6"C (Mitutoyo Corporation, Japan). The tumor volume was calculated as $0.5 \times L \times W^2$ where W was the smaller of the two measurements and expressed in mm³.

Body weight measurement: animals were placed on into a weight dish on a scale (Mettler Toledo model PB602-S, Switzerland). Average body weights over a 3 second period were determined using the dynamic weight function of the scale. Body weights are reported as body weight change which is calculated as 100×(We/Wi), where We is the current body weight and Wi is the body weight at treatment initiation. For this study, day 4 body weights were used as Wi for all animals.

Euthanasia and tissue collection: eight animals were euthanized prior to the end of the study because tumor size reached 1500-2000 mm³. One mice from the conatumumab-341-G1 group was euthanized due to excessive tumor volume on Day 33. Another mouse from the conatumumab-341-G1 group, two from the DPBS vehicle control group, and one from the anti-TRAILR2 TTR antibody homodimer group were euthanized on Day 36. The remaining animals in the conatumumab-341-G1, DPBS vehicle control, and anti-TRAILR2 TTR antibody homodimer groups were all euthanized on day 39. One mouse from conatumumab WT group was euthanized on Day 39. Another mouse from the conatumumab WT group and one from the anti-TRAILR2 TTR Fab homotetramer group were euthanized on Day 46. All remaining animals in the conatumumab WT, anti-TRAILR2 TTR antibody homotetramer, and anti-TRAILR2 TTR Fab homotetramer groups were euthanized on Day 49 at study termination. All of the euthanasia were done by an isofluorane overdose followed by blood collection by cardiac puncture.

Tumor Measurements: data from between day 7 through day 49 were expressed as means plus or minus standard errors and plotted as a function of time. Statistical significance of observed differences between growth curves was evaluated by repeated measures analysis of variance of the transformed tumor volume data with Dunnett adjusted multiple comparisons. The analysis was done using SAS PROC MIXED procedure with model effects of transformed baseline tumor volume, day, treatment, and day-by-treatment interaction; a REPEATED statement where day was a repeated value, animal the subject and a Toeplitz covariance structure; and an LSMEANS statement to do a Dunnett analysis comparing the control group to the other treatment groups. The data was log or square root transformed according to Horwitz's method, and transformed baseline tumor volume was included as a covariate in the model to account for possible pre-treatment tumor volume differences. If the log or square root transformation failed to achieve a proper residual distribution, a nonparametric repeated measure analysis of variance model was used with the same model effects on rank of the tumor volume. P values of <0.05 were considered statistically significant. All statistical calculations were made through the use of AMG Biostatistical Analysis tool (cld-pweb-taivd.amgen.com/biostats/Statistics). The conatumumab WT group was used as the control group in the analysis.

Figure 19:
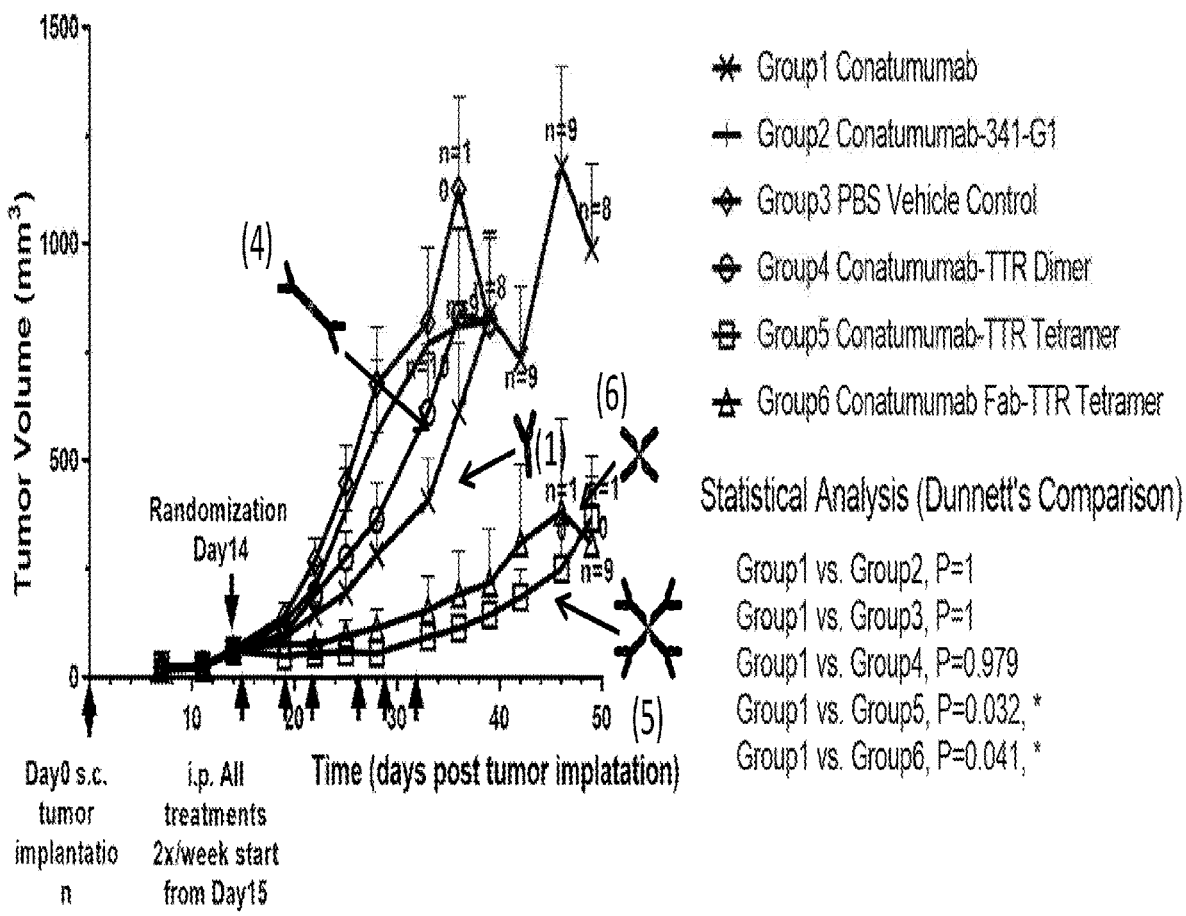
FIG. 19 shows the ability of anti-TRAILR2 TTR fusion proteins to suppress tumor growth compared to the parental mAb (conatumumab) in a murine SW403 model.

FIG. 19 illustrates the results of the murine SW403 model testing. The anti-TRAILR2 TTR antibody homotetramer ("Group 5") and anti-TRAILR2 TTR Fab homotetramer ("Group 6") suppress in vivo tumor growth better than conatumumab ("Group 1") during dosing. The anti-TRAILR2 TTR antibody homodimer ("Group 4") suppressed growth during dosing at about the same level as conatumumab, though neither is significantly better at growth suppression than the vehicle control ("Group 3"). Notably, both the anti-TRAILR2 TTR antibody homotetramer and anti-TRAILR2 TTR Fab homotetramer slow tumor growth even after dosing is halted. Again, it was surprising to observe that although the anti-TRAILR2 TTR Fab homotetramer has a poor PK profile (FIG. 15), the construct is as effective as the anti-TRAILR2 TTR antibody homotetramer in slowing tumor growth even after dosing is halted.

Figure 20:
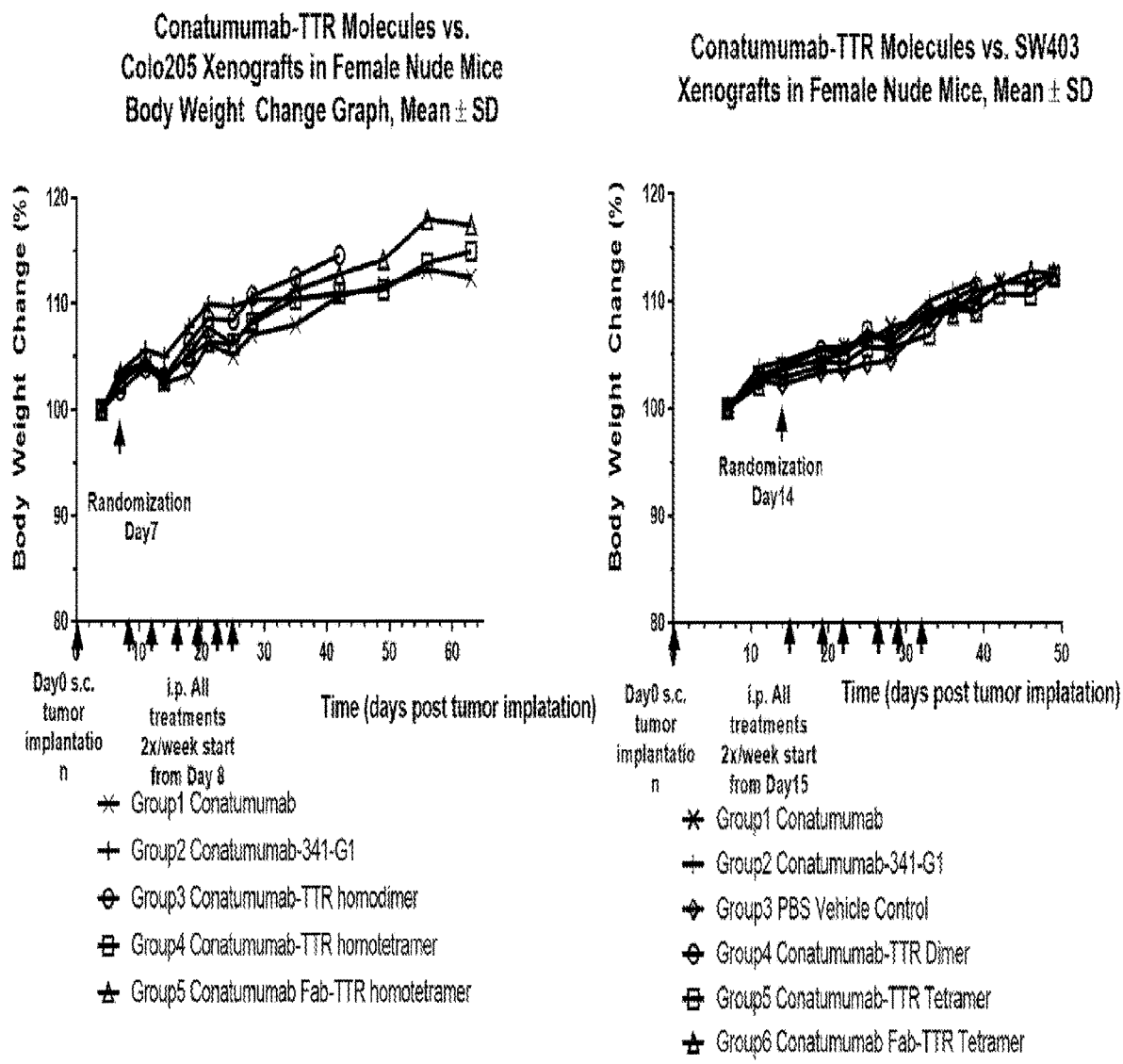
FIG. 20 shows the body weight of murine colo205 model mice and murine SW403 model mice is similar for all compounds tested.

FIG. 20 shows the body weight of murine colo25 model mice and murine SW403 model mice is similar for all compounds tested and appears to be on a normal upward trajectory. This result indicates that the tested compounds are not overtly toxic (since the mice were healthy enough to eat and gain weight normally).

SUMMARY OF SEQ ID NOS

| SEQ ID NO | Description |
| --- | --- |
| 1 | human transthyretin protein sequence w/C10A + K15A |
| 2 | human transthyretin nucleic acid sequence w/C10A + K15A |
| 3 | murine transthyretin protein sequence |
| 4 | murine transthyretin nucleic acid sequence |
| 5 | anti-CB1R antibody heavy chain protein sequence |
| 6 | anti-CB1R antibody heavy chain protein sequence w/EU E356K and EU D399K |

| SEQ ID NO | Description |
|---|---|
| 7 | anti-CB1R antibody heavy chain protein sequence w/EU K392D and EU K409D |
| 8 | anti-CB1R antibody heavy chain CDR1 protein sequence |
| 9 | anti-CB1R antibody heavy chain CDR2 protein sequence |
| 10 | anti-CB1R antibody heavy chain CDR3 protein sequence |
| 11 | anti-CB1R antibody light chain protein sequence |
| 12 | anti-CB1R antibody light chain CDR1 protein sequence |
| 13 | anti-CB1R antibody light chain CDR2 protein sequence |
| 14 | anti-CB1R antibody light chain CDR3 protein sequence |
| 15 | anti-CB1R antibody heavy chain nucleic acid sequence |
| 16 | anti-CB1R antibody heavy chain nucleic acid sequence w/E416K + D459K |
| 17 | anti-CB1R antibody heavy chain nucleic acid sequence w/K420D + K437D |
| 18 | 9H6 antibody heavy chain protein sequence w/N297G |
| 19 | anti-GITR antibody heavy chain protein sequence w/N297G, E356K, D399K |
| 20 | anti-GITR antibody heavy chain protein sequence w/N297G, K392D, K409D |
| 21 | anti-GITR Fab heavy chain protein sequence w/S183E |
| 22 | anti-GITR heavy chain CDR1 protein sequence |
| 23 | anti-GITR heavy chain CDR2 protein sequence |
| 24 | anti-GITR heavy chain CDR3 protein sequence |
| 25 | 9H6 light chain protein sequence |
| 26 | anti-GITR Fab light chain protein sequence w/S176K |
| 27 | anti-GITR light chain CDR1 protein sequence |
| 28 | anti-GITR light chain CDR2 protein sequence |
| 29 | anti-GITR light chain CDR3 protein sequence |
| 30 | GG linker + His tag |
| 31 | anti-TRAILR2 antibody IgG1 heavy chain protein sequence |
| 32 | anti-TRAILR2 antibody IgG1 heavy chain protein sequence w/N297G, KK |
| 33 | anti-TRAILR2 antibody IgG1 heavy chain protein sequence w/N297G, DD |
| 34 | anti-TRAILR2 Fab IgG2 heavy chain protein sequence w/S183E |
| 35 | anti-TRAILR2 heavy chain CDR1 protein sequence |
| 36 | anti-TRAILR2 heavy chain CDR2 protein sequence |
| 37 | anti-TRAILR2 heavy chain CDR3 protein sequence |
| 38 | anti-TRAILR2 antibody light chain protein sequence |
| 39 | anti-TRAILR2 Fab light chain protein sequence w/S176K |
| 40 | anti-GITR light chain CDR1 protein sequence |
| 41 | anti-GITR light chain CDR2 protein sequence |
| 42 | anti-GITR light chain CDR3 protein sequence |
| 43 | human transthyretin protein sequence w/out C10A + K15A |
| 44 | anti-CB1R Fab heavy chain protein sequence |
| 45 | anti-CB1R Fab heavy chain protein sequence w/S215E |
| 46 | anti-CB1R Fab light chain protein sequence w/S203K |
| 47 | GGGGS linker |

What is claimed:

1. A homodimer fusion protein comprising two antibodies linked to a transthyretin (TTR) protein complex,
   wherein the antibodies bind tumor necrosis factor-related apoptosis-inducing ligand receptor-2 (TRAILR2), and
   wherein the TTR protein complex comprises four TTR subunits.

2. The homodimer fusion protein of claim 1, wherein each subunit of said TTR protein complex comprises the amino acid sequence of SEQ ID NO: 43, and
   wherein the amino acid sequence of SEQ ID NO: 43 comprises the following mutations: C10A and K15A.

3. The homodimer fusion protein of claim 1, wherein the antibodies are conatumumab.

4. The homodimer fusion protein of claim 1, wherein said antibodies are directly fused without a linker to said TTR protein complex.

5. The homodimer fusion protein of claim 4, wherein each heavy chain C-terminus of each antibody is directly fused to the N-terminus of a TTR subunit.

6. The homodimer fusion protein of claim 1, wherein said antibodies are fused to said TTR protein complex via a linker.

7. The homodimer fusion protein of claim 6, wherein each heavy chain C-terminus of each antibody is fused via a linker to the N-terminus of a TTR subunit.

8. The homodimer fusion protein of claim 7, wherein said linker is an amino acid linker.

9. The homodimer fusion protein of claim 8, wherein said amino acid linker is 1-40 amino acids in length.

10. The homodimer fusion protein of claim 9, wherein said amino acid linker is GGGGS (SEQ ID NO: 47), (GGGGS)$_2$ (SEQ ID NO: 48), (GGGGS)$_3$ (SEQ ID NO: 49), (GGGGS)$_4$ (SEQ ID NO: 50), (GGGGS)$_5$ (SEQ ID NO: 51), or (GGGGS)$_6$ (SEQ ID NO: 52).

11. One or more isolated nucleic acid(s) encoding a homodimer fusion protein of claim 1.

12. An expression vector comprising a nucleic acid of claim 11.

13. A recombinant host cell comprising a nucleic acid of claim 11 or the vector of claim 12.

14. The recombinant host cell of claim 13, wherein said host cell is a Chinese hamster ovary (CHO) cell, E5 cell, baby hamster kidney (BHK) cell, monkey kidney cell, COS cell, human carcinoma cell, or human embryonic kidney 293 (HEK 293) cell.

15. A method of making a homodimer fusion protein of claim 1, said method comprising:
    a) culturing a recombinant host cell comprising:
       one or more isolated nucleic acid(s) encoding said homodimer fusion protein, or
       an expression vector comprising one or more isolated nucleic acid(s) encoding said homodimer fusion protein; and
    b) isolating the homodimer fusion protein from said culture.

16. A homotetramer fusion protein comprising four antigen binding proteins linked to a transthyretin (TTR) protein complex,
    wherein the four antigen binding proteins are antibodies or fragment antigen-binding regions (Fabs),
    wherein said antigen binding proteins bind tumor necrosis factor-related apoptosis-inducing ligand receptor-2 (TRAILR2), and
    wherein the TTR protein complex comprises four TTR subunits.

17. The homotetramer fusion protein of claim 16, wherein each subunit of said TTR protein complex comprises the amino acid sequence of SEQ ID NO: 43, and
    wherein the amino acid sequence of SEQ ID NO: 43 comprises the following mutations: C10A and K15A.

18. The homotetramer fusion protein of claim 16, wherein each antigen binding protein is an antibody.

19. The homotetramer fusion protein of claim 18, wherein each antibody is conatumumab.

20. The homotetramer fusion protein of claim 16, wherein each antigen binding protein is a Fab.

21. The homotetramer fusion protein of claim 20, wherein each Fab is derived from conatumumab.

22. The homotetramer fusion protein of claim 20, wherein said antigen binding proteins are directly fused without a linker to said TTR protein complex.

23. The homotetramer fusion protein of claim 20, wherein said antigen binding proteins are fused to said TTR protein complex via a linker.

24. The homotetramer fusion protein of claim 16, wherein said antigen binding proteins are directly fused without a linker to said TTR protein complex.

25. The homotetramer fusion protein of claim 24, wherein:
   when the antigen binding protein is an antibody, one heavy chain C-terminus of each antibody is directly fused to the N-terminus of a TTR subunit; and
   when the antigen binding protein is a Fab, one C-terminus of each Fab is directly fused to the N-terminus of a TTR subunit.

26. The homotetramer fusion protein of claim 16, wherein said antigen binding proteins are fused to said TTR protein complex via a linker.

27. The homotetramer fusion protein of claim 26, wherein:
   when the antigen binding protein is an antibody, one heavy chain C-terminus of each antibody is fused via a linker to the N-terminus of a TTR subunit; and
   when the antigen binding protein is a Fab, one C-terminus of each Fab is fused via a linker to the N-terminus of a TTR subunit.

28. The homotetramer fusion protein of claim 27, wherein said linker is an amino acid linker.

29. The homotetramer fusion protein of claim 28, wherein said amino acid linker is 1-40 amino acids in length.

30. The homotetramer fusion protein of claim 29, wherein said amino acid linker is GGGGS (SEQ ID NO: 47), (GGGGS)$_2$ (SEQ ID NO: 48), (GGGGS)$_3$ (SEQ ID NO: 49), (GGGGS)$_4$ (SEQ ID NO: 50), (GGGGS)$_5$ (SEQ ID NO: 51), or (GGGGS)$_6$ (SEQ ID NO: 52).

31. A method of making a homotetramer fusion protein of claim 16, said method comprising:
   a) culturing a recombinant host cell comprising:
      one or more isolated nucleic acid(s) encoding said homotetramer fusion protein, or
      an expression vector comprising one or more isolated nucleic acid(s) encoding said homotetramer fusion protein; and
   b) isolating the homotetramer fusion protein from said culture.

32. A pharmaceutical composition comprising:
   (i) a homodimer fusion protein comprising two antibodies linked to a transthyretin (TTR) protein complex,
      wherein the antibodies bind tumor necrosis factor-related apoptosis-inducing ligand receptor-2 (TRAILR2), and
      wherein the TTR protein complex comprises four TTR subunits; or
   (ii) a homotetramer fusion protein comprising four antigen binding proteins linked to a transthyretin (TTR) protein complex,
      wherein the four antigen binding proteins are antibodies or fragment antigen-binding regions (Fabs),
      wherein said antigen binding proteins bind tumor necrosis factor-related apoptosis-inducing ligand receptor-2 (TRAILR2), and
      wherein the TTR protein complex comprises four TTR subunits.

33. A method of treating cancer comprising administering to a patient in need thereof:
   (i) a homodimer fusion protein comprising two antibodies linked to a transthyretin (TTR) protein complex,
      wherein the antibodies bind tumor necrosis factor-related apoptosis-inducing ligand receptor-2 (TRAILR2), and
      wherein the TTR protein complex comprises four TTR subunits; or
   (ii) a homotetramer fusion protein comprising four antigen binding proteins linked to a transthyretin (TTR) protein complex,
      wherein the four antigen binding proteins are antibodies or fragment antigen-binding regions (Fabs),
      wherein said antigen binding proteins bind tumor necrosis factor-related apoptosis-inducing ligand receptor-2 (TRAILR2), and
      wherein the TTR protein complex comprises four TTR subunits.

* * * * *

SEQUENCE LISTING

<160> NUMBER OF SEQ ID NOS: 124

<210> SEQ ID NO 1
<211> LENGTH: 127
<212> TYPE: PRT
<213> ORGANISM: Homo sapiens

<400> SEQUENCE: 1

```
Gly Pro Thr Gly Thr Gly Glu Ser Lys Ala Pro Leu Met Val Ala Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110
```

Pro Tyr Ser Tyr Ser Thr Thr Ala Val Val Thr Asn Pro Lys Glu
        115                 120                 125

<210> SEQ ID NO 2
<211> LENGTH: 381
<212> TYPE: DNA
<213> ORGANISM: Homo sapiens

<400> SEQUENCE: 2
ggccctacgg gcaccggtga atccaaggct cctctgatgg tcgccgttct agatgctgtc      60
cgaggcagtc ctgccatcaa tgtggccgtg catgtgttca gaaaggctgc tgatgacacc     120
tgggagccat ttgcctctgg gaaaaccagt gagtctggag agctgcatgg gctcacaact     180
gaggaggaat ttgtagaagg gatatacaaa gtggaaatag acaccaaatc ttactgaaag     240
gcacttggca tctccccatt ccatgagcat gcagaggtgg tattcacagc caacgactcc     300
ggcccccgcc gctacaccat tgccgccctg ctgagcccct actcctattc caccacggct     360
gtcgtcacca atcccaagga a                                              381

<210> SEQ ID NO 3
<211> LENGTH: 127
<212> TYPE: PRT
<213> ORGANISM: Mus musculus

<400> SEQUENCE: 3

Gly Pro Ala Gly Ala Gly Glu Ser Lys Cys Pro Leu Met Val Lys Val
1               5                   10                  15

Leu Asp Ala Val Arg Gly Ser Pro Ala Val Asp Val Ala Lys Val
            20                  25                  30

Phe Lys Lys Thr Ser Glu Gly Ser Trp Glu Pro Phe Ala Ser Gly Lys
        35                  40                  45

Thr Ala Glu Ser Gly Glu Leu His Gly Leu Thr Thr Asp Glu Lys Phe
    50                  55                  60

Val Glu Gly Val Tyr Arg Val Glu Leu Asp Thr Lys Ser Tyr Trp Lys
65                  70                  75                  80

Thr Leu Gly Ile Ser Pro Phe His Glu Phe Ala Asp Val Phe Thr
                85                  90                  95

Ala Asn Asp Ser Gly His Arg His Tyr Thr Ile Ala Ala Leu Leu Ser
            100                 105                 110

Pro Tyr Ser Tyr Ser Thr Thr Ala Val Val Ser Asn Pro Gln Asn
        115                 120                 125

<210> SEQ ID NO 4
<211> LENGTH: 615
<212> TYPE: DNA
<213> ORGANISM: Mus musculus

<400> SEQUENCE: 4
acagaagtcc actcattctt ggcaggatgg cttctcatcg tctgctcctc ctctgccttg      60
ctggactggt atttgtgtct gaggctggcc tacgggcac cggtgaatcc aagtgtcctc     120
tgatggtcaa agttctagat gctgtccgag gcagtcctgc catcaatgtg gccgtgcatg     180
tgttcagaaa ggctgctgat gacacctggg agccatttgc ctctgggaaa accagtgagt     240
ctggagagct gcatgggctc acaactgagg aggaatttgt agaagggata tacaaagtgg     300
aaatagacac caaatcttac tggaaggcac ttggcatctc cccattccat gagcatgcag     360
aggtggtatt cacagccaac gactccggcc ccgccgcta ccattgcc gccctgctga       420

```
gcccctactc ctattccacc acggctgtcg tcaccaatcc caaggaatga gggacttctc    480
ctccagtgga cctgaaggac gagggatggg atttcatgta accaagagta ttccattttt    540
actaaagcac tgttttcacc tcatatgcta tgttagaagt ccaggcagag acaataaaac    600
attcctgtga aaggc                                                     615
```

<210> SEQ ID NO 5
<211> LENGTH: 452
<212> TYPE: PRT
<213> ORGANISM: Homo sapiens

<400> SEQUENCE: 5

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gln |
| 1 | | | | 5 | | | | | 10 | | | | | 15 | |
| Thr | Leu | Ser | Leu | Thr | Cys | Thr | Val | Ser | Gly | Gly | Ser | Ile | Arg | Arg | Gly |
| | | | 20 | | | | | 25 | | | | | 30 | | |
| Gly | Asp | Tyr | Trp | Ser | Trp | Ile | Arg | Gln | His | Pro | Gly | Lys | Gly | Leu | Glu |
| | | 35 | | | | | 40 | | | | | 45 | | | |
| Trp | Ile | Gly | Tyr | Ile | Tyr | Tyr | Ser | Gly | Ser | Thr | Asn | Tyr | Asn | Pro | Ser |
| 50 | | | | | 55 | | | | | 60 | | | | | |
| Leu | Lys | Ser | Arg | Ala | Thr | Ile | Ser | Val | Asp | Thr | Ser | Lys | Asn | Gln | Phe |
| 65 | | | | | 70 | | | | | 75 | | | | | 80 |
| Ser | Leu | Lys | Leu | Ser | Ser | Val | Thr | Ala | Ala | Asp | Thr | Ala | Val | Tyr | Tyr |
| | | | | 85 | | | | | 90 | | | | | 95 | |
| Cys | Ala | Arg | Asp | Tyr | Asp | Ile | Leu | Thr | Gly | Tyr | Ser | Tyr | Tyr | Tyr | Tyr |
| | | | 100 | | | | | 105 | | | | | 110 | | |
| Gly | Met | Asp | Val | Trp | Gly | Gln | Gly | Thr | Thr | Val | Thr | Val | Ser | Ser | Ala |
| | | 115 | | | | | 120 | | | | | 125 | | | |
| Ser | Thr | Lys | Gly | Pro | Ser | Val | Phe | Pro | Leu | Ala | Pro | Cys | Ser | Arg | Ser |
| 130 | | | | | 135 | | | | | 140 | | | | | |
| Thr | Ser | Glu | Ser | Thr | Ala | Ala | Leu | Gly | Cys | Leu | Val | Lys | Asp | Tyr | Phe |
| 145 | | | | | 150 | | | | | 155 | | | | | 160 |
| Pro | Glu | Pro | Val | Thr | Val | Ser | Trp | Asn | Ser | Gly | Ala | Leu | Thr | Ser | Gly |
| | | | | 165 | | | | | 170 | | | | | 175 | |
| Val | His | Thr | Phe | Pro | Ala | Val | Leu | Gln | Ser | Ser | Gly | Leu | Tyr | Ser | Leu |
| | | | | 180 | | | | | 185 | | | | | 190 | |
| Ser | Ser | Val | Val | Thr | Val | Pro | Ser | Ser | Asn | Phe | Gly | Thr | Gln | Thr | Tyr |
| | | | 195 | | | | | 200 | | | | | 205 | | |
| Thr | Cys | Asn | Val | Asp | His | Lys | Pro | Ser | Asn | Thr | Lys | Val | Asp | Lys | Thr |
| | 210 | | | | | 215 | | | | | 220 | | | | |
| Val | Glu | Arg | Lys | Cys | Cys | Val | Glu | Cys | Pro | Pro | Cys | Pro | Ala | Pro | Pro |
| 225 | | | | | 230 | | | | | 235 | | | | | 240 |
| Val | Ala | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Gln | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Phe | Asn | Ser |
| | 290 | | | | | 295 | | | | | 300 | | | | |
| Thr | Phe | Arg | Val | Val | Ser | Val | Leu | Thr | Val | Val | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Gly | Leu | Pro | Ala |
| | | | | 325 | | | | | 330 | | | | | 335 | |

```
Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
            450

<210> SEQ ID NO 6
<211> LENGTH: 452
<212> TYPE: PRT
<213> ORGANISM: Homo sapiens

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Tyr Asp Ile Leu Thr Gly Tyr Ser Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
            130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
            195                 200                 205

Thr Cys Asn Val Asp His Lys Pro Ser Asn Thr Lys Val Asp Lys Thr
            210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
```

```
            245                 250                 255
Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Lys Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Met Leu Lys Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
            450

<210> SEQ ID NO 7
<211> LENGTH: 452
<212> TYPE: PRT
<213> ORGANISM: Homo sapiens

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
            20                  25                  30

Gly Asp Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160
```

```
Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
            195                 200                 205

Thr Cys Asn Val Asp His Lys Pro Ser Asn Thr Lys Val Asp Lys Thr
            210                 215                 220

Val Glu Arg Lys Cys Cys Val Glu Cys Pro Cys Pro Ala Pro Pro
225                 230                 235                 240

Val Ala Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
            325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Asp Thr Thr
385                 390                 395                 400

Pro Pro Met Leu Asp Ser Asp Gly Ser Phe Phe Leu Tyr Ser Asp Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450

<210> SEQ ID NO 8
<211> LENGTH: 7
<212> TYPE: PRT
<213> ORGANISM: Homo sapiens

<400> SEQUENCE: 8

Arg Gly Gly Asp Tyr Trp Ser
1               5

<210> SEQ ID NO 9
<211> LENGTH: 16
<212> TYPE: PRT
<213> ORGANISM: Homo sapiens

<400> SEQUENCE: 9

Tyr Ile Tyr Tyr Ser Gly Ser Thr Asn Tyr Asn Pro Ser Leu Lys Ser
1               5                   10                  15
```

<210> SEQ ID NO 10
<211> LENGTH: 17
<212> TYPE: PRT
<213> ORGANISM: Homo sapiens

<400> SEQUENCE: 10

Asp Tyr Asp Ile Leu Thr Gly Tyr Ser Tyr Tyr Tyr Gly Met Asp
1               5                   10                  15

Val

<210> SEQ ID NO 11
<211> LENGTH: 219
<212> TYPE: PRT
<213> ORGANISM: Homo sapiens

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 12
<211> LENGTH: 16
<212> TYPE: PRT
<213> ORGANISM: Homo sapiens

<400> SEQUENCE: 12

Arg Ser Ser Gln Ser Leu Leu His Ser Asn Gly Tyr Asn Tyr Leu Asp
1               5                   10                  15

<210> SEQ ID NO 13
<211> LENGTH: 7
<212> TYPE: PRT
<213> ORGANISM: Homo sapiens

<400> SEQUENCE: 13

Leu Gly Ser Asn Arg Ala Ser
1               5

<210> SEQ ID NO 14
<211> LENGTH: 9
<212> TYPE: PRT
<213> ORGANISM: Homo sapiens

<400> SEQUENCE: 14

Met Gln Ala Leu Gln Thr Pro Arg Thr
1               5

<210> SEQ ID NO 15
<211> LENGTH: 1956
<212> TYPE: DNA
<213> ORGANISM: Homo sapiens

<400> SEQUENCE: 15

```
caggtgcagc tgcaggagtc gggcccagga ctggtgaagc cttcacagac cctgtccctc      60
acctgcactg tctctggtgg ctccatcaga gaggtggtg actattggag ctggattcgc     120
cagcacccag ggaagggcct ggagtggatt gggtacatct attacagtgg gagtactaac     180
tacaacccgt ccctcaagag tcgagctacc atatcagtag acacgtctaa gaaccagttc     240
tccctgaagc tgagctctgt gactgccgcg gacacggccg tctattactg tgcgagagat     300
tacgatattt tgactggtta ttcctactac tactacggta tggacgtctg gggccaaggg     360
accacggtca ccgtctctag tgcctccacc aagggcccat cggtcttccc cctggcgccc     420
tgctccagga gcacctccga gagcacagcg gccctgggct gcctggtcaa ggactacttc     480
cccgaaccgg tgacggtgtc gtggaactca ggcgctctga ccagcggcgt gcacaccttc     540
ccagctgtcc tacagtcctc aggactctac tccctcagca gcgtggtgac cgtgccctcc     600
agcaacttcg gcacccagac ctacacctgc aacgtagatc acaagcccag caacaccaag     660
acctgcactg tctctggtgg ctccatcaga gaggtggtg actattggag ctggattcgc     720
cagcacccag ggaagggcct ggagtggatt gggtacatct attacagtgg gagtactaac     780
tacaacccgt ccctcaagag tcgagctacc atatcagtag acacgtctaa gaaccagttc     840
tccctgaagc tgagctctgt gactgccgcg gacacggccg tctattactg tgcgagagat     900
tacgatattt tgactggtta ttcctactac tactacggta tggacgtctg gggccaaggg     960
accacggtca ccgtctctag tgcctccacc aagggcccat cggtcttccc cctggcgccc    1020
tgctccagga gcacctccga gagcacagcg gccctgggct gcctggtcaa ggactacttc    1080
cccgaaccgg tgacggtgtc gtggaactca ggcgctctga ccagcggcgt gcacaccttc    1140
ccagctgtcc tacagtcctc aggactctac tccctcagca gcgtggtgac cgtgccctcc    1200
agcaacttcg gcacccagac ctacacctgc aacgtagatc acaagcccag caacaccaag    1260
gtggacaaga cagttgagcg caaatgttgt gtcgagtgcc caccgtgccc agcaccacct    1320
gtggcaggac cgtcagtctt cctcttcccc ccaaaaccca aggacaccct catgatctcc    1380
cggacccctg aggtcacgtg cgtggtggtg gacgtgagcc acgaagaccc cgaggtccag    1440
ttcaactggt acgtggacgg cgtggaggtg cataatgcca agacaaagcc acgggaggag    1500
cagttcaaca gcacgttccg tgtggtcagc gtcctcaccg ttgtgcacca ggactggctg    1560
aacggcaagg agtacaagtg caaggtctcc aacaaaggcc tcccagcccc catcgagaaa    1620
```

-continued

| | |
|---|---|
| accatctcca aaaccaaagg gcagccccga gaaccacagg tgtacaccct gcccccatcc | 1680 |
| cgggaggaga tgaccaagaa ccaggtcagc ctgacctgcc tggtcaaagg cttctacccc | 1740 |
| agcgacatcg ccgtggagtg ggagagcaat gggcagccgg agaacaacta caagaccaca | 1800 |
| cctcccatgc tggactccga cggctccttc ttcctctaca gcaagctcac cgtggacaag | 1860 |
| agcaggtggc agcaggggaa cgtcttctca tgctccgtga tgcatgaggc tctgcacaac | 1920 |
| cactacacgc agaagagcct ctccctgtct ccgggt | 1956 |

<210> SEQ ID NO 16
<211> LENGTH: 1356
<212> TYPE: DNA
<213> ORGANISM: Homo sapiens

<400> SEQUENCE: 16

| | |
|---|---|
| caggtgcagc tgcaggagtc gggcccagga ctggtgaagc cttcacagac cctgtccctc | 60 |
| acctgcactg tctctggtgg ctccatcaga agaggtggtg actattggag ctggattcgc | 120 |
| cagcacccag ggaagggcct ggagtggatt gggtacatct attacagtgg gagtactaac | 180 |
| tacaacccgt ccctcaagag tcgagctacc atatcagtag acacgtctaa gaaccagttc | 240 |
| tccctgaagc tgagctctgt gactgccgcg gacacggccg tctattactg tgcgagagat | 300 |
| tacgatattt tgactggtta ttcctactac tactacggta tggacgtctg gggccaaggg | 360 |
| accacggtca ccgtctctag tgcctccacc aagggcccat cggtcttccc cctggcgccc | 420 |
| tgctccagga gcacctccga gagcacagcg gccctgggct gcctggtcaa ggactacttc | 480 |
| cccgaaccgg tgacggtgtc gtggaactca ggcgctctga ccagcggcgt gcacaccttc | 540 |
| ccagctgtcc tacagtcctc aggactctac tccctcagca gcgtggtgac cgtgccctcc | 600 |
| agcaacttcg gcacccagac ctacacctgc aacgtagatc acaagcccag caacaccaag | 660 |
| gtggacaaga cagttgagcg caaatgttgt gtcgagtgcc caccgtgccc agcaccacct | 720 |
| gtggcaggac cgtcagtctt cctcttcccc ccaaaaccca aggacaccct catgatctcc | 780 |
| cggacccctg aggtcacgtg cgtggtggtg gacgtgagcc acgaagaccc cgaggtccag | 840 |
| ttcaactggt acgtggacgg cgtggaggtg cataatgcca agacaaagcc acgggaggag | 900 |
| cagttcaaca gcacgttccg tgtggtcagc gtcctcaccg ttgtgcacca ggactggctg | 960 |
| aacggcaagg agtacaagtg caaggtctcc aacaaaggcc tcccagcccc catcgagaaa | 1020 |
| accatctcca aaaccaaagg gcagccccga gaaccacagg tgtacaccct gcccccatcc | 1080 |
| cggaaggaga tgaccaagaa ccaggtcagc ctgacctgcc tggtcaaagg cttctacccc | 1140 |
| agcgacatcg ccgtggagtg ggagagcaat gggcagccgg agaacaacta caagaccaca | 1200 |
| cctcccatgc tgaagtccga cggctccttc ttcctctaca gcaagctcac cgtggacaag | 1260 |
| agcaggtggc agcaggggaa cgtcttctca tgctccgtga tgcatgaggc tctgcacaac | 1320 |
| cactacacgc agaagagcct ctccctgtct ccgggt | 1356 |

<210> SEQ ID NO 17
<211> LENGTH: 1356
<212> TYPE: DNA
<213> ORGANISM: Homo sapiens

<400> SEQUENCE: 17

| | |
|---|---|
| caggtgcagc tgcaggagtc gggcccagga ctggtgaagc cttcacagac cctgtccctc | 60 |
| acctgcactg tctctggtgg ctccatcaga agaggtggtg actattggag ctggattcgc | 120 |
| cagcacccag ggaagggcct ggagtggatt gggtacatct attacagtgg gagtactaac | 180 |

```
tacaacccgt ccctcaagag tcgagctacc atatcagtag acacgtctaa gaaccagttc      240
tccctgaagc tgagctctgt gactgccgcg gacacggccg tctattactg tgcgagagat      300
tacgatattt tgactggtta ttcctactac tactacggta tggacgtctg gggccaaggg      360
accacggtca ccgtctctag tgcctccacc aagggcccat cggtcttccc cctggcgccc      420
tgctccagga gcacctccga gagcacagcg ccctgggct gcctggtcaa ggactacttc       480
cccgaaccgg tgacggtgtc gtggaactca ggcgctctga ccagcggcgt gcacaccttc      540
ccagctgtcc tacagtcctc aggactctac tccctcagca gcgtggtgac cgtgccctcc      600
agcaacttcg gcacccagac ctacacctgc aacgtagatc acaagcccag caacaccaag      660
gtggacaaga cagttgagcg caaatgttgt gtcgagtgcc caccgtgccc agcaccacct      720
gtggcaggac cgtcagtctt cctcttcccc ccaaaaccca aggacaccct catgatctcc      780
cggacccctg aggtcacgtg cgtggtggtg gacgtgagcc acgaagaccc gaggtccag       840 ttcaactggt acgtggacgg cgtggaggtg cataatgcca agacaaagcc acgggaggag      900
cagttcaaca gcacgttccg tgtggtcagc gtcctcaccg ttgtgcacca ggactggctg      960
aacggcaagg agtacaagtg caaggtctcc aacaaaggcc tcccagcccc catcgagaaa     1020
accatctcca aaaccaaagg gcagccccga gaaccacagg tgtacaccct gcccccatcc     1080
cgggaggaga tgaccaagaa ccaggtcagc ctgacctgcc tggtcaaagg cttctacccc     1140
agcgacatcg ccgtggagtg ggagagcaat gggcagccgg agaacaacta cgataccaca     1200
cctcccatgc tggactccga cggctccttc ttcctctaca gcgatctcac cgtggacaag     1260
agcaggtggc agcaggggaa cgtcttctca tgctccgtga tgcatgaggc tctgcacaac     1320
cactacacgc agaagagcct ctccctgtct ccgggt                               1356
```

<210> SEQ ID NO 18
<211> LENGTH: 452
<212> TYPE: PRT
<213> ORGANISM: Homo sapiens

<400> SEQUENCE: 18

```
Gln Val Gln Leu Val Glu Ser Gly Gly Gly Val Val Gln Pro Gly Arg
1               5                  10                  15

Ser Leu Arg Leu Ser Cys Val Ala Ser Gly Phe Thr Phe Ser Ser Tyr
            20                  25                  30

Gly Met His Trp Ile Arg Gln Ala Pro Gly Lys Gly Leu Glu Trp Val
        35                  40                  45

Ala Val Ile Trp Tyr Glu Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Arg Leu Gly Lys Asp Tyr Tyr Ser Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Gly Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly
    450

<210> SEQ ID NO 19
<211> LENGTH: 452
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Phe Ser Ser Tyr
            20                  25                  30
Gly Met His Trp Ile Arg Gln Ala Pro Gly Lys Gly Leu Glu Trp Val
        35                  40                  45
Ala Val Ile Trp Tyr Glu Gly Ser Asn Lys Tyr Tyr Ala Glu Ser Val
    50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Arg Leu Gly Lys Asp Tyr Tyr Ser Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Gly Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Lys Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Lys Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 20
<211> LENGTH: 452
<212> TYPE: PRT
<213> ORGANISM: Homo sapiens
```

-continued

```
<400> SEQUENCE: 20

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Ile Arg Gln Ala Pro Gly Lys Gly Leu Glu Trp Val
        35                  40                  45

Ala Val Ile Trp Tyr Glu Gly Ser Asn Lys Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Gly Lys Asp Tyr Tyr Ser Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Gly Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Asp Thr Thr
385                 390                 395                 400

Pro Pro Val Leu Asp Ser Asp Gly Ser Phe Phe Leu Tyr Ser Asp Leu
                405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450

<210> SEQ ID NO 21
<211> LENGTH: 228
<212> TYPE: PRT
<213> ORGANISM: Homo sapiens

<400> SEQUENCE: 21

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Ile Arg Gln Ala Pro Gly Lys Gly Leu Glu Trp Val
            35                  40                  45

Ala Val Ile Trp Tyr Glu Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Gly Lys Asp Tyr Tyr Ser Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Glu Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Gly Gly
225

<210> SEQ ID NO 22
<211> LENGTH: 5
<212> TYPE: PRT
<213> ORGANISM: Homo sapiens

<400> SEQUENCE: 22

Ser Tyr Gly Met His
1               5

<210> SEQ ID NO 23
<211> LENGTH: 17
<212> TYPE: PRT
<213> ORGANISM: Homo sapiens
```

```
<400> SEQUENCE: 23

Val Ile Trp Tyr Glu Gly Ser Asn Lys Tyr Tyr Ala Glu Ser Val Lys
1               5                   10                  15

Gly

<210> SEQ ID NO 24
<211> LENGTH: 14
<212> TYPE: PRT
<213> ORGANISM: Homo sapiens

<400> SEQUENCE: 24

Gly Gly Arg Leu Gly Lys Asp Tyr Tyr Ser Gly Met Asp Val
1               5                   10

<210> SEQ ID NO 25
<211> LENGTH: 214
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 214
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Thr Tyr Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Lys
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 11
<212> TYPE: PRT
<213> ORGANISM: Homo sapiens

<400> SEQUENCE: 27

Arg Ala Ser Gln Gly Ile Arg Asn Asp Leu Gly
1               5                   10

<210> SEQ ID NO 28
<211> LENGTH: 7
<212> TYPE: PRT
<213> ORGANISM: Homo sapiens

<400> SEQUENCE: 28

Ala Thr Ser Ser Leu Gln Ser
1               5

<210> SEQ ID NO 29
<211> LENGTH: 9
<212> TYPE: PRT
<213> ORGANISM: Homo sapiens

<400> SEQUENCE: 29

Leu Gln His Asn Thr Tyr Pro Trp Thr
1               5

<210> SEQ ID NO 30
<211> LENGTH: 8
<212> TYPE: PRT
<213> ORGANISM: Artificial Sequence
<220> FEATURE:

```
<223> OTHER INFORMATION: Synthetic polypeptide

<400> SEQUENCE: 30

Gly Gly His His His His His His
1               5

<210> SEQ ID NO 31
<211> LENGTH: 451
<212> TYPE: PRT
<213> ORGANISM: Homo sapiens

<400> SEQUENCE: 31

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
```

```
               340             345             350
Val Tyr Thr Leu Pro Pro Ser Arg Glu Glu Met Thr Lys Asn Gln Val
            355             360             365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
                405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
        435             440             445

Ser Pro Gly
    450

<210> SEQ ID NO 32
<211> LENGTH: 451
<212> TYPE: PRT
<213> ORGANISM: Homo sapiens

<400> SEQUENCE: 32

Gln Val Gln Leu Gln Glu Ser Gly Pro Gly Leu Val Lys Pro Ser Gln
1               5               10              15

Thr Leu Ser Leu Thr Cys Thr Val Ser Gly Gly Ser Ile Ser Ser Gly
            20              25              30

Asp Tyr Phe Trp Ser Trp Ile Arg Gln Leu Pro Gly Lys Gly Leu Glu
        35              40              45

Trp Ile Gly His Ile His Asn Ser Gly Thr Thr Tyr Tyr Asn Pro Ser
    50              55              60

Leu Lys Ser Arg Val Thr Ile Ser Val Asp Thr Ser Lys Lys Gln Phe
65              70              75              80

Ser Leu Arg Leu Ser Ser Val Thr Ala Ala Asp Thr Ala Val Tyr Tyr
            85              90              95

Cys Ala Arg Asp Arg Gly Gly Asp Tyr Tyr Gly Met Asp Val Trp
        100             105             110

Gly Gln Gly Thr Thr Val Thr Val Ser Ser Ala Ser Thr Lys Gly Pro
    115             120             125

Ser Val Phe Pro Leu Ala Pro Ser Ser Lys Ser Thr Ser Gly Gly Thr
130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ser Ser Gly Leu Tyr Ser Leu Ser Ser Val Val Thr
        180             185             190

Val Pro Ser Ser Ser Leu Gly Thr Gln Thr Tyr Ile Cys Asn Val Asn
    195             200             205

His Lys Pro Ser Asn Thr Lys Val Asp Lys Lys Val Glu Pro Lys Ser
210             215             220

Cys Asp Lys Thr His Thr Cys Pro Pro Cys Pro Ala Pro Glu Leu Leu
225             230             235             240

Gly Gly Pro Ser Val Phe Leu Phe Pro Pro Lys Pro Lys Asp Thr Leu
            245             250             255
```

Met Ile Ser Arg Thr Pro Glu Val Thr Cys Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Gly Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Lys Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Lys Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 33
<211> LENGTH: 451
<212> TYPE: PRT
<213> ORGANISM: Homo sapiens

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
        35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Val Val Thr
            180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Gly Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Asp Thr Thr Pro
385                 390                 395                 400

Pro Val Leu Asp Ser Asp Gly Ser Phe Phe Leu Tyr Ser Asp Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
     450

<210> SEQ ID NO 34
<211> LENGTH: 227
<212> TYPE: PRT
<213> ORGANISM: Homo sapiens

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
        50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr

```
                    85                  90                  95
Cys Ala Arg Asp Arg Gly Gly Asp Tyr Tyr Tyr Gly Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Gly Gly
225
```

<210> SEQ ID NO 35
<211> LENGTH: 7
<212> TYPE: PRT
<213> ORGANISM: Homo sapiens

<400> SEQUENCE: 35

```
Ser Gly Asp Tyr Phe Trp Ser
1               5
```

<210> SEQ ID NO 36
<211> LENGTH: 16
<212> TYPE: PRT
<213> ORGANISM: Homo sapiens

<400> SEQUENCE: 36

```
His Ile His Asn Ser Gly Thr Thr Tyr Tyr Asn Pro Ser Leu Lys Ser
1               5                   10                  15
```

<210> SEQ ID NO 37
<211> LENGTH: 12
<212> TYPE: PRT
<213> ORGANISM: Homo sapiens

<400> SEQUENCE: 37

```
Asp Arg Gly Gly Asp Tyr Tyr Tyr Gly Met Asp Val
1               5                   10
```

<210> SEQ ID NO 38
<211> LENGTH: 215
<212> TYPE: PRT
<213> ORGANISM: Homo sapiens

<400> SEQUENCE: 38

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45
```

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
210                 215

<210> SEQ ID NO 39
<211> LENGTH: 215
<212> TYPE: PRT
<213> ORGANISM: Homo sapiens

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
                20                  25                  30

Tyr Leu Ala Trp Tyr Gln Gln Lys Pro Gly Gln Ala Pro Ser Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Lys Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

```
Ser Phe Asn Arg Gly Glu Cys
    210                 215

<210> SEQ ID NO 40
<211> LENGTH: 12
<212> TYPE: PRT
<213> ORGANISM: Homo sapiens

<400> SEQUENCE: 40

Arg Ala Ser Gln Gly Ile Ser Arg Ser Tyr Leu Ala
1               5                   10

<210> SEQ ID NO 41
<211> LENGTH: 7
<212> TYPE: PRT
<213> ORGANISM: Homo sapiens

<400> SEQUENCE: 41

Gly Ala Ser Ser Arg Ala Thr
1               5

<210> SEQ ID NO 42
<211> LENGTH: 9
<212> TYPE: PRT
<213> ORGANISM: Homo sapiens

<400> SEQUENCE: 42

Gln Gln Phe Gly Ser Ser Pro Trp Thr
1               5

<210> SEQ ID NO 43
<211> LENGTH: 127
<212> TYPE: PRT
<213> ORGANISM: Homo sapiens

<400> SEQUENCE: 43

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 44
<211> LENGTH: 231
<212> TYPE: PRT
<213> ORGANISM: Homo sapiens

<400> SEQUENCE: 44

Gln Val Gln Leu Gln Glu Ser Gly Pro Gly Leu Val Lys Pro Ser Gln
1               5                   10                  15
```

Thr Leu Ser Leu Thr Cys Thr Val Ser Gly Gly Ser Ile Arg Arg Gly
                20                  25                  30

Gly Asp Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
 50                  55                  60

Leu Lys Ser Arg Ala Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Asn Phe Gly Thr Gln Thr Tyr
                195                 200                 205

Thr Cys Asn Val Asp His Lys Pro Ser Asn Thr Lys Val Asp Lys Thr
210                 215                 220

Val Glu Arg Lys Cys Gly Gly
225                 230

<210> SEQ ID NO 45
<211> LENGTH: 231
<212> TYPE: PRT
<213> ORGANISM: Homo sapiens

<400> SEQUENCE: 45

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Arg Gly
                20                  25                  30

Gly Asp Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
 50                  55                  60

Leu Lys Ser Arg Ala Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Tyr Ser Tyr Tyr Tyr Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe

```
                145                 150                 155                 160
Pro Glu Pro Val Thr Val Ser Trp Asn Ser Gly Ala Leu Thr Ser Gly
                    165                 170                 175

Val His Thr Phe Pro Ala Val Leu Gln Ser Ser Gly Leu Tyr Ser Leu
                    180                 185                 190

Glu Ser Val Val Thr Val Pro Ser Ser Asn Phe Gly Thr Gln Thr Tyr
                    195                 200                 205

Thr Cys Asn Val Asp His Lys Pro Ser Asn Thr Lys Val Asp Lys Thr
                    210                 215                 220

Val Glu Arg Lys Cys Gly Gly
225                 230

<210> SEQ ID NO 46
<211> LENGTH: 221
<212> TYPE: PRT
<213> ORGANISM: Homo sapiens

<400> SEQUENCE: 46

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                    20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Ala
                    85                  90                  95

Leu Gln Thr Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                    165                 170                 175

Thr Tyr Ser Leu Lys Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly
210                 215                 220

<210> SEQ ID NO 47
<211> LENGTH: 5
<212> TYPE: PRT
<213> ORGANISM: Artificial Sequence
<220> FEATURE:
<223> OTHER INFORMATION: Synthetic

<400> SEQUENCE: 47

Gly Gly Gly Gly Ser
1               5
```

<210> SEQ ID NO 48
<211> LENGTH: 10
<212> TYPE: PRT
<213> ORGANISM: Artificial Sequence
<220> FEATURE:
<223> OTHER INFORMATION: Synthetic

<400> SEQUENCE: 48

Gly Gly Gly Gly Ser Gly Gly Gly Gly Ser
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Gly Gly Gly Gly Ser Gly Gly Gly Gly Ser Gly Gly Gly Gly Ser
1               5                   10                  15

<210> SEQ ID NO 50
<211> LENGTH: 20
<212> TYPE: PRT
<213> ORGANISM: Artificial Sequence
<220> FEATURE:
<223> OTHER INFORMATION: Synthetic

<400> SEQUENCE: 50

Gly Gly Gly Gly Ser Gly Gly Gly Gly Ser Gly Gly Gly Gly Ser Gly
1               5                   10                  15

Gly Gly Gly Ser
            20

<210> SEQ ID NO 51
<211> LENGTH: 25
<212> TYPE: PRT
<213> ORGANISM: Artificial Sequence
<220> FEATURE:
<223> OTHER INFORMATION: Synthetic

<400> SEQUENCE: 51

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 52
<211> LENGTH: 30
<212> TYPE: PRT
<213> ORGANISM: Artificial Sequence
<220> FEATURE:
<223> OTHER INFORMATION: Synthetic

<400> SEQUENCE: 52

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 53
<211> LENGTH: 5
<212> TYPE: PRT

```
<213> ORGANISM: Artificial Sequence
<220> FEATURE:
<223> OTHER INFORMATION: Synthetic

<400> SEQUENCE: 53

Glu Ala Ala Ala Lys
1               5

<210> SEQ ID NO 54
<211> LENGTH: 46
<212> TYPE: PRT
<213> ORGANISM: Artificial Sequence
<220> FEATURE:
<223> OTHER INFORMATION: Synthetic

<400> SEQUENCE: 54

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 55
<211> LENGTH: 5
<212> TYPE: PRT
<213> ORGANISM: Artificial Sequence
<220> FEATURE:
<223> OTHER INFORMATION: Synthetic

<400> SEQUENCE: 55

Pro Ala Pro Ala Pro
1               5

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ala Glu Ala Ala Ala Lys Glu Ala Ala Ala Lys Ala
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

Val Ser Gln Thr Ser Lys Leu Thr Arg Ala Glu Thr Val Phe Pro Asp
1               5                   10                  15

Val

<210> SEQ ID NO 58
<211> LENGTH: 6
<212> TYPE: PRT
<213> ORGANISM: Artificial Sequence
<220> FEATURE:
<223> OTHER INFORMATION: Synthetic

<400> SEQUENCE: 58
```

```
Pro Leu Gly Leu Trp Ala
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

Arg Val Leu Ala Glu Ala
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Glu Asp Val Val Cys Cys Ser Met Ser Tyr
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Gly Gly Ile Glu Gly Arg Gly Ser
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic

<400> SEQUENCE: 62

Thr Arg His Arg Gln Pro Arg Gly Trp Glu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Ala Gly Asn Arg Val Arg Arg Ser Val Gly
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Arg Arg Arg Arg Arg Arg Arg Arg Arg
```

```
1               5

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Gly Phe Leu Gly
1

<210> SEQ ID NO 66
<211> LENGTH: 4
<212> TYPE: PRT
<213> ORGANISM: Artificial Sequence
<220> FEATURE:
<223> OTHER INFORMATION: Synthetic

<400> SEQUENCE: 66

His His His His
1

<210> SEQ ID NO 67
<211> LENGTH: 5
<212> TYPE: PRT
<213> ORGANISM: Artificial Sequence
<220> FEATURE:
<223> OTHER INFORMATION: Synthetic

<400> SEQUENCE: 67

His His His His His
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

His His His His His His
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic

<400> SEQUENCE: 69

His His His His His His His
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

His His His His His His His His
1               5
```

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

His His His His His His His His His
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic

<400> SEQUENCE: 72

His His His His His His His His His His
1               5                   10

<210> SEQ ID NO 73
<211> LENGTH: 47
<212> TYPE: DNA
<213> ORGANISM: Artificial Sequence
<220> FEATURE:
<223> OTHER INFORMATION: Synthetic

<400> SEQUENCE: 73
agtttaaacg aattcgtcga ctaggccacc atggacatga gggtgcc                    47

<210> SEQ ID NO 74
<211> LENGTH: 30
<212> TYPE: DNA
<213> ORGANISM: Artificial Sequence
<220> FEATURE:
<223> OTHER INFORMATION: Synthetic

<400> SEQUENCE: 74
gtgctggcga atccagctcc aatagtcacc                                       30

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
gagctggatt cgccagcacc cagg                                             24

<210> SEQ ID NO 76
<211> LENGTH: 31
<212> TYPE: DNA
<213> ORGANISM: Artificial Sequence
<220> FEATURE:
<223> OTHER INFORMATION: Synthetic

<400> SEQUENCE: 76
ggtgcccgta gggccacccg agacaggga g                                      31

<210> SEQ ID NO 77
<211> LENGTH: 31
<212> TYPE: DNA

```
<213> ORGANISM: Artificial Sequence
<220> FEATURE:
<223> OTHER INFORMATION: Synthetic

<400> SEQUENCE: 77
tccctgtctc cgggtggccc tacgggcacc g                                31

<210> SEQ ID NO 78
<211> LENGTH: 42
<212> TYPE: DNA
<213> ORGANISM: Artificial Sequence
<220> FEATURE:
<223> OTHER INFORMATION: Synthetic

<400> SEQUENCE: 78
aacgatatcg ctagcgcggc cgctcattcc ttgggattgg tg                    42

<210> SEQ ID NO 79
<211> LENGTH: 31
<212> TYPE: DNA
<213> ORGANISM: Artificial Sequence
<220> FEATURE:
<223> OTHER INFORMATION: Synthetic

<400> SEQUENCE: 79
ggatccgcca ccaccacccg gagacaggga g                                31

<210> SEQ ID NO 80
<211> LENGTH: 31
<212> TYPE: DNA
<213> ORGANISM: Artificial Sequence
<220> FEATURE:
<223> OTHER INFORMATION: Synthetic

<400> SEQUENCE: 80
ggtggtggcg gatccggccc tacgggcacc g                                31

<210> SEQ ID NO 81
<211> LENGTH: 49
<212> TYPE: DNA
<213> ORGANISM: Artificial Sequence
<220> FEATURE:
<223> OTHER INFORMATION: Synthetic

<400> SEQUENCE: 81
gccggaccct cccccaccgg atccgccacc tccacccgga gacagggag             49

<210> SEQ ID NO 82
<211> LENGTH: 50
<212> TYPE: DNA
<213> ORGANISM: Artificial Sequence
<220> FEATURE:
<223> OTHER INFORMATION: Synthetic

<400> SEQUENCE: 82
ccggtggggg agggtccggc cctacgggca ccggtgaatc caaggctcct            50

<210> SEQ ID NO 83
<211> LENGTH: 54
<212> TYPE: DNA
<213> ORGANISM: Artificial Sequence
<220> FEATURE:
<223> OTHER INFORMATION: Synthetic

<400> SEQUENCE: 83
cgtagggccg gaccctcccc caccggagcc ccgcccccg gatccgccac ctcc         54
```

<210> SEQ ID NO 84
<211> LENGTH: 40
<212> TYPE: PRT
<213> ORGANISM: Artificial Sequence
<220> FEATURE:
<223> OTHER INFORMATION: Synthetic

<400> SEQUENCE: 84

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 85

<400> SEQUENCE: 85

000

<210> SEQ ID NO 86
<211> LENGTH: 31
<212> TYPE: DNA
<213> ORGANISM: Artificial Sequence
<220> FEATURE:
<223> OTHER INFORMATION: Synthetic

<400> SEQUENCE: 86
ggaaccacct ccgccggatc cgccacctcc a                                  31

<210> SEQ ID NO 87
<211> LENGTH: 31
<212> TYPE: DNA
<213> ORGANISM: Artificial Sequence
<220> FEATURE:
<223> OTHER INFORMATION: Synthetic

<400> SEQUENCE: 87
ggcggaggtg gttccggggg cggggctcc g                                   31

<210> SEQ ID NO 88
<211> LENGTH: 31
<212> TYPE: DNA
<213> ORGANISM: Artificial Sequence
<220> FEATURE:
<223> OTHER INFORMATION: Synthetic

<400> SEQUENCE: 88
cttggtcatc tccttccggg atgggggcag g                                  31

<210> SEQ ID NO 89
<211> LENGTH: 35
<212> TYPE: DNA
<213> ORGANISM: Artificial Sequence
<220> FEATURE:
<223> OTHER INFORMATION: Synthetic

<400> SEQUENCE: 89
ctgcccccat cccggaagga gatgaccaag aacca                              35

<210> SEQ ID NO 90
<211> LENGTH: 33
<212> TYPE: DNA

```
<213> ORGANISM: Artificial Sequence
<220> FEATURE:
<223> OTHER INFORMATION: Synthetic

<400> SEQUENCE: 90
gaaggagccg tcggacttca gcatgggagg tgt                                    33

<210> SEQ ID NO 91
<211> LENGTH: 31
<212> TYPE: DNA
<213> ORGANISM: Artificial Sequence
<220> FEATURE:
<223> OTHER INFORMATION: Synthetic

<400> SEQUENCE: 91
cctcccatgc tgaagtccga cggctccttc t                                      31

<210> SEQ ID NO 92
<211> LENGTH: 34
<212> TYPE: DNA
<213> ORGANISM: Artificial Sequence
<220> FEATURE:
<223> OTHER INFORMATION: Synthetic

<400> SEQUENCE: 92
gggaggtgtg gtatcgtagt tgttctccgg ctgc                                   34

<210> SEQ ID NO 93
<211> LENGTH: 34
<212> TYPE: DNA
<213> ORGANISM: Artificial Sequence
<220> FEATURE:
<223> OTHER INFORMATION: Synthetic

<400> SEQUENCE: 93
ccggagaaca actacgatac cacacctccc atgc                                   34

<210> SEQ ID NO 94
<211> LENGTH: 42
<212> TYPE: DNA
<213> ORGANISM: Artificial Sequence
<220> FEATURE:
<223> OTHER INFORMATION: Synthetic

<400> SEQUENCE: 94
aacgatatcg ctagcgcggc cgctcaaccc ggagacaggg ag                          42

<210> SEQ ID NO 95
<211> LENGTH: 37
<212> TYPE: DNA
<213> ORGANISM: Artificial Sequence
<220> FEATURE:
<223> OTHER INFORMATION: Synthetic

<400> SEQUENCE: 95 tttttttgc gcgctgtgat attgtgatga ctcagtc                                 37

<210> SEQ ID NO 96
<211> LENGTH: 32
<212> TYPE: DNA
<213> ORGANISM: Artificial Sequence
<220> FEATURE:
<223> OTHER INFORMATION: Synthetic

<400> SEQUENCE: 96
aaaaaacgta cgtttgattt ccaccttggt cc                                     32
```

<210> SEQ ID NO 97
<211> LENGTH: 22
<212> TYPE: PRT
<213> ORGANISM: Artificial Sequence
<220> FEATURE:
<223> OTHER INFORMATION: Synthetic

<400> SEQUENCE: 97

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 98
<211> LENGTH: 50
<212> TYPE: DNA
<213> ORGANISM: Artificial Sequence
<220> FEATURE:
<223> OTHER INFORMATION: Synthetic

<400> SEQUENCE: 98
gtcgactagg ccaccatgga catgagggtg cccgctcagc tcctggggct            50

<210> SEQ ID NO 99
<211> LENGTH: 34
<212> TYPE: DNA
<213> ORGANISM: Artificial Sequence
<220> FEATURE:
<223> OTHER INFORMATION: Synthetic

<400> SEQUENCE: 99
ggtgcccgta gggccacccg agacaggga gagg                              34

<210> SEQ ID NO 100
<211> LENGTH: 16
<212> TYPE: DNA
<213> ORGANISM: Artificial Sequence
<220> FEATURE:
<223> OTHER INFORMATION: Synthetic

<400> SEQUENCE: 100
ggccctacgg gcaccg                                                 16

<210> SEQ ID NO 101
<211> LENGTH: 38
<212> TYPE: DNA
<213> ORGANISM: Artificial Sequence
<220> FEATURE:
<223> OTHER INFORMATION: Synthetic

<400> SEQUENCE: 101
tcgctagcgc ggccgctcat tccttgggat tggtgacg                         38

<210> SEQ ID NO 102
<211> LENGTH: 34
<212> TYPE: DNA
<213> ORGANISM: Artificial Sequence
<220> FEATURE:
<223> OTHER INFORMATION: Synthetic

<400> SEQUENCE: 102
gctctcgagg gagtagagtc ctgaggactg tagg                             34

<210> SEQ ID NO 103

```
<210> SEQ ID NO 103
<211> LENGTH: 32
<212> TYPE: DNA
<213> ORGANISM: Artificial Sequence
<220> FEATURE:
<223> OTHER INFORMATION: Synthetic

<400> SEQUENCE: 103
ctctactccc tcgagagcgt ggtgaccgtg cc                              32

<210> SEQ ID NO 104
<211> LENGTH: 35
<212> TYPE: DNA
<213> ORGANISM: Artificial Sequence
<220> FEATURE:
<223> OTHER INFORMATION: Synthetic

<400> SEQUENCE: 104
cctcctccac aagatttggg ctcaactttc ttgtc                           35

<210> SEQ ID NO 105
<211> LENGTH: 32
<212> TYPE: DNA
<213> ORGANISM: Artificial Sequence
<220> FEATURE:
<223> OTHER INFORMATION: Synthetic

<400> SEQUENCE: 105
caaatcttgt ggaggaggcc ctacgggcac cg                              32

<210> SEQ ID NO 106
<211> LENGTH: 40
<212> TYPE: DNA
<213> ORGANISM: Artificial Sequence
<220> FEATURE:
<223> OTHER INFORMATION: Synthetic

<400> SEQUENCE: 106
atggtgatgg tgaccgcctt ccttgggatt ggtgacgaca                      40

<210> SEQ ID NO 107
<211> LENGTH: 41
<212> TYPE: DNA
<213> ORGANISM: Artificial Sequence
<220> FEATURE:
<223> OTHER INFORMATION: Synthetic

<400> SEQUENCE: 107
atcgctagcg cggccgccta gtggtgatgg tgatggtgac c                    41

<210> SEQ ID NO 108
<211> LENGTH: 32
<212> TYPE: DNA
<213> ORGANISM: Artificial Sequence
<220> FEATURE:
<223> OTHER INFORMATION: Synthetic

<400> SEQUENCE: 108
taggtgcttc cgtactgttc ctcccggggc tt                              32

<210> SEQ ID NO 109
<211> LENGTH: 24
<212> TYPE: DNA
<213> ORGANISM: Artificial Sequence
<220> FEATURE:
<223> OTHER INFORMATION: Synthetic

<400> SEQUENCE: 109
```
cctgagcagc gtcgtcaccg tccc                                                    24

<210> SEQ ID NO 110
<211> LENGTH: 29
<212> TYPE: DNA
<213> ORGANISM: Artificial Sequence
<220> FEATURE:
<223> OTHER INFORMATION: Synthetic

<400> SEQUENCE: 110
cagtacggaa gcacctaccg ggtggtgtc                                               29

<210> SEQ ID NO 111
<211> LENGTH: 36
<212> TYPE: DNA
<213> ORGANISM: Artificial Sequence
<220> FEATURE:
<223> OTHER INFORMATION: Synthetic

<400> SEQUENCE: 111
acggtgacga cgctgctcag gctgtacagg ccgctg                                       36

<210> SEQ ID NO 112
<211> LENGTH: 18
<212> TYPE: DNA
<213> ORGANISM: Artificial Sequence
<220> FEATURE:
<223> OTHER INFORMATION: Synthetic

<400> SEQUENCE: 112
tatcgctagc gcggccgc                                                           18

<210> SEQ ID NO 113
<211> LENGTH: 45
<212> TYPE: DNA
<213> ORGANISM: Artificial Sequence
<220> FEATURE:
<223> OTHER INFORMATION: Synthetic

<400> SEQUENCE: 113
ctgctgtggc tgagaggtgc gcgctgtcag gtgcagctgc aggag                             45

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
gctgaggaga cggtgaccgt                                                         20

<210> SEQ ID NO 115
<211> LENGTH: 34
<212> TYPE: DNA
<213> ORGANISM: Artificial Sequence
<220> FEATURE:
<223> OTHER INFORMATION: Synthetic

<400> SEQUENCE: 115
ggtcaccgtc tcctcagcta gcaccaaggg ccca                                         34

<210> SEQ ID NO 116
<211> LENGTH: 48
<212> TYPE: DNA

```
<213> ORGANISM: Artificial Sequence
<220> FEATURE:
<223> OTHER INFORMATION: Synthetic

<400> SEQUENCE: 116
ttaaacgata tcgctagcgc ggccgctcat tccttgggat tggtgacg              48

<210> SEQ ID NO 117
<211> LENGTH: 45
<212> TYPE: DNA
<213> ORGANISM: Artificial Sequence
<220> FEATURE:
<223> OTHER INFORMATION: Synthetic

<400> SEQUENCE: 117
ctgctgtggc tgagaggtgc gcgctgtgaa attgtgttga cgcag                  45

<210> SEQ ID NO 118
<211> LENGTH: 27
<212> TYPE: DNA
<213> ORGANISM: Artificial Sequence
<220> FEATURE:
<223> OTHER INFORMATION: Synthetic

<400> SEQUENCE: 118
agccaccgtt cgtttgattt ccacctt                                      27

<210> SEQ ID NO 119
<211> LENGTH: 27
<212> TYPE: DNA
<213> ORGANISM: Artificial Sequence
<220> FEATURE:
<223> OTHER INFORMATION: Synthetic

<400> SEQUENCE: 119
atcaaacgaa cggtggctgc accatct                                      27

<210> SEQ ID NO 120
<211> LENGTH: 51
<212> TYPE: DNA
<213> ORGANISM: Artificial Sequence
<220> FEATURE:
<223> OTHER INFORMATION: Synthetic

<400> SEQUENCE: 120
tgtttaaacg atatcgctag cgcggccgcc taacactctc ccctgttgaa g           51

<210> SEQ ID NO 121
<211> LENGTH: 34
<212> TYPE: DNA
<213> ORGANISM: Artificial Sequence
<220> FEATURE:
<223> OTHER INFORMATION: Synthetic

<400> SEQUENCE: 121
ggtcaccgtc tcctcagcct ccaccaaggg cccc                              34

<210> SEQ ID NO 122
<211> LENGTH: 46
<212> TYPE: DNA
<213> ORGANISM: Artificial Sequence
<220> FEATURE:
<223> OTHER INFORMATION: Synthetic

<400> SEQUENCE: 122
ttaaacgata tcgctagcgc ggccgctcaa cccggggaga ggctca                 46
```

```
<210> SEQ ID NO 123
<211> LENGTH: 50
<212> TYPE: DNA
<213> ORGANISM: Artificial Sequence
<220> FEATURE:
<223> OTHER INFORMATION: Synthetic

<400> SEQUENCE: 123
ttaaacgata tcgctagcgc ggccgcctag tggtgatggt gatggtgacc            50

<210> SEQ ID NO 124
<211> LENGTH: 50
<212> TYPE: DNA
<213> ORGANISM: Artificial Sequence
<220> FEATURE:
<223> OTHER INFORMATION: Synthetic

<400> SEQUENCE: 124
tgtttaaacg atatcgctag cgcggccgct caacactctc ccctgttgaa            50
```